United States Patent [19]

Saupe et al.

[11] Patent Number: 4,999,044
[45] Date of Patent: Mar. 12, 1991

[54] HETEROCYCLIC SULFONAMIDES

[75] Inventors: Thomas Saupe, Bammental; Gerhard Klebe; Ulrich Schirmer, both of Heidelberg; Gerhard Paul, Ludwigshafen; Reiner Kober, Fussgoenheim; Bruno Wuerzer, Otterstadt; Rainer Berghaus, Mutterstadt; Norbert Meyer, Ladenburg; Karl-Otto Westphalen, Speyer, all of Fed. Rep. of Germany

[73] Assignee: BASF Aktiengesellschaft, Ludwigshafen, Fed. Rep. of Germany

[21] Appl. No.: 378,986

[22] Filed: Jul. 12, 1989

Related U.S. Application Data

[62] Division of Ser. No. 310,753, Feb. 15, 1989, Pat. No. 4,881,969.

[51] Int. Cl.$^5$ .................. A01N 43/48; C07D 237/30
[52] U.S. Cl. ........................................ 71/92; 544/236
[58] Field of Search ............................ 544/236; 71/92

[56] References Cited

U.S. PATENT DOCUMENTS 4,722,749  1/1988  Lee ............................. 71/94
4,723,987  2/1988  Hanagan ....................... 71/92
4,826,528  5/1989  Mengel et al. ................. 71/92

FOREIGN PATENT DOCUMENTS 0007687  2/1980  European Pat. Off. .

Primary Examiner—Nicholas S. Rizzo
Assistant Examiner—Jyothsna Venkat
Attorney, Agent, or Firm—Keil & Weinkauf

[57] ABSTRACT

Sulfonamides of the general formula I

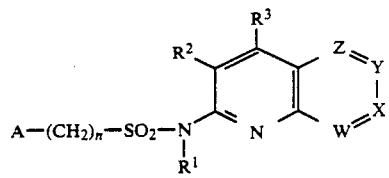

where A, n, $R^1$, $R^2$, $R^3$, W, X, Y and Z have the meanings given in the disclosure and claims, salts and N-oxides thereof, and their use as herbicidal agents.

6 Claims, No Drawings

HETEROCYCLIC SULFONAMIDES

This is a division of application Ser. No. 310,753, filed Feb. 15, 1989, now U.S. Pat. No. 4,881,969.

The present invention relates to sulfonamides of the general formula I

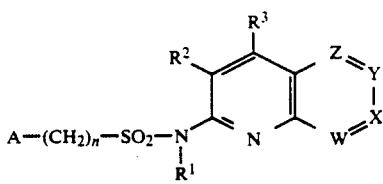

where the substituents and indices are defined as follows:

$R^1$ is hydrogen, cyano, $C_1$-$C_8$-alkyl which may be substituted by one of the following radicals: $C_1$-$C_2$-alkoxy, $C_1$-$C_2$-alkylthio, aryl, aryloxy, arylthio, hetaryl, hetaryloxy and hetarylthio, $C_2$-$C_5$-alkenyl, $C_2$-$C_4$-alkynyl, $COR^4$, where $R^4$ is $C_1$-$C_4$-alkyl, $C_1$-$C_4$alkoxy, $C_1$-$C_4$alkylthio, aryl, aryloxy, arylthio, aryl-$C_1$-$C_4$-alkoxy, hetaryl, hetaryloxy, hetarylthio or hetaryl-$C_1$-$C_4$-alkoxy, $CONR^5R^6$, where $R^5$ and $R^6$ are each independently of the other hydrogen, $C_1$-$C_4$alkyl, $C_3$-$C_6$-cycloalkyl, $C_2$-$C_5$-alkenyl, aryl, hetaryl, aryl-$C_1$-$C_4$-alkyl, hetaryl-$C_1$-$C_4$-alkyl, or $C_1$-$C_4$-alkylcarbonyl or are together a $C_2$-$C_6$-alkylene chain, or $SO_mR^4$, where m is 1 or 2 and $R^4$ is as defined above, $R^2$ and $R^3$ are each independently of the other nitro, hydroxyl, carboxyl, mercapto, halogen, $C_1$-$C_4$alkyl which may be monosubstituted by hydroxyl, mercapto, amino, aryloxy or hetaryloxy and/or monosubstituted, disubstituted or trisubstituted by halogen, $C_3$-$C_6$cycloalkyl, which may be monosubstituted, disubstituted or trisubstituted by halogen, hydroxyl, mercapto and/or $C_1$-$C_4$ -alkyl, $C_3$-$C_6$cycloalkoxy, $C_3$-$C_6$-cycloalkylthio, $C_2$-$C_5$-haloalkenyl, $C_2$-$C_4$-haloalkynyl, $C_1$-$C_4$alkoxy, which may be monosubstituted, disubstituted or trisubstituted by halogen and/or monosubstituted by aryl or hetaryl, $C_1$-$C_4$-alkylthio, which may be monosubstituted, disubstituted or trisubstituted by halogen and/or monosubstituted by aryl or hetaryl, $C_2$-$C_4$-alkenyloxy, $C_2$-$C_4$-alkynyloxy, —$NR^5R^6$, where $R^5$ and $R^6$ are each as defined above, or one of the groups mentioned under $R^1$, W, X, Y and Z are each independently of the others nitrogen or are a group

where $R^7$ is hydrazino or one of the groups mentioned under $R^2$, although X, Y, Z and W are not all nitrogen at the same time, n is 0 or 1 and A is aryl or hetaryl, which each may carry from one to five halogen atoms and/or from one to three of the following substituents: —$SO_2R^8$, where $R^8$ is hydroxyl, $C_1$-$C_4$-alkoxy, aryl-$C_1$-$C_4$-alkoxy, aryloxy, hetaryloxy, hetaryl-$C_1$-$C_4$-alkoxy or —$NR^5R^6$, where $R^5$ and $R^6$ are each as defined above, and/or of groups mentioned under $R^2$ and the salts and N-oxides thereof, except the compounds of the formula I where A is 4-aminophenyl, n is 0, $R^1$, $R^2$ and $R^3$ are each hydrogen, W is nitrogen, X, Y and Z are each carbon, and the $R^4$s on X and Z are each methyl and otherwise hydrogen, and the 4-aminophenyl reaction products thereof.

The present invention further relates to the use of these compounds for controlling unwanted plant growth and the use thereof for affecting plant growth.

EP-A-7,687 and later publications describe sulfonylureas which can have a herbicidal effect. However, they do not meet all the requirements, for example in respect of selectivity and specificity.

It is an object of the present invention to find and synthesize substances having satisfactory properties.

We have found that this object is achieved with the sulfonamides I defined at the beginning, which have a manifold action as herbicides and growth regulators. The present invention also encompasses simple reaction products of these sulfonamides such as salts or N-oxides.

The present invention also includes herbicides and agents for affecting plant growth which contain the novel compounds as active substances, and a process for affecting and controlling plant growth by means of these compounds.

The synthesis of compounds of the general formula I may be carried out in the convergent manner in accordance with scheme 1 by reacting a heterocyclic amine of the formula II, where W, X, Y, Z, $R^1$, $R^2$ and $R^3$ are each as defined above with approximately stoichiometric amounts of a sulfochloride of the formula III where A and n are each as defined above under basic conditions in the presence or absence of an organic solvent at a temperature customary for organic reactions.

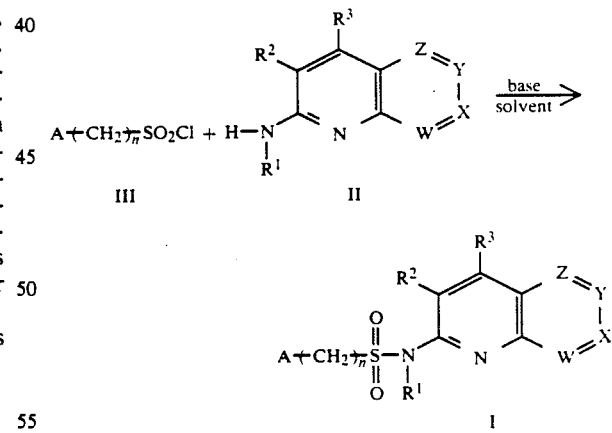

It is convenient to use customary solvents or diluents for the reactions corresponding to scheme 1. These solvents may be halohydrocarbons, in particular chlorohydrocarbons; it is possible to use for example tetrachloroethane, methylene chloride, chloroform, dichloroethane or chlorobenzene. Ethers, for example diethyl ether, tetrahydrofuran or dioxane; dipolar aprotic solvents, in particular acetonitrile, dimethylformamide, dimethylacetamide, dimethyl sulfoxide or N-methylpyrrolidone; aromatics, for example benzene, toluene, pyridine or quinoline, ketones, for example acetone, methyl ethyl ketone, alcohols, for example methanol, ethanol, isopropanol or t-butanol, and mixtures thereof may also be used.

The reactions corresponding to scheme 1 can be carried out at from room temperature to reflux temperature of the particular solvent or solvent mixture.

Suitable catalytically active bases for the reactions corresponding to scheme 1 are aromatic nitrogen bases, for example pyridine, 4-dimethylaminopyridine or quinoline, tertiary aliphatic amines, for example triethylamine or N-methylmorpholine, bi- and tricyclic amines, for example diazabicycloundecene (DBU) or diazabicyclooctane (DABCO), and the hydroxides, hydrides, alkoxides, carbonates and bicarbonates of alkali and alkaline earth metals, in particular NaOH, KOH, NaH, KH, $CaH_2$, LiH, NaOMe, NaOEt, KOtBu, $Na_2CO_3$, $K_2CO_3$, $NaHCO_3$ or $KHCO_3$. In some instances it is also useful to use combinations of the abovementioned bases.

The molar ratios in which the starting compounds required are reacted with one another within the meaning of reaction scheme 1 are in general from 1:1 to 1:3 for the ratio of heterocyclic amine II: sulfonyl chloride III and from 1:1 to 1:5 for the ratio of heterocyclic amine II: catalytically active base. The sulfonyl chlorides III and the reaction-accelerating bases, however, may each also be used in less than stoichiometric amounts.

The reaction concentration for the reactions corresponding to scheme 1 are in general within the range 0.1 to 5 molar, preferably within the range from 0.2 to 2 molar.

In some cases, the use of pyridine as the solvent for the reaction corresponding to scheme 1 may be particularly useful and convenient, since pyridine can act not only as a solvent but also as a reaction-accelerating base.

The sulfochlorides of the general formula III which are required for the reactions corresponding to scheme 1 are in many cases commercially available. Novel sulfochlorides of the formula III may in general be prepared by known methods. Such commonly known methods for preparing sulfochlorides include the sulfochlorination of suitably substituted aromatics, as described for example by H. T. Clarke et al. in Org. Synth. Coll. vol. I, 2nd edn., 1941, page 85 et seq., the diazotization of suitably substituted anilines or heterocyclic amines and subsequent reaction of the resulting diazonium salt with $SO_2$ in the presence of copper(II) chloride, as desrcibed for example by R. V. Hoffmann in Org. Synth. 60 on page 121 et seq., or else the treatment of aromatic alkylthio or benzylthio groups with $Cl_2$ in an aqueous acidic medium.

The heterocyclic amines of the general formula II which are required for the reactions corresponding to scheme 1 may be prepared by known methods, as described for example by P. -A. Lowe in Comprehensive Heterocyclic Chem. (The Structure, Reactions, Synthesis and Uses of Heterocyclic Compounds), vol. 2, 1st ed. (1984), chapter 2.11, by E. Lunt and C. G. Newton in Comprehensive Heterocyclic Chem., vol. 3, 1st ed. (1984), chapter 2.15 and by G.W.H. Cheeseman and R.F. Cookson in The Chemistry of Heterocyclic Compounds, vol. 35, 1979, chapter XXVIII.

Heterocyclic amines of the general formula I which can be prepared in a conventional manner in accordance with the abovementioned sources and the heterocyclic structure of which is substituted for example by one or more OH groups (hereinafter referred to as IIa) may undergo further reactions corresponding to scheme 2 and thus be converted into novel heterocyclic amines of the formula IIb. For instance, such heterocyclic OH groups may be replaced by Cl by using $POCl_3$; this reaction is in general carried out in pure $POCl_3$ under reflux. The heteroaromatic Cl thus introduced into compounds of the formula IIb may in turn be replaced by nucleophiles (Nu) such as alkoxides, thiolates, amines, amides, Grignard compounds, etc. (IIc).

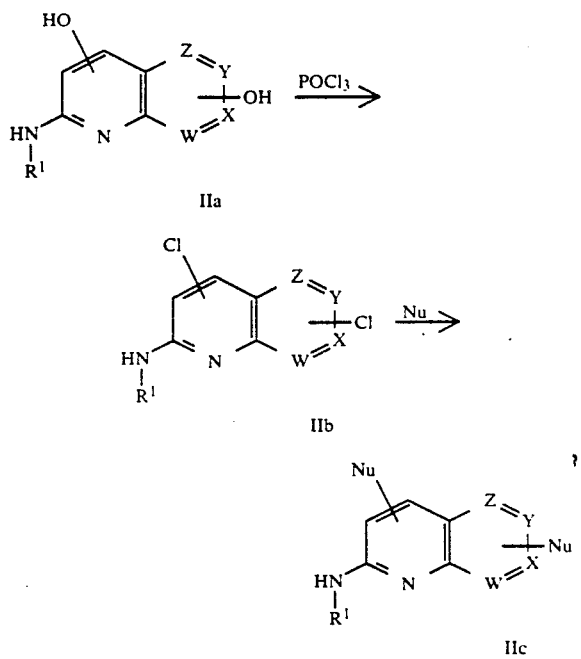

Sulfonamides of the present invention which conform to the general formula I except for the meaning of $R^1$=H may be prepared for example starting from sulfonamides of the general formula I with the meaning of $R_1$=H by reacting, in accordance with scheme 3, a compound of the formula I where $R^1$ is hydrogen with approximately stoichiometric amounts of an electrophile of the formula IV where $R^1$ is not hydrogen and B is a suitable leaving group, for example halogen, in particular Cl, under basic conditions in the absence or presence of a solvent at a temperature customary for organic reactions.

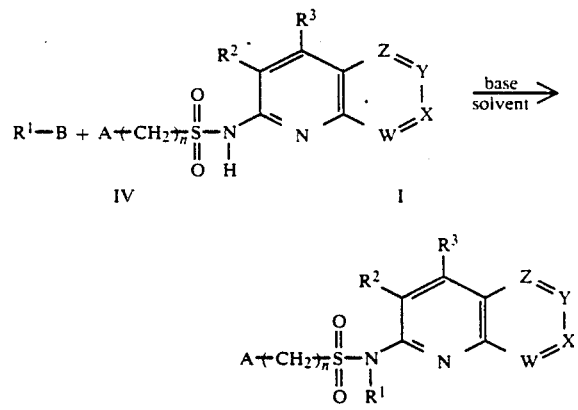

It is convenient to use for the reactions corresponding to scheme 3 solvents and diluents which are inert under the particular reaction conditions. These solvents and diluents may in principle be the same solvents and mixtures as listed above for the reactions corresponding to scheme 1.

The reactions corresponding to scheme 3 may be carried out at from room temperature to the reflux temperature of the particular solvent or solvent mixture.

The reaction-accelerating bases used for the reactions corresponding to scheme 3 may basically be the same bases as mentioned above for the reactions corresponding to scheme 1. In some instances it may also be useful to use certain combinations of these previously mentioned bases.

In certain cases, the use of pyridine as a solvent for the reactions corresponding to scheme 3 can be particularly useful and convenient, since pyridine can act not only as a solvent but also as a reaction-accelerating base.

The molar ratios in which the starting compounds required are reacted with one another within the meaning of reaction scheme 3 are in general from 1:1 to 1:3 for the ratio of compound I with $R^1$—H: electrophile IV with $R^1$=H and from 1:1 to 1:5 for the ratio of compound I with $R^1$=H: catalytically active base.

The reaction concentration for the reactions corresponding to scheme 3 is in general within the range from 0.1 to 5 molar, preferably within the range from 0.2 to 2 molar.

Suitable electrophilic reagents of the general formula IV which are required for the reactions corresponding to scheme 3 are alkyl halides, dialkyl sulfates, arylalkyl halides, for example benzyl chloride, acyl chlorides, aliphatic, aromatic and araliphatic chloroformic esters, chloroformamides (carbamoyl chlorides), alkylsulfonyl chlorides, arylsulfonyl chlorides, aralkylsulfonyl chlorides and also aliphatic, aromatic and araliphatic chlorothioformic esters. Such electrophilic reagents are in general commercially available or are easy to prepare in a conventional manner from readily obtainable intermediates.

The sulfonamides of the general formula I where $R^1$ is H required for the reactions corresponding to scheme 3 are obtainable by the above-described general process which corresponds to the reactions conforming to scheme 1.

N-Oxides (V) of sulfonamides of the general formula I may be prepared in accordance with scheme 4 starting from the corresponding nonoxidized sulfonamides by reacting them with a customary oxidizing agent. If W, X, Y or Z is nitrogen, these nitrogen atoms may of course also form N-oxides.

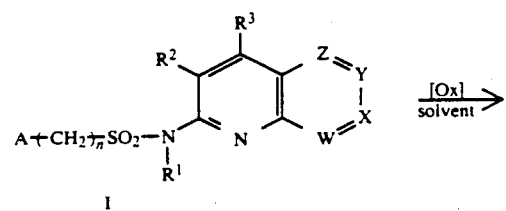

I

-continued

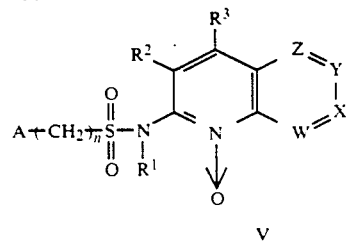

V

It is convenient to use for the reactions corresponding to scheme 4 solvents or diluents which are inert under the particular reaction conditions. They may comprise water, acetic acid and basically the same organic solvents and mixtures as mentioned above for the reactions corresponding to scheme 1.

The reactions corresponding to scheme 4 may be carried out at from room temperature to the reflux temperature of the particular solvent or solvent mixture.

In general, the starting compound of the general formula I corresponding to the general formula Ic is reacted with from one to five equivalents of oxidizing agent Ox.

The reaction concentration for the reaction corresponding to scheme 4 is in general within the range from 0.1 to 5 molar, preferably within the range from 0.2 to 2 molar.

Suitable oxidizing agents Ox for the reactions corresponding to scheme 4 are $H_2O_2$, organic peroxy acids, eg. peracetic acid, perbenzoic acid and substituted perbenzoic acids, organic peroxides, such as tert-butyl hydroperoxide, and inorganic peroxides, eg. $NaWO_4$. These oxidizing agents Ox are generally commercially available.

Having regard to the intended use of the compounds I, preferred initiators are the following radicals:

$R^1$ is hydrogen, cyano, $C_1$-$C_8$-alkyl such as methyl, ethyl, n-propyl, isopropyl, n-butyl, isobutyl, tert-butyl or straight-chain or branched $C_5$- to $C_8$-alkyl, in particular methyl, ethyl, propyl or isopropyl, which group may be substituted by one of the following radicals: alkoxy such as methoxy or ethoxy, alkylthio such as methylthio or ethylthio, aryl or hetaryl such as phenyl or naphthyl, six-membered heterocyclyl incorporating one or more heteroatoms, such as pyridyl, pyridazinyl, pyrimidinyl, pyrazinyl, 1,3,5-triazinyl, 1,2,4-triazinyl, 1,2,3-triazinyl, tetrazinyl, five-membered heterocyclyl incorporating one or more heteroatoms, such as pyrryl, furyl, thienyl, pyrazolyl, imidazolyl, oxazolyl, isoxazolyl, thiazolyl, isothiazolyl, 1,2,3-triazolyl, 1,2,4-triazolyl, tetrazolyl, thiadiazolyl, fused and benzofused hetaryl, such as indolyl, isoindolyl, thionaphthyl, quinolyl, isoquinolyl, cinnolyl, phthalazinyl, quinazolyl, quinoxalyl, indazolyl, naphthyridinyl, benzothiazolyl, benzimidazolyl, benzofuryl, benzoxazolyl and benzotriazolyl, or a corresponding aryloxy or arylthio radical or hetaryloxy or hetarylthio radical, $C_2$-$C_5$-alkenyl, in particular vinyl, allyl, 1-propenyl or butenyl, $C_2$-$C_4$-alkynyl, in particular ethynyl, propynyl or butynyl, —$COR^4$, where $R^4$ is $C_1$-$C_4$-alkyl as mentioned above, in particular methyl, ethyl or isopropyl, $C_1$-$C_4$-alkoxy, in particular methoxy, ethoxy, propoxy or butoxy, which is substituted by one of the aforementioned aryl or hetaryl radicals $C_1$-$C_4$- alkylthio, in particular methylthio, ethylthio, propylthio and butylthio, or aryl, hetaryl, aryloxy, heteroaryloxy, arylthio or heteroarylthio as mentioned above, —CONR$^5$R$^6$, where R$^5$, R$^6$ are each independently of the other hydrogen, and C$_1$–C$_4$-alkyl as mentioned under R$^4$, which is substituted by one of the aforementioned aryl or heteroaryl radicals, C$_3$–C$_6$-cycloalkyl, such as cyclopropyl, cyclobutyl, cyclopentyl or cyclohexyl, C$_2$–C$_5$-alkenyl, aryl and heteroaryl as mentioned above, C$_1$–C$_5$-alkoxycarbonyl such as methylcarbonyl, ethylcarbonyl, propylcarbonyl, isopropylcarbonyl, butylcarbonyl, isobutylcarbonyl, sec-butylcarbonyl or tert-butylcarbonyl, in particular methylcarbonyl, ethylcarbonyl or propylcarbonyl, or are together a C$_2$–C$_6$-alkylene chain such as ethylene, propylene, butylene, pentylene or hexylene, or —SO$_m$R$^4$, where m is 1 or 2 and R$^4$ is as defined above, R$^2$ and R$^3$ are each independently of the other nitro, hydroxyl, carboxyl, mercapto, halogen, in particular fluorine, chlorine or bromine, C$_1$–C$_4$-alkyl as mentioned under R$^1$, in particular methyl, ethyl or isopropyl, which may be monosubstituted, disubstituted or trisubstituted by halogen such as fluorine or chlorine and/or monosubstituted by hydroxyl, mercapto, amino, aryloxy or hetaryloxy as mentioned above, C$_3$–C$_6$-cycloalkyl as mentioned under R$^5$, which may be monosubstituted, disubstituted or trisubstituted by halogen such as fluorine or chlorine, hydroxyl, mercapto and/or the abovementioned C$_1$–C$_4$-alkyl groups, C$_3$–C$_6$-cycloalkoxy, in particular cyclopropyloxy, cyclopentyloxy and cyclohexyloxy and the corresponding cycloalkylthio radicals, C$_2$–C$_5$-haloalkenyl, in particular fluorine- or chlorine mono-, -di- or -trisubstituted allyl, but-2-enyl or but-3-enyl, C$_2$–C$_4$-haloalkynyl, in particular fluorine- or chlorine mono-, -di- or -trisubstituted prop-2-ynyl, but2-ynyl or but-3-ynyl, C$_1$–C$_4$alkoxy as mentioned above under R$^4$, in particular methoxy, ethoxy or isopropyloxy, which radical may be monosubstituted, disubstituted or trisubstituted by halogen such as fluorine or chlorine and/or monosubstituted by aryl or hetaryl such as mentioned under R$^1$, C$_2$–C$_5$-alkenyloxy, in particular allyloxy, but-2-enyloxy or but-3-enyloxy. C$_2$–C$_4$-alkynyloxy, in particular prop-2-ynyloxy, but-2-ynyloxy or but-3-ynyloxy, —NR$^5$R$^6$, where R$^5$ and R$^6$ are each as defined above, or one of the groups mentioned under R$^1$, W, X, Y and Z are each independently of the others nitrogen or a group

where

R$^7$ is hydrazino or one of the groups mentioned under R$^2$, where W, X, Y and Z are not all nitrogen at the same time, n is 0 or 1 and A is one of the aryl or hetaryl groups mentioned under R$^1$, each of which may carry from one to five halogen atoms such as fluorine, chlorine or bromine and/or from one to three of the following substituents: —SO$_2$R$^8$, where R$^8$ is hydroxyl, C$_1$–C$_{14}$-alkoxy as mentioned under R$^4$, which may be substituted by one of the aforementioned aryl or hetaryl radicals, and aryloxy or hetaryloxy radicals as mentioned above or a group—NR$^5$R$^6$, where R$^5$ and R$^6$ are each as defined above, or the groups mentioned under R$^2$.

We exclude compounds of the formula I where A is 4-aminophenyl. n is 0, R$^1$, R$^2$ and R$^3$ are each hydrogen. W is nitrogen, X, Y and Z are each carbon and the R$^4$s on X and Z are methyl and otherwise hydrogen. and the 4-aminophenyl reaction products thereof.

Particularly preferred compounds are sulfonamides of the general formula Ia

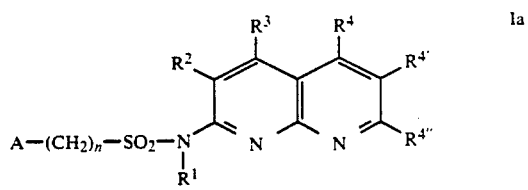

where substituents and indices have the following meanings:

R$^1$ is hydrogen, C$_1$–C$_4$-alkylcarbonyl, which may carry from one to three of the following radicals in the alkyl moiety: halogen atoms, C$_1$–C$_4$-alkoxy groups and/or C$_1$–C$_4$-alkylthio groups, or C$_1$–C$_4$-alkyl which may carry from one to three of the following radicals: halogen atoms, C$_1$–C$_4$-alkoxy groups and/or C$_1$–C$_4$-alkylthio groups, R$^2$ is hydrogen, cyano or halogen, R$^3$ is C$_1$–C$_4$-alkyl or halogen.

R$^4$, R$^{4'}$ and R$^{4''}$ are each independently of the others hydrogen, methyl, trifluoromethyl, methoxy, dimethylamino, methylthio, phenyl, phenoxy, hydrazino or halogen, such as fluorine, chlorine or bromine, n is 0 or 1 and A is phenyl, naphthyl, thienyl or quinolinyl, each of which may carry from one to three of the following groups: halogen, C$_1$–C$_8$-alkyl, C$_1$–C$_4$-alkoxy, C$_1$–C$_2$-alkoxy-C$_1$–C$_4$-alkyl and C$_1$–C$_4$-alkoxycarbonyl, and the salts and N-oxides thereof.

Preference is further given to compounds Ib

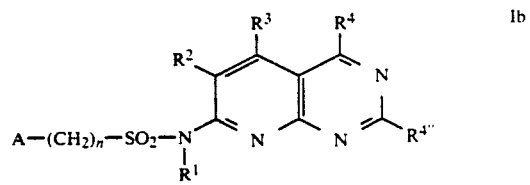

where the substituents and indices have the following meanings:

R$^1$ is hydrogen or methyl,

R$^2$ is hydrogen, cyano, methoxycarbonyl, methylsulfonyl, phenyl or halogen such as chlorine or bromine, R$^3$ is in particular hydrogen, R$^4$ and R$^{4''}$ are each as defined under Ia and A is phenyl or thienyl, which may each carry in particular one or two of the following radicals: halogen such as fluorine, chlorine or bromine, methyl, methoxy, methoxycarbonyl and/or cyclopentyl, and the salts and N-oxides thereof.

Preferred compounds also include sulfonamides of the general formula Ic

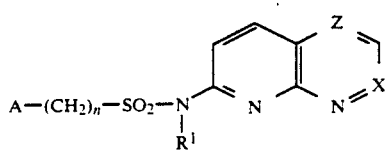

where A, X, Z, n and $R^1$ are each as defined above, and the salts and N-oxides thereof.

Preferred compounds also include sulfonamides of the general formula Id

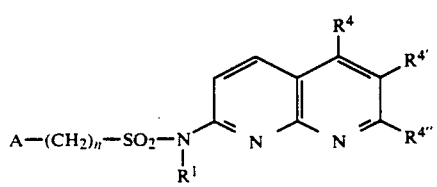

where A, n, $R^1$ and $R^4$, $R^{4'}$ and $R^{4''}$ are each as defined above, and to the salts and N-oxides thereof.

Examples of very active compounds of the formulae Ia, Ib, Ic and Id are listed in the following tables I, II, III and IV:

TABLE I

Ia

| A | n | $R^1$ | $R^2$ | $R^4$ | $R^{4''}$ |
|---|---|---|---|---|---|
| Ph | 0 | H | H | $CH_3$ | $CH_3$ |
| Ph | 1 | H | H | $CH_3$ | $CH_3$ |
| Ph | 0 | $CH_3$ | H | $CH_3$ | $CH_3$ |
| Ph | 1 | $CH_3$ | H | $CH_3$ | $CH_3$ |
| Ph | 0 | $COCH_3$ | H | $CH_3$ | $CH_3$ |
| Ph | 1 | $COCH_3$ | H | $CH_3$ | $CH_3$ |

TABLE I-continued

| A | n | $R^1$ | $R^2$ | $R^4$ | $R^{4''}$ |
|---|---|---|---|---|---|
| Ph | 0 | H | Cl | $CH_3$ | $CH_3$ |
| Ph | 1 | H | Cl | $CH_3$ | $CH_3$ |
| Ph | 0 | $CH_3$ | Cl | $CH_3$ | $CH_3$ |
| Ph | 1 | $CH_3$ | Cl | $CH_3$ | $CH_3$ |
| Ph | 0 | $COCH_3$ | Cl | $CH_3$ | $CH_3$ |
| Ph | 1 | $COCH_3$ | Cl | $CH_3$ | $CH_3$ |
| Ph | 0 | H | CN | $CH_3$ | $CH_3$ |
| Ph | 1 | H | CN | $CH_3$ | $CH_3$ |
| Ph | 0 | $CH_3$ | CN | $CH_3$ | $CH_3$ |
| Ph | 1 | $CH_3$ | CN | $CH_3$ | $CH_3$ |
| Ph | 0 | $COCH_3$ | CN | $CH_3$ | $CH_3$ |
| Ph | 1 | $COCH_3$ | CN | $CH_3$ | $CH_3$ |
| Ph | 0 | H | H | $CH_3$ | Cl |

TABLE I-continued
| Ar | n | R₁ | R₂ | R₃ | R₄ |
|---|---|---|---|---|---|
| 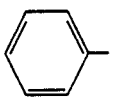 | 1 | H | H | CH₃ | Cl |
| 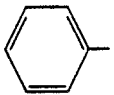 | 0 | CH₃ | H | CH₃ | Cl |
| 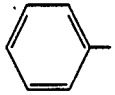 | 1 | CH₃ | H | CH₃ | Cl |
| 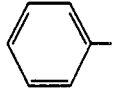 | 0 | COCH₃ | H | CH₃ | Cl |
| 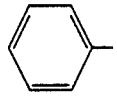 | 1 | COCH₃ | H | CH₃ | Cl |
| 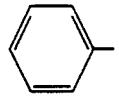 | 0 | H | Cl | CH₃ | Cl |
| 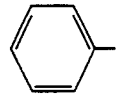 | 1 | H | Cl | CH₃ | Cl |
| 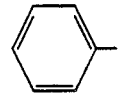 | 0 | CH₃ | Cl | CH₃ | Cl |
| 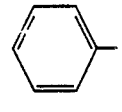 | 1 | CH₃ | Cl | CH₃ | Cl |
| 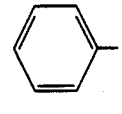 | 0 | COCH₃ | Cl | CH₃ | Cl |
|  | 1 | COCH₃ | Cl | CH₃ | Cl |
|  | 0 | H | CN | CH₃ | Cl |
| 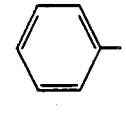 | 1 | H | CN | CH₃ | Cl |
|  | 0 | CH₃ | CN | CH₃ | Cl |
| 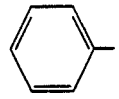 | 1 | CH₃ | CN | CH₃ | Cl |
|  | 0 | COCH₃ | CN | CH₃ | Cl |
|  | 1 | COCH₃ | CN | CH₃ | Cl |
| 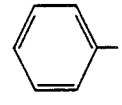 | 0 | H | H | CH₃ | CF₃ |
| 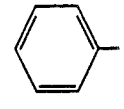 | 1 | H | H | CH₃ | CF₃ |
| 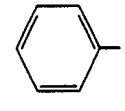 | 0 | CH₃ | H | CH₃ | CF₃ |
|  | 1 | CH₃ | H | CH₃ | CF₃ |
|  | 0 | COCH₃ | H | CH₃ | CF₃ |
| 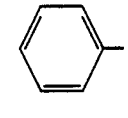 | 1 | COCH₃ | H | CH₃ | CF₃ |
| 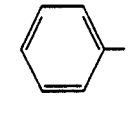 | 0 | H | Cl | CH₃ | CF₃ |
| 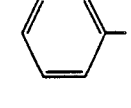 | 1 | H | Cl | CH₃ | CF₃ |
| 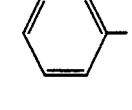 | 0 | CH₃ | Cl | CH₃ | CF₃ |

TABLE I-continued

| | | | | | |
|---|---|---|---|---|---|
|  | 1 | CH₃ | Cl | CH₃ | CF₃ |
|  | 0 | COCH₃ | Cl | CH₃ | CF₃ |
|  | 1 | COCH₃ | Cl | CH₃ | CF₃ |
|  | 0 | H | CN | CH₃ | CF₃ |
|  | 1 | H | CN | CH₃ | CF₃ |
|  | 0 | CH₃ | CN | CH₃ | CF₃ |
|  | 1 | CH₃ | CN | CH₃ | CF₃ |
|  | 0 | COCH₃ | CN | CH₃ | CF₃ |
|  | 1 | COCH₃ | CN | CH₃ | CF₃ |
|  | 0 | H | H | CH₃ | OCH₃ |
|  | 1 | H | H | CH₃ | OCH₃ |
|  | 0 | CH₃ | H | CH₃ | OCH₃ |
|  | 1 | CH₃ | H | CH₃ | OCH₃ |
|  | 0 | COCH₃ | H | CH₃ | OCH₃ |
|  | 1 | COCH₃ | H | CH₃ | OCH₃ |
|  | 0 | H | Cl | CH₃ | OCH₃ |
|  | 1 | H | Cl | CH₃ | OCH₃ |
|  | 0 | CH₃ | Cl | CH₃ | OCH₃ |
|  | 1 | CH₃ | Cl | CH₃ | OCH₃ |
|  | 0 | COCH₃ | Cl | CH₃ | OCH₃ |
|  | 1 | COCH₃ | Cl | CH₃ | OCH₃ |
|  | 0 | H | CN | CH₃ | OCH₃ |
|  | 1 | H | CN | CH₃ | OCH₃ |
|  | 0 | CH₃ | CN | CH₃ | OCH₃ |
|  | 1 | CH₃ | CN | CH₃ | OCH₃ |
|  | 0 | COCH₃ | CN | CH₃ | OCH₃ |

TABLE I-continued

| | | | | | |
|---|---|---|---|---|---|
|  | 1 | COCH$_3$ | CN | CH$_3$ | OCH$_3$ |
|  | 0 | H | H | CF$_3$ | CH$_3$ |
|  | 1 | H | H | CF$_3$ | CH$_3$ |
|  | 0 | CH$_3$ | H | CF$_3$ | CH$_3$ |
|  | 1 | CH$_3$ | H | CF$_3$ | CH$_3$ |
|  | 0 | COCH$_3$ | H | CF$_3$ | CH$_3$ |
|  | 1 | COCH$_3$ | H | CF$_3$ | CH$_3$ |
|  | 0 | H | Cl | CF$_3$ | CH$_3$ |
|  | 1 | H | Cl | CF$_3$ | CH$_3$ |
|  | 0 | CH$_3$ | Cl | CF$_3$ | CH$_3$ |
|  | 1 | CH$_3$ | Cl | CF$_3$ | CH$_3$ |
|  | 0 | COCH$_3$ | Cl | CF$_3$ | CH$_3$ |
|  | 1 | COCH$_3$ | Cl | CF$_3$ | CH$_3$ |
|  | 0 | H | CN | CF$_3$ | CH$_3$ |
|  | 1 | H | CN | CF$_3$ | CH$_3$ |
|  | 0 | CH$_3$ | CN | CF$_3$ | CH$_3$ |
|  | 1 | CH$_3$ | CN | CF$_3$ | CH$_3$ |
|  | 0 | COCH$_3$ | CN | CF$_3$ | CH$_3$ |
|  | 1 | COCH$_3$ | CN | CF$_3$ | CH$_3$ |
|  | 0 | H | H | CF$_3$ | CF$_3$ |
|  | 1 | H | H | CF$_3$ | CF$_3$ |
|  | 0 | CH$_3$ | H | CF$_3$ | CF$_3$ |
|  | 1 | CH$_3$ | H | CF$_3$ | CF$_3$ |
|  | 0 | COCH$_3$ | H | CF$_3$ | CF$_3$ |
|  | 1 | COCH$_3$ | H | CF$_3$ | CF$_3$ |
|  | 0 | H | Cl | CF$_3$ | CF$_3$ |

TABLE I-continued

| Ar | n | R | X | Y | Z |
|---|---|---|---|---|---|
| 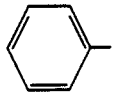 | 1 | H | Cl | CF$_3$ | CF$_3$ |
| 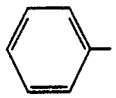 | 0 | CH$_3$ | Cl | CF$_3$ | CF$_3$ |
| 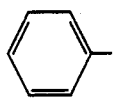 | 1 | CH$_3$ | Cl | CF$_3$ | CF$_3$ |
| 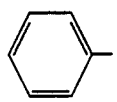 | 0 | COCH$_3$ | Cl | CF$_3$ | CF$_3$ |
| 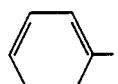 | 1 | COCH$_3$ | Cl | CF$_3$ | CF$_3$ |
| 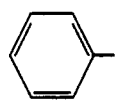 | 0 | H | CN | CF$_3$ | CF$_3$ |
|  | 1 | H | CN | CF$_3$ | CF$_3$ |
|  | 0 | CH$_3$ | CN | CF$_3$ | CF$_3$ |
| 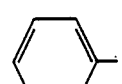 | 1 | CH$_3$ | CN | CF$_3$ | CF$_3$ |
| 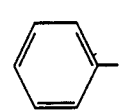 | 0 | COCH$_3$ | CN | CF$_3$ | CF$_3$ |
|  | 1 | COCH$_3$ | CN | CF$_3$ | CF$_3$ |
| 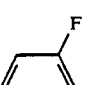 | 0 | H | H | CH$_3$ | CH$_3$ |
| 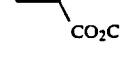 | 1 | H | H | CH$_3$ | CH$_3$ |
| 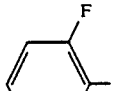 | 0 | CH$_3$ | H | CH$_3$ | CH$_3$ |
| 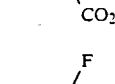 | 1 | CH$_3$ | H | CH$_3$ | CH$_3$ |
| 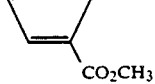 | 0 | COCH$_3$ | H | CH$_3$ | CH$_3$ |
| 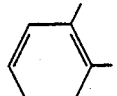 | 1 | COCH$_3$ | H | CH$_3$ | CH$_3$ |
| 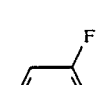 | 0 | H | Cl | CH$_3$ | CH$_3$ |
| 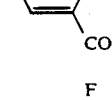 | 1 | H | Cl | CH$_3$ | CH$_3$ |
| 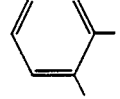 | 0 | CH$_3$ | Cl | CH$_3$ | CH$_3$ |
| 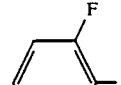 | 1 | CH$_3$ | Cl | CH$_3$ | CH$_3$ |

TABLE I-continued
| Ar | n | R | X | R₁ | R₂ |
|---|---|---|---|---|---|
| 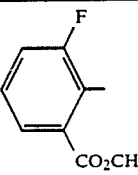 | 0 | COCH₃ | Cl | CH₃ | CH₃ |
| 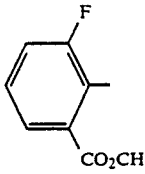 | 1 | COCH₃ | Cl | CH₃ | CH₃ |
| 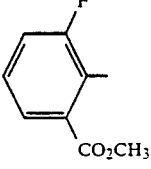 | 0 | H | CN | CH₃ | CH₃ |
| 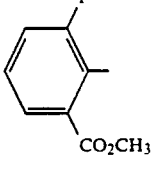 | 1 | H | CN | CH₃ | CH₃ |
| 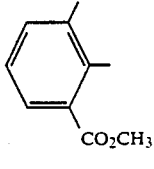 | 0 | CH₃ | CN | CH₃ | CH₃ |
| 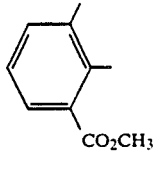 | 1 | CH₃ | CN | CH₃ | CH₃ |
| 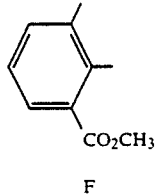 | 0 | COCH₃ | CN | CH₃ | CH₃ |
| 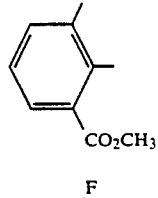 | 1 | COCH₃ | CN | CH₃ | CH₃ |
| 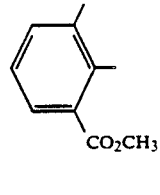 | 0 | H | H | CH₃ | Cl |
| 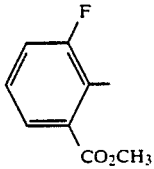 | 1 | H | H | CH₃ | Cl |
| 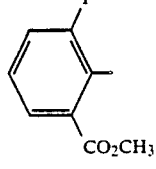 | 0 | CH₃ | H | CH₃ | Cl |
| 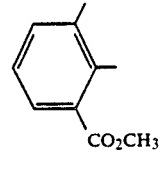 | 1 | CH₃ | H | CH₃ | Cl |
| 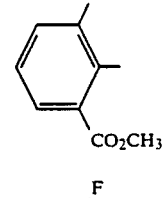 | 0 | COCH₃ | H | CH₃ | Cl |
| 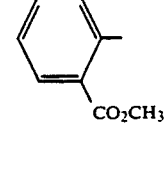 | 1 | COCH₃ | H | CH₃ | Cl |
|  | 0 | H | Cl | CH₃ | Cl |
|  | 1 | H | Cl | CH₃ | Cl |
|  | 0 | CH₃ | Cl | CH₃ | Cl |
|  | 1 | CH₃ | Cl | CH₃ | Cl |

TABLE I-continued

| Ar | n | R1 | R2 | R3 | R4 |
|---|---|---|---|---|---|
| 3-F-2-(CO2CH3)-C6H3 | 0 | COCH3 | Cl | CH3 | Cl |
| 3-F-2-(CO2CH3)-C6H3 | 1 | COCH3 | Cl | CH3 | Cl |
| 3-F-2-(CO2CH3)-C6H3 | 0 | H | CN | CH3 | Cl |
| 3-F-2-(CO2CH3)-C6H3 | 1 | H | CN | CH3 | Cl |
| 3-F-2-(CO2CH3)-C6H3 | 0 | CH3 | CN | CH3 | Cl |
| 3-F-2-(CO2CH3)-C6H3 | 1 | CH3 | CN | CH3 | Cl |
| 3-F-2-(CO2CH3)-C6H3 | 0 | COCH3 | CN | CH3 | Cl |
| 3-F-2-(CO2CH3)-C6H3 | 1 | COCH3 | CN | CH3 | Cl |
| 3-F-2-(CO2CH3)-C6H3 | 0 | H | H | CH3 | CF3 |
| 3-F-2-(CO2CH3)-C6H3 | 1 | H | H | CH3 | CF3 |
| 3-F-2-(CO2CH3)-C6H3 | 0 | CH3 | H | CH3 | CF3 |
| 3-F-2-(CO2CH3)-C6H3 | 1 | CH3 | H | CH3 | CF3 |
| 3-F-2-(CO2CH3)-C6H3 | 0 | COCH3 | H | CH3 | CF3 |
| 3-F-2-(CO2CH3)-C6H3 | 1 | COCH3 | H | CH3 | CF3 |
| 3-F-2-(CO2CH3)-C6H3 | 0 | H | Cl | CH3 | CF3 |
| 3-F-2-(CO2CH3)-C6H3 | 1 | H | Cl | CH3 | CF3 |
| 3-F-2-(CO2CH3)-C6H3 | 0 | CH3 | Cl | CH3 | CF3 |

TABLE I-continued

| Structure | | | | | |
|---|---|---|---|---|---|
| 3-F, 2-CO₂CH₃-phenyl | 1 | CH₃ | Cl | CH₃ | CF₃ |
| 3-F, 2-CO₂CH₃-phenyl | 0 | COCH₃ | Cl | CH₃ | CF₃ |
| 3-F, 2-CO₂CH₃-phenyl | 1 | COCH₃ | Cl | CH₃ | CF₃ |
| 3-F, 2-CO₂CH₃-phenyl | 0 | H | CN | CH₃ | CF₃ |
| 3-F, 2-CO₂CH₃-phenyl | 1 | H | CN | CH₃ | CF₃ |
| 3-F, 2-CO₂CH₃-phenyl | 0 | CH₃ | CN | CH₃ | CF₃ |
| 3-F, 2-CO₂CH₃-phenyl | 1 | CH₃ | CN | CH₃ | CF₃ |
| 3-F, 2-CO₂CH₃-phenyl | 0 | COCH₃ | CN | CH₃ | CF₃ |
| 3-F, 2-CO₂CH₃-phenyl | 1 | COCH₃ | CN | CH₃ | CF₃ |
| 3-F, 2-CO₂CH₃-phenyl | 0 | H | H | CH₃ | OCH₃ |
| 3-F, 2-CO₂CH₃-phenyl | 1 | H | H | CH₃ | OCH₃ |
| 3-F, 2-CO₂CH₃-phenyl | 0 | CH₃ | H | CH₃ | OCH₃ |
| 3-F, 2-CO₂CH₃-phenyl | 1 | CH₃ | H | CH₃ | OCH₃ |
| 3-F, 2-CO₂CH₃-phenyl | 0 | COCH₃ | H | CH₃ | OCH₃ |
| 3-F, 2-CO₂CH₃-phenyl | 1 | COCH₃ | H | CH₃ | OCH₃ |
| 3-F, 2-CO₂CH₃-phenyl | 0 | H | Cl | CH₃ | OCH₃ |
| 3-F, 2-CO₂CH₃-phenyl | 1 | H | Cl | CH₃ | OCH₃ |

| Ar | n | R² | R³ | R⁴ | R⁵ |
|---|---|---|---|---|---|
| 3-F-2-(CO₂CH₃)-C₆H₃ | 0 | CH₃ | Cl | CH₃ | OCH₃ |
| 3-F-2-(CO₂CH₃)-C₆H₃ | 1 | CH₃ | Cl | CH₃ | OCH₃ |
| 3-F-2-(CO₂CH₃)-C₆H₃ | 0 | COCH₃ | Cl | CH₃ | OCH₃ |
| 3-F-2-(CO₂CH₃)-C₆H₃ | 1 | COCH₃ | Cl | CH₃ | OCH₃ |
| 3-F-2-(CO₂CH₃)-C₆H₃ | 0 | H | CN | CH₃ | OCH₃ |
| 3-F-2-(CO₂CH₃)-C₆H₃ | 1 | H | CN | CH₃ | OCH₃ |
| 3-F-2-(CO₂CH₃)-C₆H₃ | 0 | CH₃ | CN | CH₃ | OCH₃ |
| 3-F-2-(CO₂CH₃)-C₆H₃ | 1 | CH₃ | CN | CH₃ | OCH₃ |
| 3-F-2-(CO₂CH₃)-C₆H₃ | 0 | COCH₃ | CN | CH₃ | OCH₃ |
| 3-F-2-(CO₂CH₃)-C₆H₃ | 1 | COCH₃ | CN | CH₃ | OCH₃ |
| 3-F-2-(CO₂CH₃)-C₆H₃ | 0 | H | H | CF₃ | CH₃ |
| 3-F-2-(CO₂CH₃)-C₆H₃ | 1 | H | H | CF₃ | CH₃ |
| 3-F-2-(CO₂CH₃)-C₆H₃ | 0 | CH₃ | H | CF₃ | CH₃ |
| 3-F-2-(CO₂CH₃)-C₆H₃ | 1 | CH₃ | H | CF₃ | CH₃ |
| 3-F-2-(CO₂CH₃)-C₆H₃ | 0 | COCH₃ | H | CF₃ | CH₃ |
| 3-F-2-(CO₂CH₃)-C₆H₃ | 1 | COCH₃ | H | CF₃ | CH₃ |
| 3-F-2-(CO₂CH₃)-C₆H₃ | 0 | H | Cl | CF₃ | CH₃ |
| 3-F-2-(CO₂CH₃)-C₆H₃ | 1 | H | Cl | CF₃ | CH₃ |

| Ar | n | R | X | Y | Z |
|---|---|---|---|---|---|
| 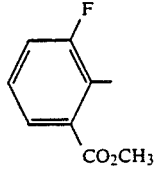 3-F-2-(CO₂CH₃)C₆H₃ | 0 | CH₃ | Cl | CF₃ | CH₃ |
| 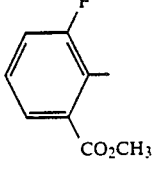 3-F-2-(CO₂CH₃)C₆H₃ | 1 | CH₃ | Cl | CF₃ | CH₃ |
| 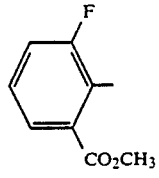 3-F-2-(CO₂CH₃)C₆H₃ | 0 | COCH₃ | Cl | CF₃ | CH₃ |
| 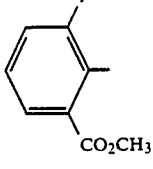 3-F-2-(CO₂CH₃)C₆H₃ | 1 | COCH₃ | Cl | CF₃ | CH₃ |
| 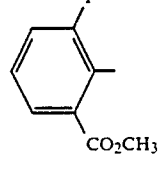 3-F-2-(CO₂CH₃)C₆H₃ | 0 | H | CN | CF₃ | CH₃ |
| 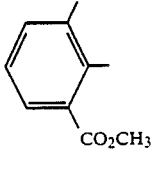 3-F-2-(CO₂CH₃)C₆H₃ | 1 | H | CN | CF₃ | CH₃ |
| 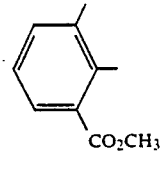 3-F-2-(CO₂CH₃)C₆H₃ | 0 | CH₃ | CN | CF₃ | CH₃ |
| 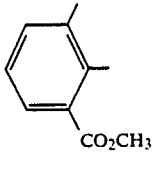 3-F-2-(CO₂CH₃)C₆H₃ | 1 | CH₃ | CN | CF₃ | CH₃ |
| 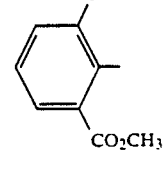 3-F-2-(CO₂CH₃)C₆H₃ | 0 | COCH₃ | CN | CF₃ | CH₃ |
| 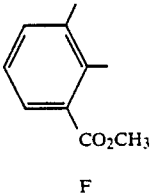 3-F-2-(CO₂CH₃)C₆H₃ | 1 | COCH₃ | CN | CF₃ | CH₃ |
| 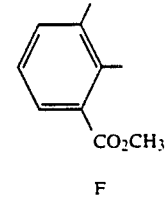 3-F-2-(CO₂CH₃)C₆H₃ | 0 | H | H | CF₃ | CF₃ |
| 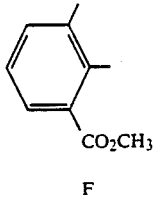 3-F-2-(CO₂CH₃)C₆H₃ | 1 | H | H | CF₃ | CF₃ |
| 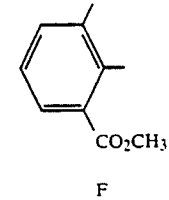 3-F-2-(CO₂CH₃)C₆H₃ | 0 | CH₃ | H | CF₃ | CF₃ |
| 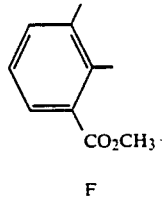 3-F-2-(CO₂CH₃)C₆H₃ | 1 | CH₃ | H | CF₃ | CF₃ |
| 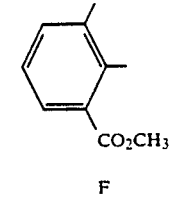 3-F-2-(CO₂CH₃)C₆H₃ | 0 | COCH₃ | H | CF₃ | CF₃ |
| 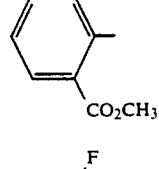 3-F-2-(CO₂CH₃)C₆H₃ | 1 | COCH₃ | H | CF₃ | CF₃ |
| 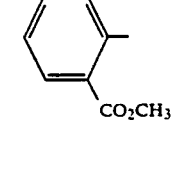 3-F-2-(CO₂CH₃)C₆H₃ | 0 | H | Cl | CF₃ | CF₃ |
| 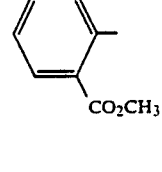 3-F-2-(CO₂CH₃)C₆H₃ | 1 | H | Cl | CF₃ | CF₃ |

| Ar | n | R | X | Y | Z |
|---|---|---|---|---|---|
| 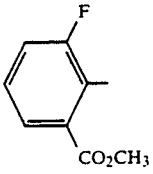 | 0 | CH₃ | Cl | CF₃ | CF₃ |
| 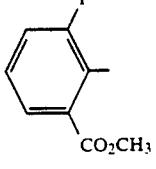 | 1 | CH₃ | Cl | CF₃ | CF₃ |
| 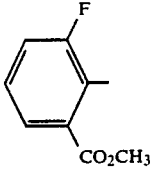 | 0 | COCH₃ | Cl | CF₃ | CF₃ |
| 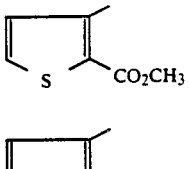 | 1 | COCH₃ | Cl | CF₃ | CF₃ |
| 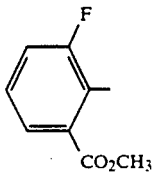 | 0 | H | CN | CF₃ | CF₃ |
| 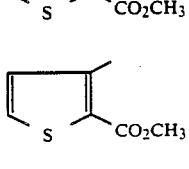 | 1 | H | CN | CF₃ | CF₃ |
| 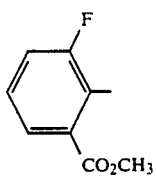 | 0 | CH₃ | CN | CF₃ | CF₃ |
| 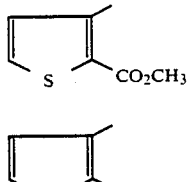 | 1 | CH₃ | CN | CF₃ | CF₃ |
| 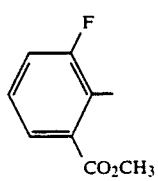 | 0 | COCH₃ | CN | CF₃ | CF₃ |
| 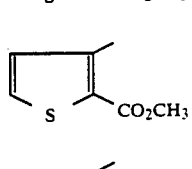 | 1 | COCH₃ | CN | CF₃ | CF₃ |
| 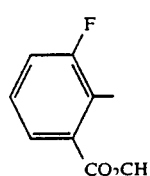 | 0 | H | H | CH₃ | CH₃ |
| 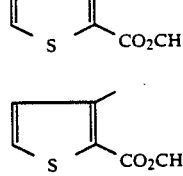 | 1 | H | H | CH₃ | CH₃ |
| 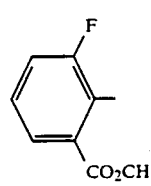 | 0 | CH₃ | H | CH₃ | CH₃ |
| 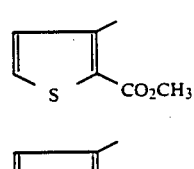 | 1 | CH₃ | H | CH₃ | CH₃ |
| 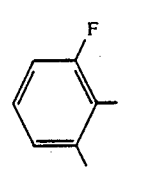 | 0 | COCH₃ | H | CH₃ | CH₃ |
| 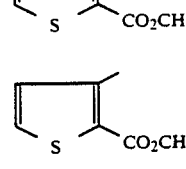 | 1 | COCH₃ | H | CH₃ | CH₃ |
| 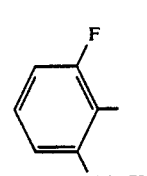 | 0 | H | Cl | CH₃ | CH₃ |
| 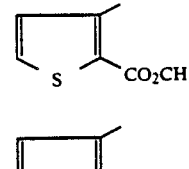 | 1 | H | Cl | CH₃ | CH₃ |
|  | 0 | CH₃ | Cl | CH₃ | CH₃ |
| 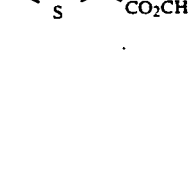 | 1 | CH₃ | Cl | CH₃ | CH₃ |
| 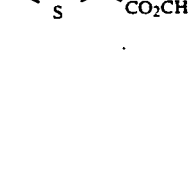 | 0 | COCH₃ | Cl | CH₃ | CH₃ |
| 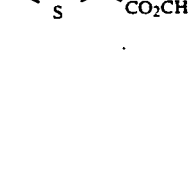 | 1 | COCH₃ | Cl | CH₃ | CH₃ |
| 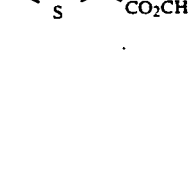 | 0 | H | CN | CH₃ | CH₃ |
| 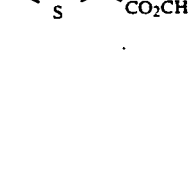 | 1 | COCH₃ | CN | CF₃ | CF₃ |

| Structure | | | | | |
|---|---|---|---|---|---|
| 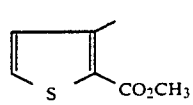 | 1 | H | CN | CH₃ | CH₃ |
| 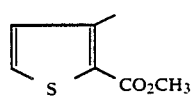 | 0 | CH₃ | CN | CH₃ | CH₃ |
| 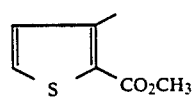 | 1 | CH₃ | CN | CH₃ | CH₃ |
| 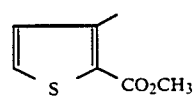 | 0 | COCH₃ | CN | CH₃ | CH₃ |
| 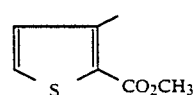 | 1 | COCH₃ | CN | CH₃ | CH₃ |
| 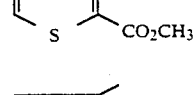 | 0 | H | H | CH₃ | Cl |
| 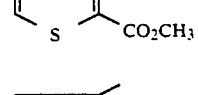 | 1 | H | H | CH₃ | Cl |
| 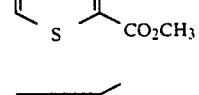 | 0 | CH₃ | H | CH₃ | Cl |
| 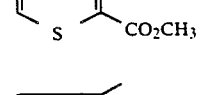 | 1 | CH₃ | H | CH₃ | Cl |
| 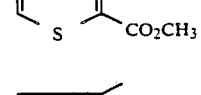 | 0 | COCH₃ | H | CH₃ | Cl |
| 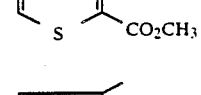 | 1 | COCH₃ | H | CH₃ | Cl |
| 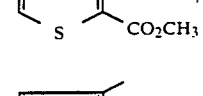 | 0 | H | Cl | CH₃ | Cl |
| 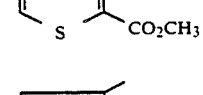 | 1 | H | Cl | CH₃ | Cl |
| 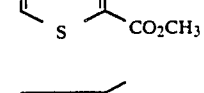 | 0 | CH₃ | Cl | CH₃ | Cl |
| 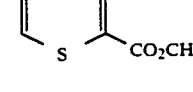 | 1 | CH₃ | Cl | CH₃ | Cl |
| 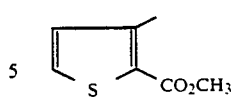 | 0 | COCH₃ | Cl | CH₃ | Cl |
| 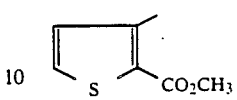 | 1 | COCH₃ | Cl | CH₃ | Cl |
| 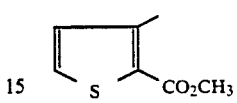 | 0 | H | CN | CH₃ | Cl |
| 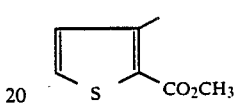 | 1 | H | CN | CH₃ | Cl |
| 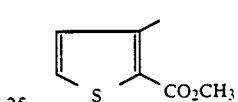 | 0 | CH₃ | CN | CH₃ | Cl |
| 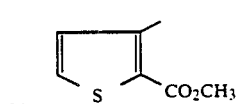 | 1 | CH₃ | CN | CH₃ | Cl |
| 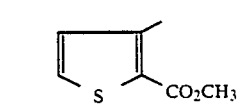 | 0 | COCH₃ | CN | CH₃ | Cl |
| 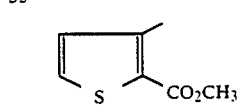 | 1 | COCH₃ | CN | CH₃ | Cl |
| 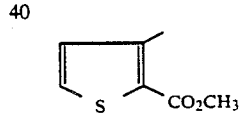 | 0 | H | H | CH₃ | CF₃ |
| 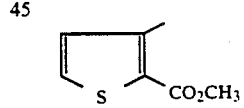 | 1 | H | H | CH₃ | CF₃ |
| 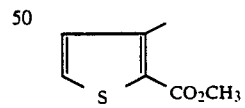 | 0 | CH₃ | H | CH₃ | CF₃ |
| 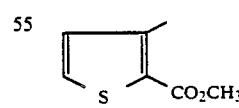 | 1 | CH₃ | H | CH₃ | CF₃ |
| 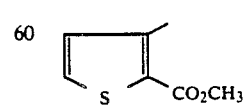 | 0 | COCH₃ | H | CH₃ | CF₃ |

| | | | | | |
|---|---|---|---|---|---|
| 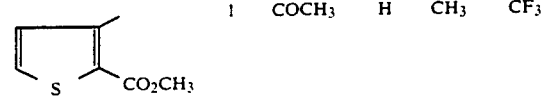 | 1 | COCH₃ | H | CH₃ | CF₃ |
| 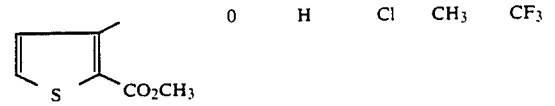 | 0 | H | Cl | CH₃ | CF₃ |
| 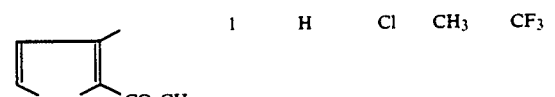 | 1 | H | Cl | CH₃ | CF₃ |
| 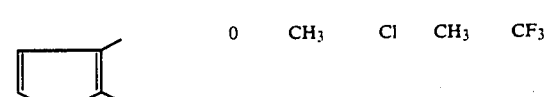 | 0 | CH₃ | Cl | CH₃ | CF₃ |
| 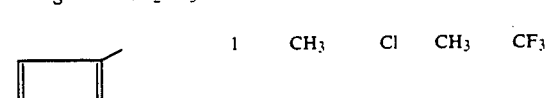 | 1 | CH₃ | Cl | CH₃ | CF₃ |
| 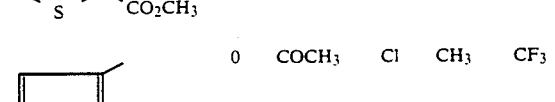 | 0 | COCH₃ | Cl | CH₃ | CF₃ |
| 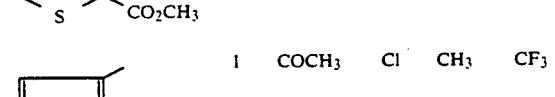 | 1 | COCH₃ | Cl | CH₃ | CF₃ |
| 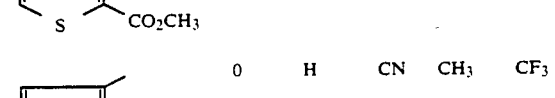 | 0 | H | CN | CH₃ | CF₃ |
| 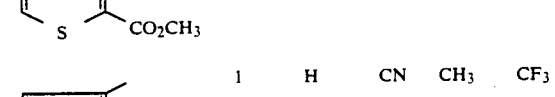 | 1 | H | CN | CH₃ | CF₃ |
| 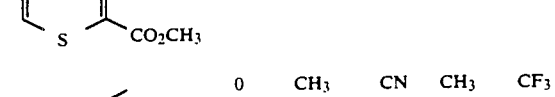 | 0 | CH₃ | CN | CH₃ | CF₃ |
| 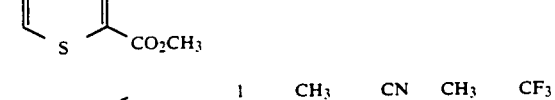 | 1 | CH₃ | CN | CH₃ | CF₃ |
| 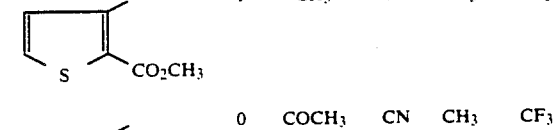 | 0 | COCH₃ | CN | CH₃ | CF₃ |
|  | 1 | COCH₃ | CN | CH₃ | CF₃ |
|  | 0 | H | H | CH₃ | OCH₃ |
| 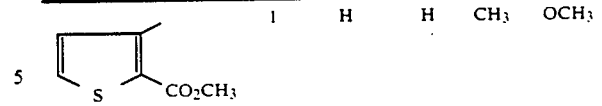 | 1 | H | H | CH₃ | OCH₃ |
| 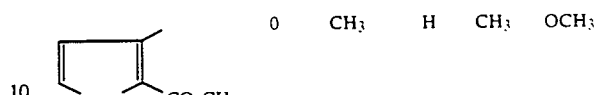 | 0 | CH₃ | H | CH₃ | OCH₃ |
| 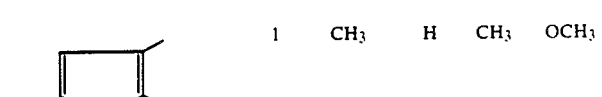 | 1 | CH₃ | H | CH₃ | OCH₃ |
| 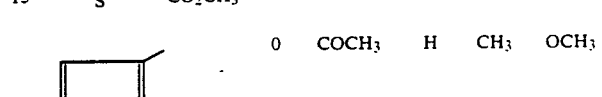 | 0 | COCH₃ | H | CH₃ | OCH₃ |
| 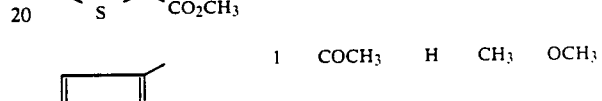 | 1 | COCH₃ | H | CH₃ | OCH₃ |
| 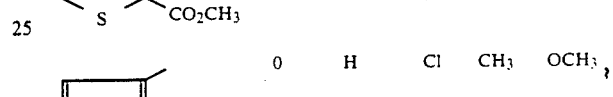 | 0 | H | Cl | CH₃ | OCH₃, |
| 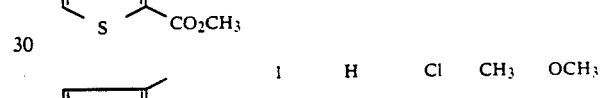 | 1 | H | Cl | CH₃ | OCH₃ |
| 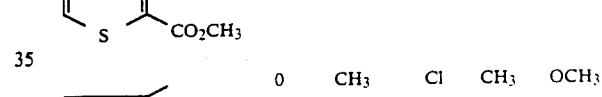 | 0 | CH₃ | Cl | CH₃ | OCH₃ |
| 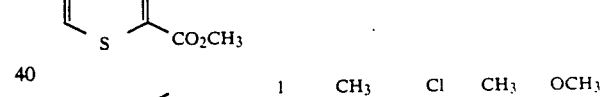 | 1 | CH₃ | Cl | CH₃ | OCH₃ |
| 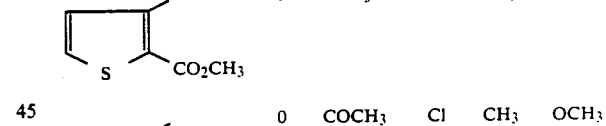 | 0 | COCH₃ | Cl | CH₃ | OCH₃ |
| 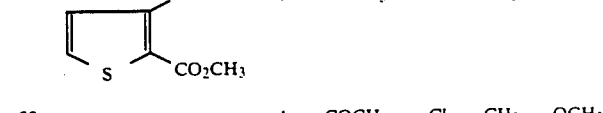 | 1 | COCH₃ | Cl | CH₃ | OCH₃ |
|  | 0 | H | CN | CH₃ | OCH₃ |
|  | 1 | H | CN | CH₃ | OCH₃ |
| 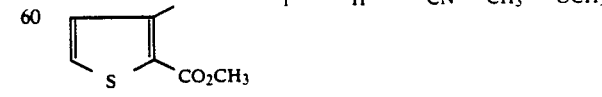 | 0 | CH₃ | CN | CH₃ | OCH₃ |

-continued

| Structure | | | | | |
|---|---|---|---|---|---|
| 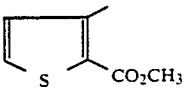 | 1 | CH₃ | CN | CH₃ | OCH₃ |
| 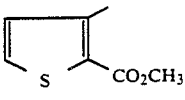 | 0 | COCH₃ | CN | CH₃ | OCH₃ |
| 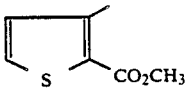 | 1 | COCH₃ | CN | CH₃ | OCH₃ |
| 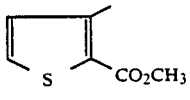 | 0 | H | H | CF₃ | CH₃ |
| 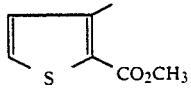 | 1 | H | H | CF₃ | CH₃ |
| 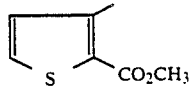 | 0 | CH₃ | H | CF₃ | CH₃ |
| 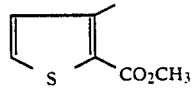 | 1 | CH₃ | H | CF₃ | CH₃ |
| 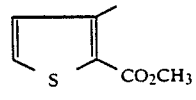 | 0 | COCH₃ | H | CF₃ | CH₃ |
| 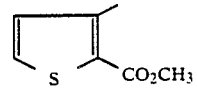 | 1 | COCH₃ | H | CF₃ | CH₃ |
| 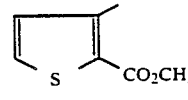 | 0 | H | Cl | CF₃ | CH₃ |
| 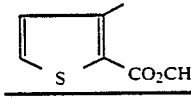 | 1 | H | Cl | CF₃ | CH₃ |
| 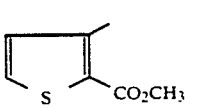 | 0 | CH₃ | Cl | CF₃ | CH₃ |
| 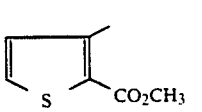 | 1 | CH₃ | Cl | CF₃ | CH₃ |
| 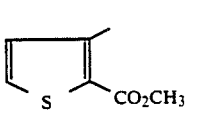 | 0 | COCH₃ | Cl | CF₃ | CH₃ |

-continued

| Structure | | | | | |
|---|---|---|---|---|---|
| 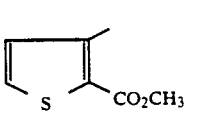 | 1 | COCH₃ | Cl | CF₃ | CH₃ |
| 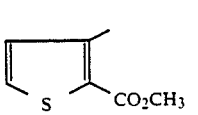 | 0 | H | CN | CF₃ | CH₃ |
| 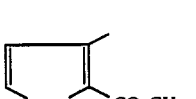 | 1 | H | CN | CF₃ | CH₃ |
| 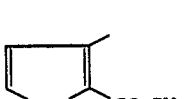 | 0 | CH₃ | CN | CF₃ | CH₃ |
| 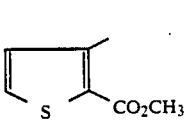 | 1 | CH₃ | CN | CF₃ | CH₃ |
|  | 0 | COCH₃ | CN | CF₃ | CH₃ |
|  | 1 | COCH₃ | CN | CF₃ | CH₃ |
|  | 0 | H | H | CF₃ | CF₃ |
|  | 1 | H | H | CF₃ | CF₃ |
|  | 0 | CH₃ | H | CF₃ | CF₃ |
|  | 1 | CH₃ | H | CF₃ | CF₃ |
|  | 0 | COCH₃ | H | CF₃ | CF₃ |
| | 1 | COCH₃ | H | CF₃ | CF₃ |
| | 0 | H | Cl | CF₃ | CF₃ |

| Structure | n | R | X | Y | Z |
|---|---|---|---|---|---|
| 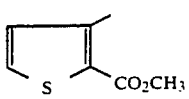 | 1 | H | Cl | CF₃ | CF₃ |
| 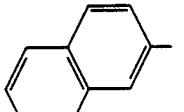 | 0 | CH₃ | Cl | CF₃ | CF₃ |
| 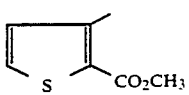 | 1 | CH₃ | Cl | CF₃ | CF₃ |
| 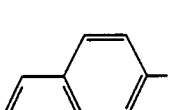 | 0 | COCH₃ | Cl | CF₃ | CF₃ |
| 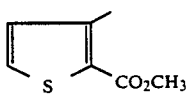 | 1 | COCH₃ | Cl | CF₃ | CF₃ |
| 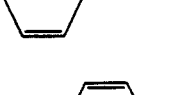 | 0 | H | CN | CF₃ | CF₃ |
| 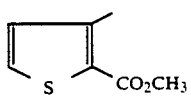 | 1 | H | CN | CF₃ | CF₃ |
| 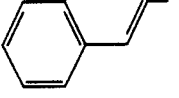 | 0 | CH₃ | CN | CF₃ | CF₃ |
| 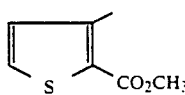 | 1 | CH₃ | CN | CF₃ | CF₃ |
| 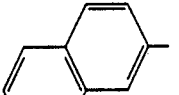 | 0 | COCH₃ | CN | CF₃ | CF₃ |
| 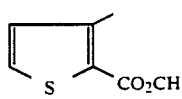 | 1 | COCH₃ | CN | CF₃ | CF₃ |
|  | 0 | H | H | CH₃ | CH₃ |
| 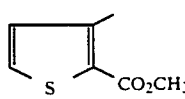 | 1 | H | H | CH₃ | CH₃ |
| 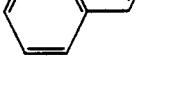 | 0 | CH₃ | H | CH₃ | CH₃ |
| 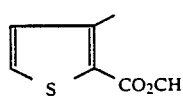 | 1 | CH₃ | H | CH₃ | CH₃ |
| 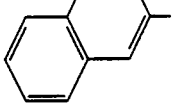 | 0 | COCH₃ | H | CH₃ | CH₃ |
| 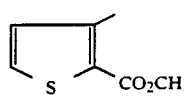 | 1 | COCH₃ | H | CH₃ | CH₃ |
| 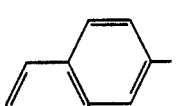 | 0 | H | Cl | CH₃ | CH₃ |
|  | 1 | H | Cl | CH₃ | CH₃ |
| 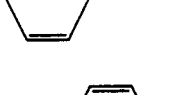 | 0 | CH₃ | Cl | CH₃ | CH₃ |
|  | 1 | CH₃ | Cl | CH₃ | CH₃ |
| 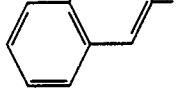 | 0 | COCH₃ | Cl | CH₃ | CH₃ |
| 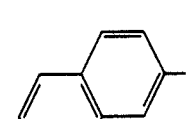 | 1 | COCH₃ | Cl | CH₃ | CH₃ |

| | | | | | |
|---|---|---|---|---|---|
| 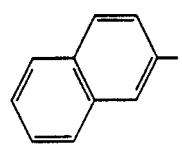 | 0 | H | CN | CH₃ | CH₃ |
| 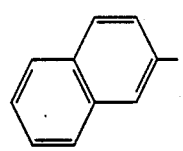 | 1 | H | CN | CH₃ | CH₃ |
| 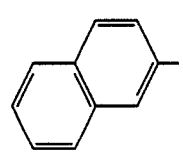 | 0 | CH₃ | CN | CH₃ | CH₃ |
| 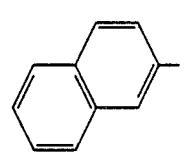 | 1 | CH₃ | CN | CH₃ | CH₃ |
| 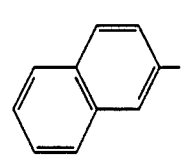 | 0 | COCH₃ | CN | CH₃ | CH₃ |
| 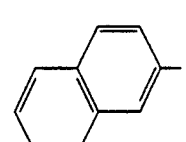 | 1 | COCH₃ | CN | CH₃ | CH₃ |
| 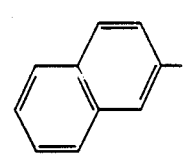 | 0 | H | H | CH₃ | Cl |
| 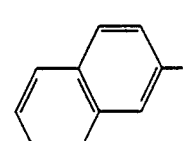 | 1 | H | H | CH₃ | Cl |
| 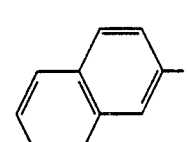 | 0 | CH₃ | H | CH₃ | Cl |
| 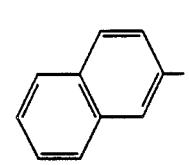 | 1 | CH₃ | H | CH₃ | Cl |
| 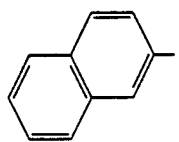 | 0 | COCH₃ | H | CH₃ | Cl |
|  | 1 | COCH₃ | H | CH₃ | Cl |
| 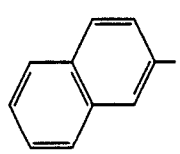 | 0 | H | Cl | CH₃ | Cl |
| 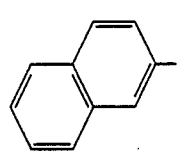 | 1 | H | Cl | CH₃ | Cl |
| 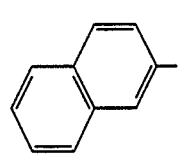 | 0 | CH₃ | Cl | CH₃ | Cl |
| 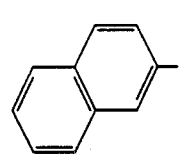 | 1 | CH₃ | Cl | CH₃ | Cl |
| 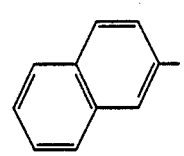 | 0 | COCH₃ | Cl | CH₃ | Cl |
| 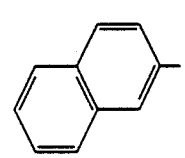 | 0 | COCH₃ | Cl | CH₃ | Cl |
| 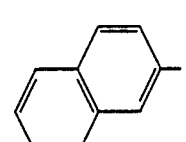 | 0 | H | CN | CH₃ | Cl |
| 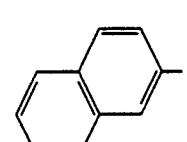 | 1 | H | CN | CH₃ | Cl |

| | | | | | |
|---|---|---|---|---|---|
| 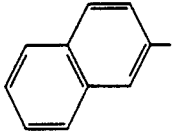 | 0 | CH₃ | CN | CH₃ | Cl |
|  | 1 | CH₃ | CN | CH₃ | Cl |
| 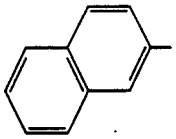 | 0 | COCH₃ | CN | CH₃ | Cl |
|  | 1 | COCH₃ | CN | CH₃ | Cl |
| 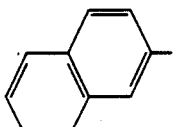 | 0 | H | H | CH₃ | CF₃ |
| 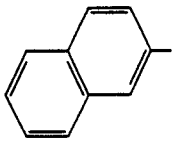 | 1 | H | H | CH₃ | CF₃ |
| 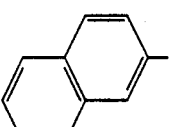 | 0 | CH₃ | H | CH₃ | CF₃ |
| 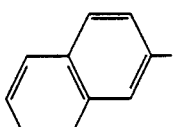 | 1 | CH₃ | H | CH₃ | CF₃ |
| 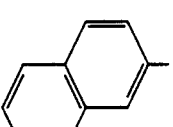 | 0 | COCH₃ | H | CH₃ | CF₃ |
| 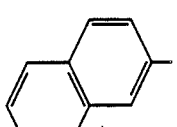 | 1 | COCH₃ | H | CH₃ | CF₃ |
| 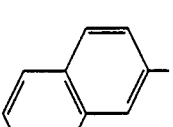 | 0 | H | Cl | CH₃ | CF₃ |
| 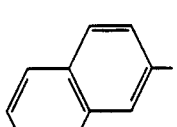 | 1 | H | Cl | CH₃ | CF₃ |
| 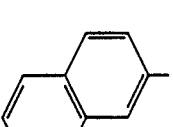 | 0 | CH₃ | Cl | CH₃ | CF₃ |
| 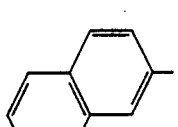 | 1 | CH₃ | Cl | CH₃ | CF₃ |
| 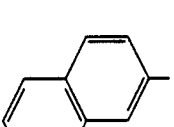 | 0 | COCH₃ | Cl | CH₃ | CF₃ |
| 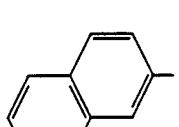 | 1 | COCH₃ | Cl | CH₃ | CF₃ |
| 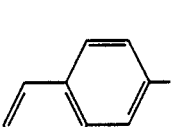 | 0 | H | CN | CH₃ | CF₃ |
| 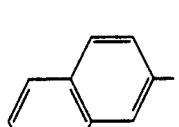 | 1 | H | CN | CH₃ | CF₃ |
| 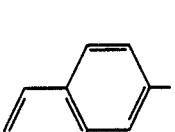 | 0 | CH₃ | CN | CH₃ | CF₃ |
| 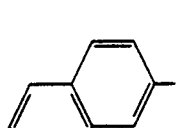 | 1 | CH₃ | CN | CH₃ | CF₃ |

| | | | | | |
|---|---|---|---|---|---|
| 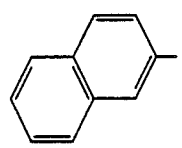 | 0 | COCH$_3$ | CN | CH$_3$ | CF$_3$ |
| 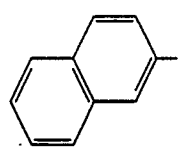 | 1 | COCH$_3$ | CN | CH$_3$ | CF$_3$ |
| 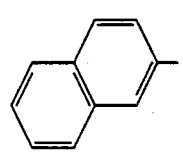 | 0 | H | H | CH$_3$ | OCH$_3$ |
| 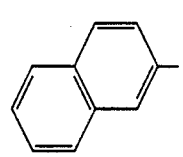 | 1 | H | H | CH$_3$ | OCH$_3$ |
| 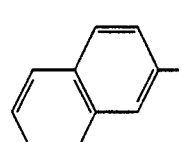 | 0 | CH$_3$ | H | CH$_3$ | OCH$_3$ |
| 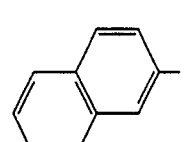 | 1 | CH$_3$ | H | CH$_3$ | OCH$_3$ |
| 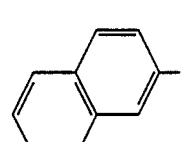 | 0 | COCH$_3$ | H | CH$_3$ | OCH$_3$ |
| 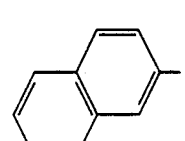 | 1 | COCH$_3$ | H | CH$_3$ | OCH$_3$ |
| 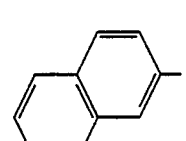 | 0 | H | Cl | CH$_3$ | OCH$_3$ |
| 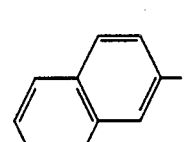 | 1 | H | Cl | CH$_3$ | OCH$_3$ |
| 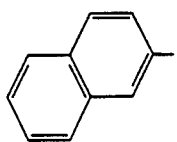 | 0 | CH$_3$ | Cl | CH$_3$ | OCH$_3$ |
|  | 1 | CH$_3$ | Cl | CH$_3$ | OCH$_3$ |
| 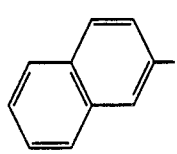 | 0 | COCH$_3$ | Cl | CH$_3$ | OCH$_3$ |
| 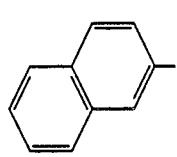 | 1 | COCH$_3$ | Cl | CH$_3$ | OCH$_3$ |
| 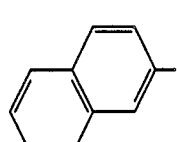 | 0 | H | CN | CH$_3$ | OCH$_3$ |
| 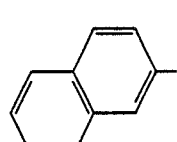 | 1 | H | CN | CH$_3$ | OCH$_3$ |
| 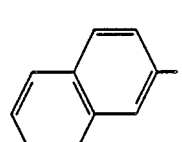 | 0 | CH$_3$ | CN | CH$_3$ | OCH$_3$ |
| 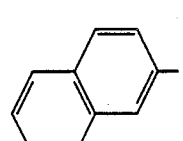 | 1 | CH$_3$ | CN | CH$_3$ | OCH$_3$ |
| 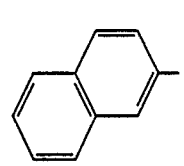 | 0 | COCH$_3$ | CN | CH$_3$ | OCH$_3$ |
| 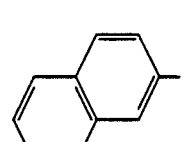 | 1 | COCH$_3$ | CN | CH$_3$ | OCH$_3$ |

| Ar | n | R1 | R2 | R3 | R4 |
|---|---|---|---|---|---|
| 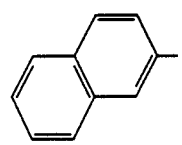 | 0 | H | H | CF3 | CH3 |
| 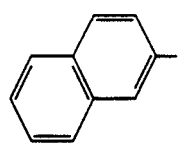 | 1 | H | H | CF3 | CH3 |
| 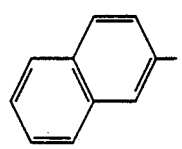 | 0 | CH3 | H | CF3 | CH3 |
| 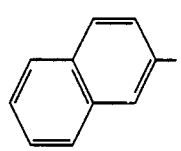 | 1 | CH3 | H | CF3 | CH3 |
| 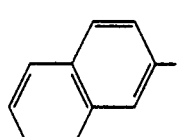 | 0 | COCH3 | H | CF3 | CH3 |
| 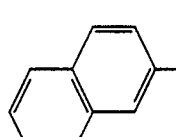 | 1 | COCH3 | H | CF3 | CH3 |
| 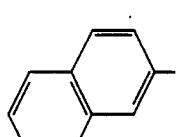 | 0 | H | Cl | CF3 | CH3 |
| 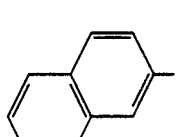 | 1 | H | Cl | CF3 | CH3 |
| 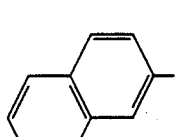 | 0 | CH3 | Cl | CF3 | CH3 |
| 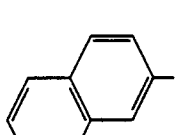 | 1 | CH3 | Cl | CF3 | CH3 |
| 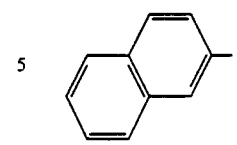 | 0 | COCH3 | Cl | CF3 | CH3 |
| 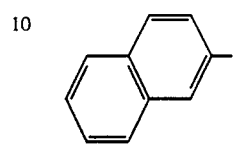 | 1 | COCH3 | Cl | CF3 | CH3 |
| 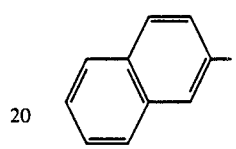 | 0 | H | CN | CF3 | CH3 |
| 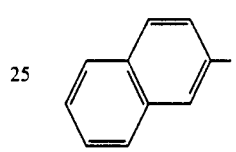 | 1 | H | CN | CF3 | CH3 |
| 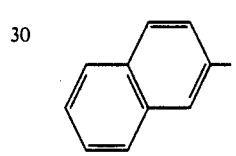 | 0 | CH3 | CN | CF3 | CH3 |
| 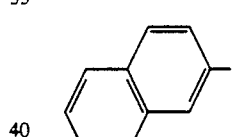 | 1 | CH3 | CN | CF3 | CH3 |
| 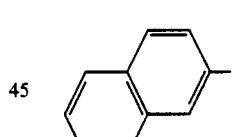 | 0 | COCH3 | CN | CF3 | CH3 |
| 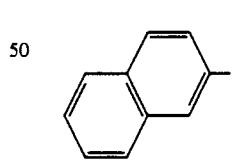 | 1 | COCH3 | CN | CF3 | CH3 |
| 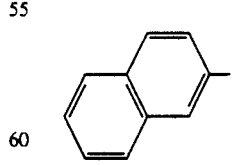 | 0 | H | H | CF3 | CF3 |
| 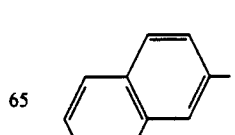 | 1 | H | H | CF3 | CF3 |

-continued
| A | n | R¹ | R² | R⁴ | R⁴'' |
|---|---|---|---|---|---|
|  | 0 | CH₃ | H | CF₃ | CF₃ |
| 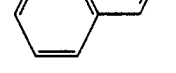 | 1 | CH₃ | H | CF₃ | CF₃ |
|  | 0 | COCH₃ | H | CF₃ | CF₃ |
| 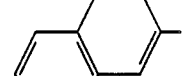 | 1 | COCH₃ | H | CF₃ | CF₃ |
| 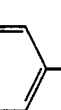 | 0 | H | Cl | CF₃ | CF₃ |
| 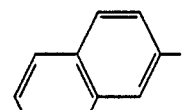 | 1 | H | Cl | CF₃ | CF₃ |
| 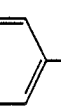 | 0 | CH₃ | Cl | CF₃ | CF₃ |
| 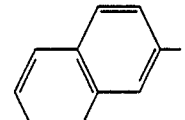 | 1 | CH₃ | Cl | CF₃ | CF₃ |
| 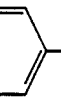 | 0 | COCH₃ | Cl | CF₃ | CF₃ |
| 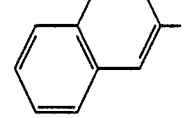 | 1 | COCH₃ | Cl | CF₃ | CF₃ |
-continued
| A | n | R¹ | R² | R⁴ | R⁴'' |
|---|---|---|---|---|---|
| 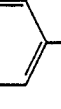 | 0 | H | CN | CF₃ | CF₃ |
| 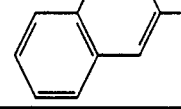 | 1 | H | CN | CF₃ | CF₃ |
| 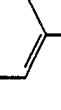 | 0 | CH₃ | CN | CF₃ | CF₃ |
|  | 1 | CH₃ | CN | CF₃ | CF₃ |
|  | 0 | COCH₃ | CN | CF₃ | CF₃ |
| 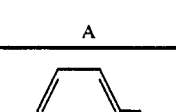 | 1 | COCH₃ | CN | CF₃ | CF₃ |
TABLE II
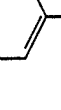
| A | n | R¹ | R² | R⁴ | R⁴'' |
|---|---|---|---|---|---|
|  | 0 | H | H | CH₃ | CH₃ |
|  | 1 | H | H | CH₃ | CH₃ |
|  | 0 | CH₃ | H | CH₃ | CH₃ |

TABLE II-continued

| | | | | | |
|---|---|---|---|---|---|
| 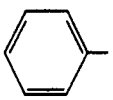 | 1 | CH$_3$ | H | CH$_3$ | CH$_3$ |
| 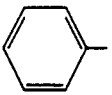 | 0 | COCH$_3$ | H | CH$_3$ | CH$_3$ |
| 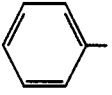 | 1 | COCH$_3$ | H | CH$_3$ | CH$_3$ |
| 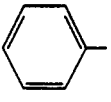 | 0 | H | Cl | CH$_3$ | CH$_3$ |
| 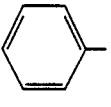 | 1 | H | Cl | CH$_3$ | CH$_3$ |
| 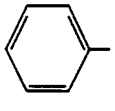 | 0 | CH$_3$ | Cl | CH$_3$ | CH$_3$ |
| 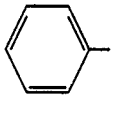 | 1 | CH$_3$ | Cl | CH$_3$ | CH$_3$ |
| 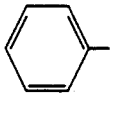 | 0 | COCH$_3$ | Cl | CH$_3$ | CH$_3$ |
| 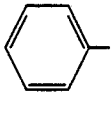 | 1 | COCH$_3$ | Cl | CH$_3$ | CH$_3$ |
| 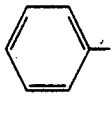 | 0 | H | CN | CH$_3$ | CH$_3$ |
| 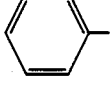 | 1 | H | CN | CH$_3$ | CH$_3$ |
| 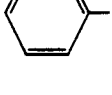 | 0 | CH$_3$ | CN | CH$_3$ | CH$_3$ |
| 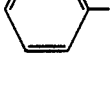 | 1 | CH$_3$ | CN | CH$_3$ | CH$_3$ |

TABLE II-continued

| | | | | | |
|---|---|---|---|---|---|
| 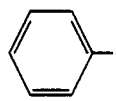 | 0 | COCH$_3$ | CN | CH$_3$ | CH$_3$ |
|  | 1 | COCH$_3$ | CN | CH$_3$ | CH$_3$ |
| 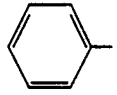 | 0 | H | H | CH$_3$ | Cl |
| 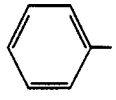 | 1 | H | H | CH$_3$ | Cl |
| 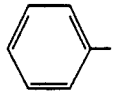 | 0 | CH$_3$ | H | CH$_3$ | Cl |
| 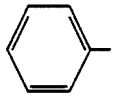 | 1 | CH$_3$ | H | CH$_3$ | Cl |
| 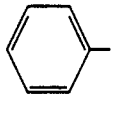 | 0 | COCH$_3$ | H | CH$_3$ | Cl |
| 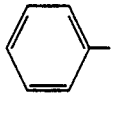 | 1 | COCH$_3$ | H | CH$_3$ | Cl |
| 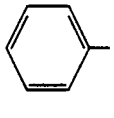 | 0 | H | Cl | CH$_3$ | Cl |
| 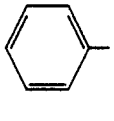 | 1 | H | Cl | CH$_3$ | Cl |
| 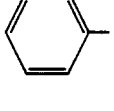 | 0 | CH$_3$ | Cl | CH$_3$ | Cl |
| 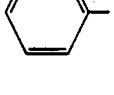 | 1 | CH$_3$ | Cl | CH$_3$ | Cl |
| 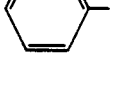 | 0 | COCH$_3$ | Cl | CH$_3$ | Cl |

TABLE II-continued
| | | | | | |
|---|---|---|---|---|---|
| 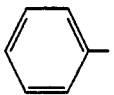 | 1 | COCH₃ | Cl | CH₃ | Cl |
| 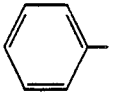 | 0 | H | CN | CH₃ | Cl |
| 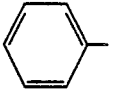 | 1 | H | CN | CH₃ | Cl |
| 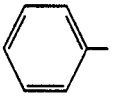 | 0 | CH₃ | CN | CH₃ | Cl |
| 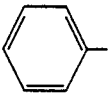 | 1 | CH₃ | CN | CH₃ | Cl |
| 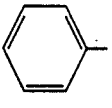 | 0 | COCH₃ | CN | CH₃ | Cl |
| 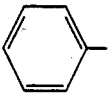 | 1 | COCH₃ | CN | CH₃ | Cl |
| 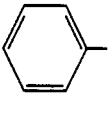 | 0 | H | H | CH₃ | CF₃ |
| 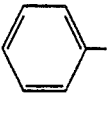 | 1 | H | H | CH₃ | CF₃ |
| 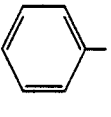 | 0 | CH₃ | H | CH₃ | CF₃ |
| 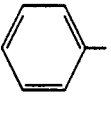 | 1 | CH₃ | H | CH₃ | CF₃ |
| 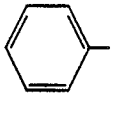 | 0 | COCH₃ | H | CH₃ | CF₃ |
| 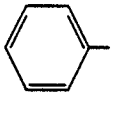 | 1 | COCH₃ | H | CH₃ | CF₃ |
| 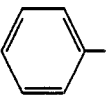 | 0 | H | Cl | CH₃ | CF₃ |
| 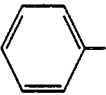 | 1 | H | Cl | CH₃ | CF₃ |
| 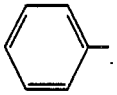 | 0 | CH₃ | Cl | CH₃ | CF₃ |
| 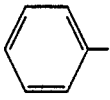 | 1 | CH₃ | Cl | CH₃ | CF₃ |
| 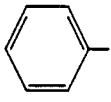 | 0 | COCH₃ | Cl | CH₃ | CF₃ |
| 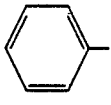 | 1 | COCH₃ | Cl | CH₃ | CF₃ |
| 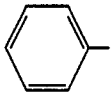 | 0 | H | CN | CH₃ | CF₃ |
| 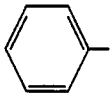 | 1 | H | CN | CH₃ | CF₃ |
| 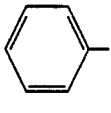 | 0 | CH₃ | CN | CH₃ | CF₃ |
| 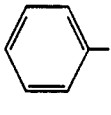 | 1 | CH₃ | CN | CH₃ | CF₃ |
|  | 0 | COCH₃ | CN | CH₃ | CF₃ |
|  | 1 | COCH₃ | CN | CH₃ | CF₃ |
|  | 0 | H | H | CH₃ | OCH₃ |

TABLE II-continued

| Ar | n | R1 | R2 | R3 | R4 |
|---|---|---|---|---|---|
|  | 1 | H | H | CH₃ | OCH₃ |
|  | 0 | CH₃ | H | CH₃ | OCH₃ |
|  | 1 | CH₃ | H | CH₃ | OCH₃ |
|  | 0 | COCH₃ | H | CH₃ | OCH₃ |
|  | 1 | COCH₃ | H | CH₃ | OCH₃ |
|  | 0 | H | Cl | CH₃ | OCH₃ |
|  | 1 | H | Cl | CH₃ | OCH₃ |
|  | 0 | CH₃ | Cl | CH₃ | OCH₃ |
|  | 1 | CH₃ | Cl | CH₃ | OCH₃ |
|  | 0 | COCH₃ | Cl | CH₃ | OCH₃ |
|  | 1 | COCH₃ | Cl | CH₃ | OCH₃ |
|  | 0 | H | CN | CH₃ | OCH₃ |
|  | 1 | H | CN | CH₃ | OCH₃ |
|  | 0 | CH₃ | CN | CH₃ | OCH₃ |
|  | 1 | CH₃ | CN | CH₃ | OCH₃ |
|  | 0 | COCH₃ | CN | CH₃ | OCH₃ |
|  | 1 | COCH₃ | CN | CH₃ | OCH₃ |
|  | 0 | H | H | CF₃ | CH₃ |
|  | 1 | H | H | CF₃ | CH₃ |
|  | 0 | CH₃ | H | CF₃ | CH₃ |
|  | 1 | CH₃ | H | CF₃ | CH₃ |
|  | 0 | COCH₃ | H | CF₃ | CH₃ |
|  | 1 | COCH₃ | H | CF₃ | CH₃ |
|  | 0 | H | Cl | CF₃ | CH₃ |
|  | 1 | H | Cl | CF₃ | CH₃ |
|  | 0 | CH₃ | Cl | CF₃ | CH₃ |

TABLE II-continued

| | | | | | |
|---|---|---|---|---|---|
| 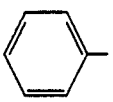 | 1 | CH₃ | Cl | CF₃ | CH₃ |
| 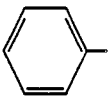 | 0 | COCH₃ | Cl | CF₃ | CH₃ |
| 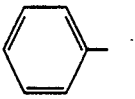 | 1 | COCH₃ | Cl | CF₃ | CH₃ |
| 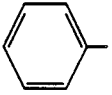 | 0 | H | CN | CF₃ | CH₃ |
| 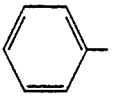 | 1 | H | CN | CF₃ | CH₃ |
| 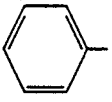 | 0 | CH₃ | CN | CF₃ | CH₃ |
| 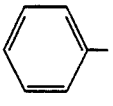 | 1 | CH₃ | CN | CF₃ | CH₃ |
| 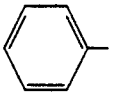 | 0 | COCH₃ | CN | CF₃ | CH₃ |
| 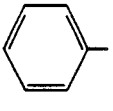 | 1 | COCH₃ | CN | CF₃ | CH₃ |
| 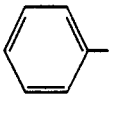 | 0 | H | H | CF₃ | CF₃ |
| 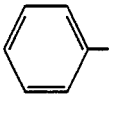 | 1 | H | H | CF₃ | CF₃ |
| 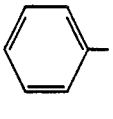 | 0 | CH₃ | H | CF₃ | CF₃ |
| 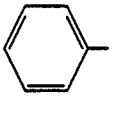 | 1 | CH₃ | H | CF₃ | CF₃ |

TABLE II-continued

| | | | | | |
|---|---|---|---|---|---|
| 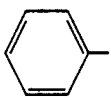 | 0 | COCH₃ | H | CF₃ | CF₃ |
| 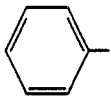 | 1 | COCH₃ | H | CF₃ | CF₃ |
| 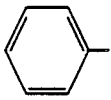 | 0 | H | Cl | CF₃ | CF₃ |
| 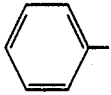 | 1 | H | Cl | CF₃ | CF₃ |
| 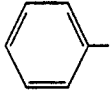 | 0 | CH₃ | Cl | CF₃ | CF₃ |
| 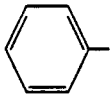 | 1 | CH₃ | Cl | CF₃ | CF₃ |
| 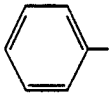 | 0 | COCH₃ | Cl | CF₃ | CF₃ |
| 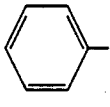 | 1 | COCH₃ | Cl | CF₃ | CF₃ |
| 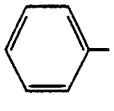 | 0 | H | CN | CF₃ | CF₃ |
| 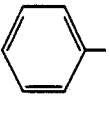 | 1 | H | CN | CF₃ | CF₃ |
| 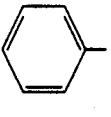 | 0 | CH₃ | CN | CF₃ | CF₃ |
| 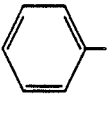 | 1 | CH₃ | CN | CF₃ | CF₃ |
| 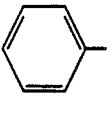 | 0 | COCH₃ | CN | CF₃ | CF₃ |

TABLE II-continued

| Ar | n | R1 | R2 | R3 | R4 |
|---|---|---|---|---|---|
| phenyl | 0 | COCH₃ | CN | CF₃ | CF₃ |
| 3-F, 2-CO₂CH₃-phenyl | 0 | H | H | CH₃ | CH₃ |
| 3-F, 2-CO₂CH₃-phenyl | 1 | H | H | CH₃ | CH₃ |
| 3-F, 2-CO₂CH₃-phenyl | 0 | CH₃ | H | CH₃ | CH₃ |
| 3-F, 2-CO₂CH₃-phenyl | 1 | CH₃ | H | CH₃ | CH₃ |
| 3-F, 2-CO₂CH₃-phenyl | 0 | COCH₃ | H | CH₃ | CH₃ |
| 3-F, 2-CO₂CH₃-phenyl | 1 | COCH₃ | H | CH₃ | CH₃ |
| 3-F, 2-CO₂CH₃-phenyl | 0 | H | Cl | CH₃ | CH₃ |
| 3-F, 2-CO₂CH₃-phenyl | 1 | H | Cl | CH₃ | CH₃ |
| 3-F, 2-CO₂CH₃-phenyl | 0 | CH₃ | Cl | CH₃ | CH₃ |
| 3-F, 2-CO₂CH₃-phenyl | 1 | CH₃ | Cl | CH₃ | CH₃ |
| 3-F, 2-CO₂CH₃-phenyl | 0 | COCH₃ | Cl | CH₃ | CH₃ |
| 3-F, 2-CO₂CH₃-phenyl | 1 | COCH₃ | Cl | CH₃ | CH₃ |
| 3-F, 2-CO₂CH₃-phenyl | 0 | H | CN | CH₃ | CH₃ |
| 3-F, 2-CO₂CH₃-phenyl | 1 | H | CN | CH₃ | CH₃ |
| 3-F, 2-CO₂CH₃-phenyl | 0 | CH₃ | CN | CH₃ | CH₃ |
| 3-F, 2-CO₂CH₃-phenyl | 1 | CH₃ | CN | CH₃ | CH₃ |
| 3-F, 2-CO₂CH₃-phenyl | 0 | COCH₃ | CN | CH₃ | CH₃ |

TABLE II-continued
| Structure | | | | | |
|---|---|---|---|---|---|
| 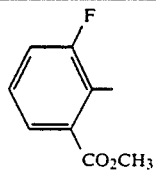 | 1 | COCH₃ | CN | CH₃ | CH₃ |
| 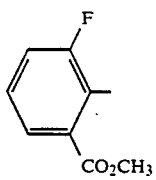 | 0 | H | H | CH₃ | Cl |
| 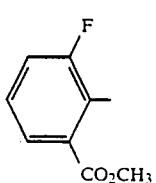 | 1 | H | H | CH₃ | Cl |
| 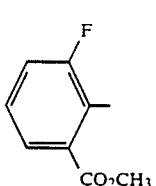 | 0 | CH₃ | H | CH₃ | Cl |
| 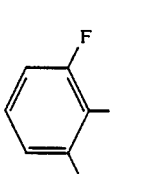 | 1 | CH₃ | H | CH₃ | Cl |
| 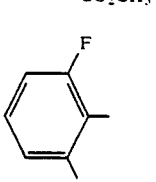 | 0 | COCH₃ | H | CH₃ | Cl |
| 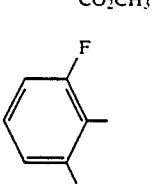 | 1 | COCH₃ | H | CH₃ | Cl |
| 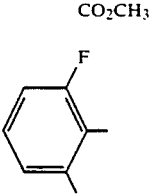 | 0 | H | Cl | CH₃ | Cl |
|  | 1 | H | Cl | CH₃ | Cl |
TABLE II-continued
| Structure | | | | | |
|---|---|---|---|---|---|
| 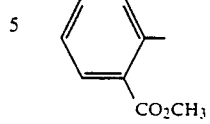 | 0 | CH₃ | Cl | CH₃ | Cl |
| 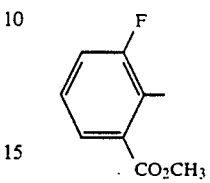 | 1 | CH₃ | Cl | CH₃ | Cl |
| 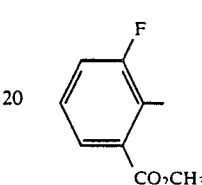 | 0 | COCH₃ | Cl | CH₃ | Cl |
| 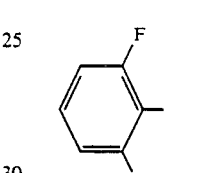 | 1 | COCH₃ | Cl | CH₃ | Cl |
| 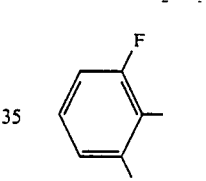 | 0 | H | CN | CH₃ | Cl |
| 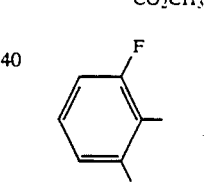 | 1 | H | CN | CH₃ | Cl |
| 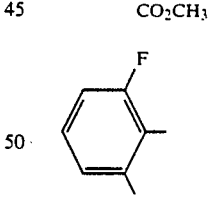 | 0 | CH₃ | CN | CH₃ | Cl |
| 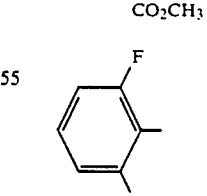 | 1 | CH₃ | CN | CH₃ | Cl |
| 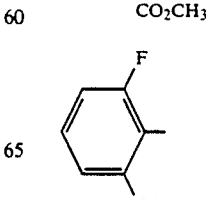 | 0 | COCH₃ | CN | CH₃ | Cl |

TABLE II-continued

| Ar | n | R1 | R2 | R3 | R4 |
|---|---|---|---|---|---|
| 3-F-2-(CO2CH3)-phenyl | 1 | COCH3 | CN | CH3 | Cl |
| 3-F-2-(CO2CH3)-phenyl | 0 | H | H | CH3 | CF3 |
| 3-F-2-(CO2CH3)-phenyl | 1 | H | H | CH3 | CF3 |
| 3-F-2-(CO2CH3)-phenyl | 0 | CH3 | H | CH3 | CF3 |
| 3-F-2-(CO2CH3)-phenyl | 1 | CH3 | H | CH3 | CF3 |
| 3-F-2-(CO2CH3)-phenyl | 0 | COCH3 | H | CH3 | CF3 |
| 3-F-2-(CO2CH3)-phenyl | 1 | COCH3 | H | CH3 | CF3 |
| 3-F-2-(CO2CH3)-phenyl | 0 | H | Cl | CH3 | CF3 |
| 3-F-2-(CO2CH3)-phenyl | 1 | H | Cl | CH3 | CF3 |
| 3-F-2-(CO2CH3)-phenyl | 0 | CH3 | Cl | CH3 | CF3 |
| 3-F-2-(CO2CH3)-phenyl | 1 | CH3 | Cl | CH3 | CF3 |
| 3-F-2-(CO2CH3)-phenyl | 0 | COCH3 | Cl | CH3 | CF3 |
| 3-F-2-(CO2CH3)-phenyl | 1 | COCH3 | Cl | CH3 | CF3 |
| 3-F-2-(CO2CH3)-phenyl | 0 | H | CN | CH3 | CF3 |
| 3-F-2-(CO2CH3)-phenyl | 1 | H | CN | CH3 | CF3 |
| 3-F-2-(CO2CH3)-phenyl | 0 | CH3 | CN | CH3 | CF3 |
| 3-F-2-(CO2CH3)-phenyl | 1 | CH3 | CN | CH3 | CF3 |

| | | | | | |
|---|---|---|---|---|---|
| 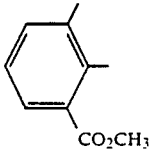 | 0 | COCH3 | CN | CH3 | CF3 |
| 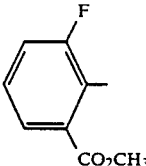 | 1 | COCH3 | CN | CH3 | CF3 |
| 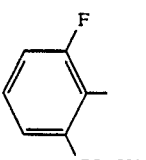 | 0 | H | H | CH3 | OCH3 |
| 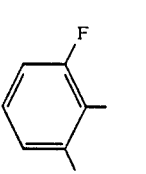 | 1 | H | H | CH3 | OCH3 |
| 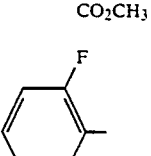 | 0 | CH3 | H | CH3 | OCH3 |
| 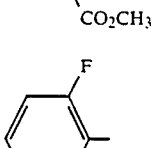 | 1 | CH3 | H | CH3 | OCH3 |
| 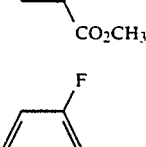 | 0 | COCH3 | H | CH3 | OCH3 |
| 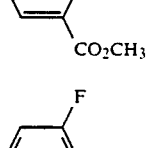 | 1 | COCH3 | H | CH3 | OCH3 |
| 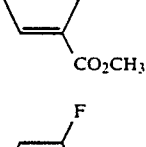 | 0 | H | Cl | CH3 | OCH3 |
| 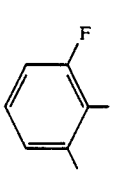 | 1 | H | Cl | CH3 | OCH3 |
| 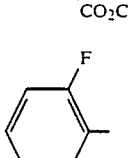 | 0 | CH3 | Cl | CH3 | OCH3 |
| 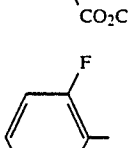 | 1 | CH3 | Cl | CH3 | OCH3 |
| 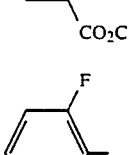 | 0 | COCH3 | Cl | CH3 | OCH3 |
| 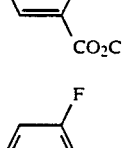 | 1 | COCH3 | Cl | CH3 | OCH3 |
| 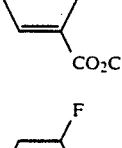 | 0 | H | CN | CH3 | OCH3 |
| 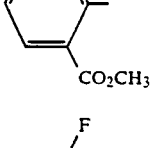 | 1 | H | CN | CH3 | OCH3 |
| 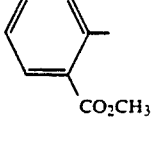 | 0 | CH3 | CN | CH3 | OCH3 |
|  | 1 | CH3 | CN | CH3 | OCH3 |

| | | | | | | | | | | |
|---|---|---|---|---|---|---|---|---|---|---|
| 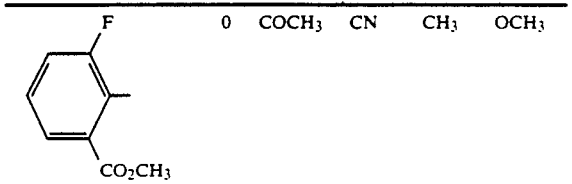 | 0 | COCH$_3$ | CN | CH$_3$ | OCH$_3$ | 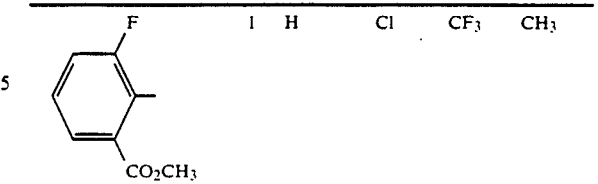 | 1 | H | Cl | CF$_3$ | CH$_3$ |
| 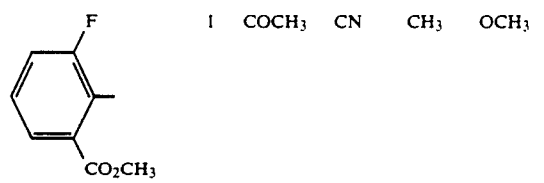 | 1 | COCH$_3$ | CN | CH$_3$ | OCH$_3$ | 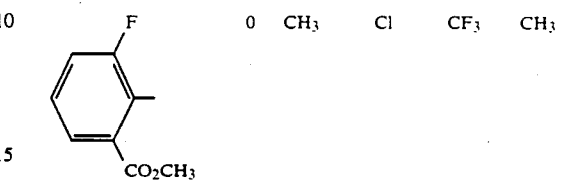 | 0 | CH$_3$ | Cl | CF$_3$ | CH$_3$ |
| 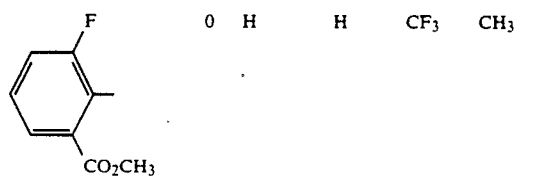 | 0 | H | H | CF$_3$ | CH$_3$ | 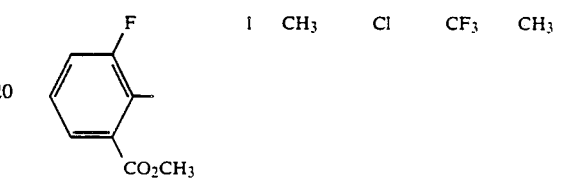 | 1 | CH$_3$ | Cl | CF$_3$ | CH$_3$ |
| 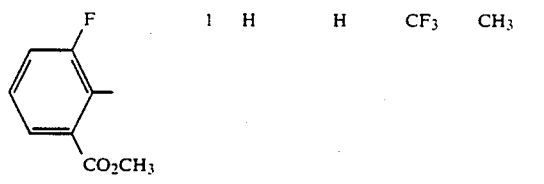 | 1 | H | H | CF$_3$ | CH$_3$ | 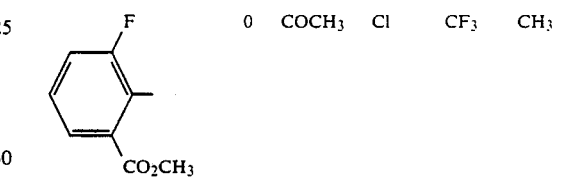 | 0 | COCH$_3$ | Cl | CF$_3$ | CH$_3$ |
| 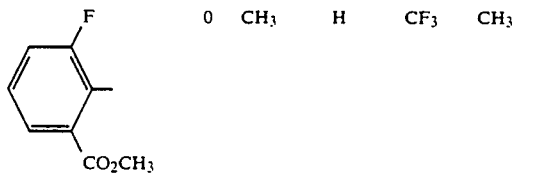 | 0 | CH$_3$ | H | CF$_3$ | CH$_3$ | 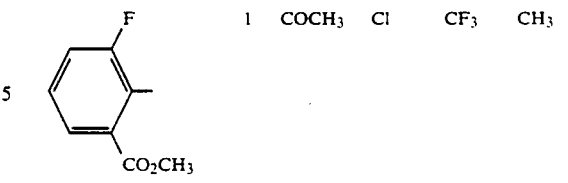 | 1 | COCH$_3$ | Cl | CF$_3$ | CH$_3$ |
| 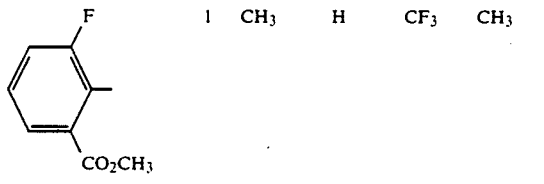 | 1 | CH$_3$ | H | CF$_3$ | CH$_3$ | 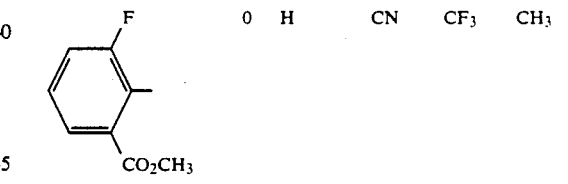 | 0 | H | CN | CF$_3$ | CH$_3$ |
| 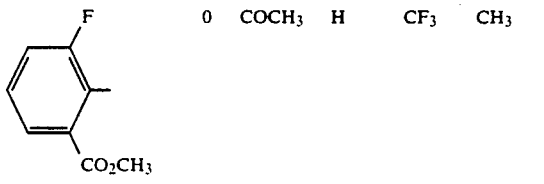 | 0 | COCH$_3$ | H | CF$_3$ | CH$_3$ | 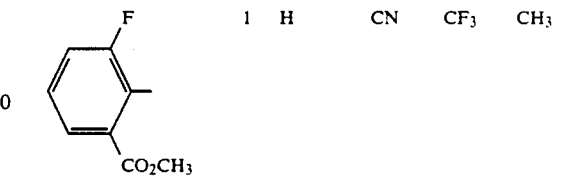 | 1 | H | CN | CF$_3$ | CH$_3$ |
| 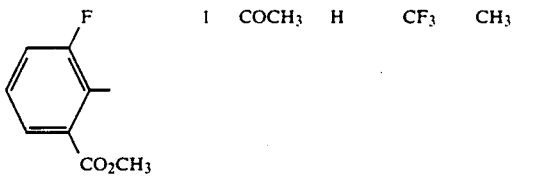 | 1 | COCH$_3$ | H | CF$_3$ | CH$_3$ | 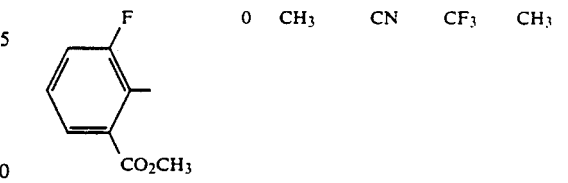 | 0 | CH$_3$ | CN | CF$_3$ | CH$_3$ |
| 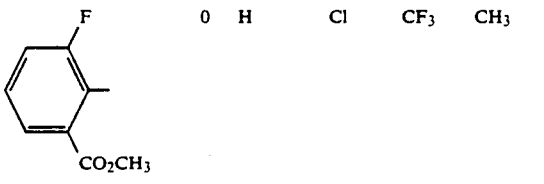 | 0 | H | Cl | CF$_3$ | CH$_3$ | 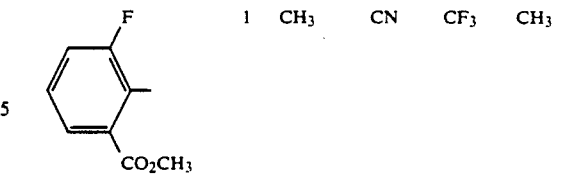 | 1 | CH$_3$ | CN | CF$_3$ | CH$_3$ |

-continued
| Ar | n | R | X | Y | Z |
|---|---|---|---|---|---|
| 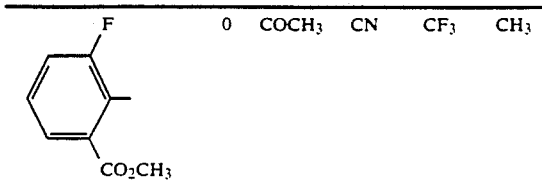 | 0 | COCH₃ | CN | CF₃ | CH₃ |
| 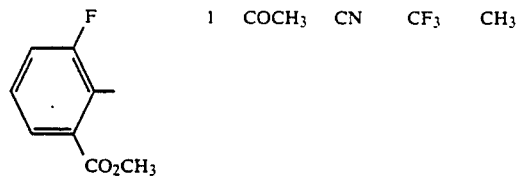 | 1 | COCH₃ | CN | CF₃ | CH₃ |
| 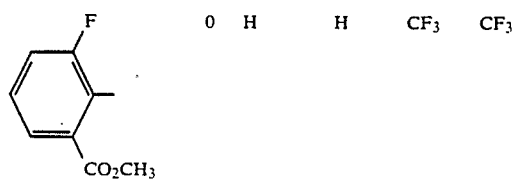 | 0 | H | H | CF₃ | CF₃ |
| 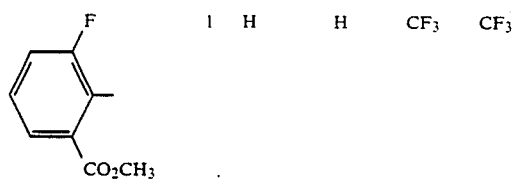 | 1 | H | H | CF₃ | CF₃ |
| 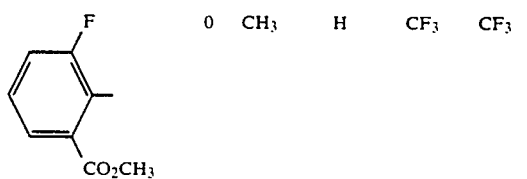 | 0 | CH₃ | H | CF₃ | CF₃ |
| 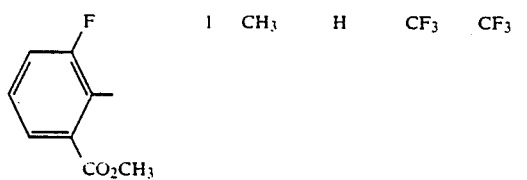 | 1 | CH₃ | H | CF₃ | CF₃ |
| 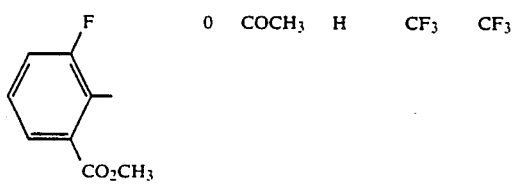 | 0 | COCH₃ | H | CF₃ | CF₃ |
| 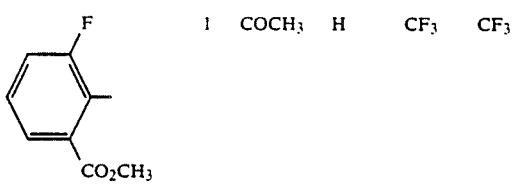 | 1 | COCH₃ | H | CF₃ | CF₃ |
| 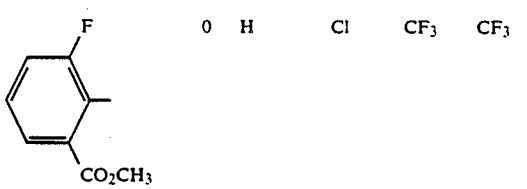 | 0 | H | Cl | CF₃ | CF₃ |
-continued
| Ar | n | R | X | Y | Z |
|---|---|---|---|---|---|
| 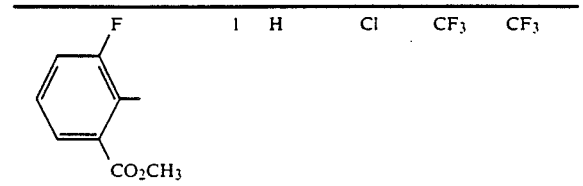 | 1 | H | Cl | CF₃ | CF₃ |
| 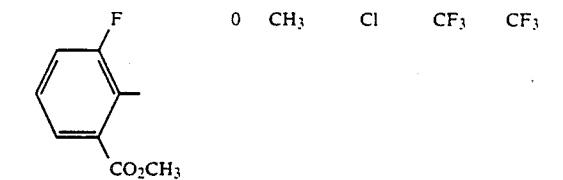 | 0 | CH₃ | Cl | CF₃ | CF₃ |
| 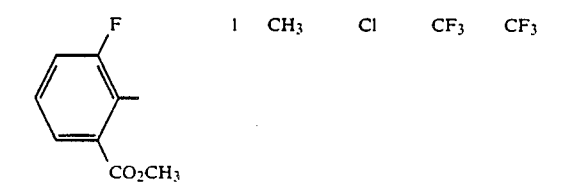 | 1 | CH₃ | Cl | CF₃ | CF₃ |
| 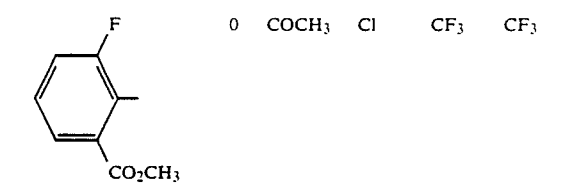 | 0 | COCH₃ | Cl | CF₃ | CF₃ |
| 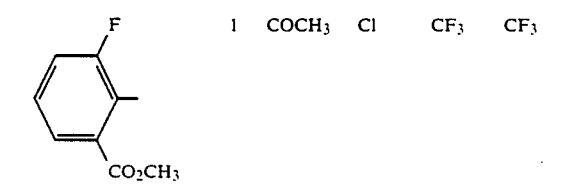 | 1 | COCH₃ | Cl | CF₃ | CF₃ |
| 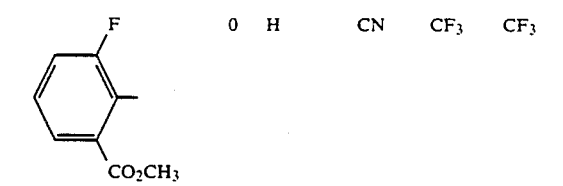 | 0 | H | CN | CF₃ | CF₃ |
| 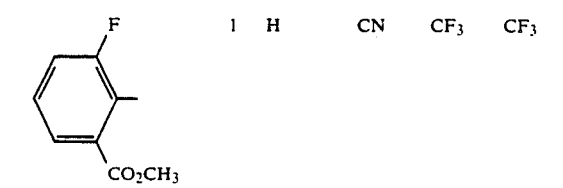 | 1 | H | CN | CF₃ | CF₃ |
| 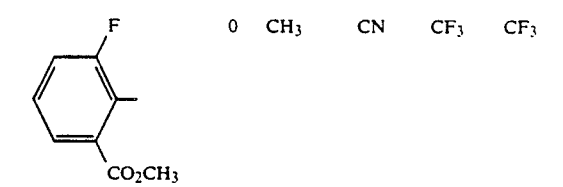 | 0 | CH₃ | CN | CF₃ | CF₃ |
| 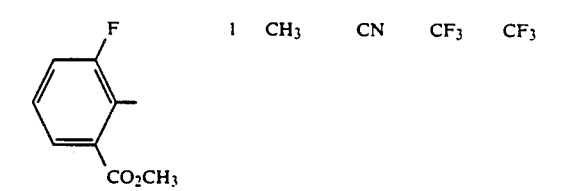 | 1 | CH₃ | CN | CF₃ | CF₃ |

| Structure | n | | | | |
|---|---|---|---|---|---|
| 3-fluoro-2-methyl-6-(CO2CH3) phenyl | 0 | COCH3 | CN | CF3 | CF3 |
| 3-fluoro-2-methyl-6-(CO2CH3) phenyl | 1 | COCH3 | CN | CF3 | CF3 |
| 3-methyl-2-(CO2CH3) thienyl | 0 | H | H | CH3 | CH3 |
| 3-methyl-2-(CO2CH3) thienyl | 1 | H | H | CH3 | CH3 |
| 3-methyl-2-(CO2CH3) thienyl | 0 | CH3 | H | CH3 | CH3 |
| 3-methyl-2-(CO2CH3) thienyl | 1 | CH3 | H | CH3 | CH3 |
| 3-methyl-2-(CO2CH3) thienyl | 0 | COCH3 | H | CH3 | CH3 |
| 3-methyl-2-(CO2CH3) thienyl | 1 | COCH3 | H | CH3 | CH3 |
| 3-methyl-2-(CO2CH3) thienyl | 0 | H | Cl | CH3 | CH3 |
| 3-methyl-2-(CO2CH3) thienyl | 1 | H | Cl | CH3 | CH3 |
| 3-methyl-2-(CO2CH3) thienyl | 0 | CH3 | Cl | CH3 | CH3 |
| 3-methyl-2-(CO2CH3) thienyl | 1 | CH3 | Cl | CH3 | CH3 |
| 3-methyl-2-(CO2CH3) thienyl | 0 | COCH3 | Cl | CH3 | CH3 |
| 3-methyl-2-(CO2CH3) thienyl | 1 | COCH3 | Cl | CH3 | CH3 |
| 3-methyl-2-(CO2CH3) thienyl | 0 | H | CN | CH3 | CH3 |
| 3-methyl-2-(CO2CH3) thienyl | 1 | H | CN | CH3 | CH3 |
| 3-methyl-2-(CO2CH3) thienyl | 0 | CH3 | CN | CH3 | CH3 |
| 3-methyl-2-(CO2CH3) thienyl | 1 | CH3 | CN | CH3 | CH3 |
| 3-methyl-2-(CO2CH3) thienyl | 0 | COCH3 | CN | CH3 | CH3 |
| 3-methyl-2-(CO2CH3) thienyl | 1 | COCH3 | CN | CH3 | CH3 |
| 3-methyl-2-(CO2CH3) thienyl | 0 | H | H | CH3 | Cl |
| 3-methyl-2-(CO2CH3) thienyl | 1 | H | H | CH3 | Cl |
| 3-methyl-2-(CO2CH3) thienyl | 0 | CH3 | H | CH3 | Cl |
| 3-methyl-2-(CO2CH3) thienyl | 1 | CH3 | H | CH3 | Cl |
| 3-methyl-2-(CO2CH3) thienyl | 0 | COCH3 | H | CH3 | Cl |
| 3-methyl-2-(CO2CH3) thienyl | 1 | COCH3 | H | CH3 | Cl |
| 3-methyl-2-(CO2CH3) thienyl | 0 | H | Cl | CH3 | Cl |

| | | | | | | | | | | |
|---|---|---|---|---|---|---|---|---|---|---|
| 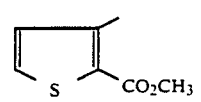 | 1 | H | Cl | CH$_3$ | Cl | 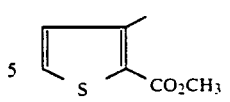 | 1 | CH$_3$ | H | CH$_3$ | CF$_3$ |
| 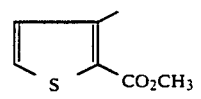 | 0 | CH$_3$ | Cl | CH$_3$ | Cl | 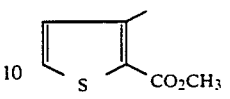 | 0 | COCH$_3$ | H | CH$_3$ | CF$_3$ |
| 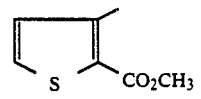 | 1 | CH$_3$ | Cl | CH$_3$ | Cl | 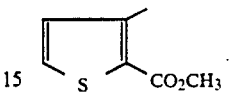 | 1 | COCH$_3$ | H | CH$_3$ | CF$_3$ |
| 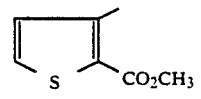 | 0 | COCH$_3$ | Cl | CH$_3$ | Cl | 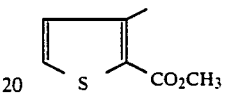 | 0 | H | Cl | CH$_3$ | CF$_3$ |
| 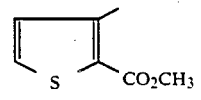 | 1 | COCH$_3$ | Cl | CH$_3$ | Cl | 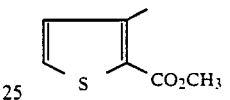 | 1 | H | Cl | CH$_3$ | CF$_3$ |
| 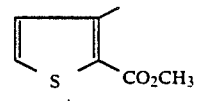 | 0 | H | CN | CH$_3$ | Cl | 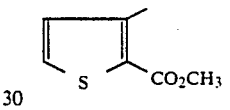 | 0 | CH$_3$ | Cl | CH$_3$ | CF$_3$ |
| 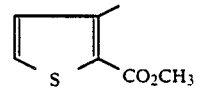 | 1 | H | CN | CH$_3$ | Cl | 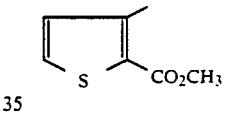 | 1 | CH$_3$ | Cl | CH$_3$ | CF$_3$ |
| 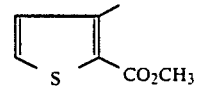 | 0 | CH$_3$ | CN | CH$_3$ | Cl | 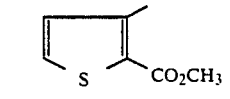 | 0 | COCH$_3$ | Cl | CH$_3$ | CF$_3$ |
| 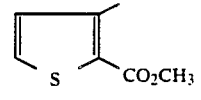 | 1 | CH$_3$ | CN | CH$_3$ | Cl | 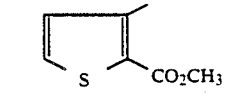 | 1 | COCH$_3$ | Cl | CH$_3$ | CF$_3$ |
| 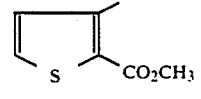 | 0 | COCH$_3$ | CN | CH$_3$ | Cl | 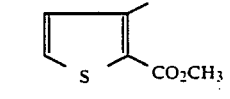 | 0 | H | CN | CH$_3$ | CF$_3$ |
| 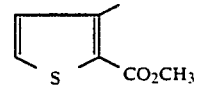 | 1 | COCH$_3$ | CN | CH$_3$ | Cl | 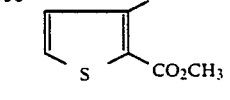 | 1 | H | CN | CH$_3$ | CF$_3$ |
| 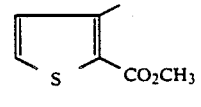 | 0 | H | H | CH$_3$ | CF$_3$ | 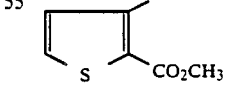 | 0 | CH$_3$ | CN | CH$_3$ | CF$_3$ |
| 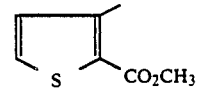 | 1 | H | H | CH$_3$ | CF$_3$ | 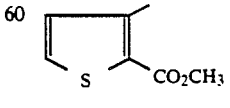 | 1 | CH$_3$ | CN | CH$_3$ | CF$_3$ |
| | 0 | CH$_3$ | H | CH$_3$ | CF$_3$ | | 0 | COCH$_3$ | CN | CH$_3$ | CF$_3$ |

-continued

| Structure | n | | | | |
|---|---|---|---|---|---|
| thiophene-2-CO2CH3 | 1 | COCH3 | CN | CH3 | CF3 |
| thiophene-2-CO2CH3 | 0 | H | H | CH3 | OCH3 |
| thiophene-2-CO2CH3 | 1 | H | H | CH3 | OCH3 |
| thiophene-2-CO2CH3 | 0 | CH3 | H | CH3 | OCH3 |
| thiophene-2-CO2CH3 | 1 | CH3 | H | CH3 | OCH3 |
| thiophene-2-CO2CH3 | 0 | COCH3 | H | CH3 | OCH3 |
| thiophene-2-CO2CH3 | 1 | COCH3 | H | CH3 | OCH3 |
| thiophene-2-CO2CH3 | 0 | H | Cl | CH3 | OCH3 |
| thiophene-2-CO2CH3 | 1 | H | Cl | CH3 | OCH3 |
| thiophene-2-CO2CH3 | 0 | CH3 | Cl | CH3 | OCH3 |
| thiophene-2-CO2CH3 | 1 | CH3 | Cl | CH3 | OCH3 |
| thiophene-2-CO2CH3 | 0 | COCH3 | Cl | CH3 | OCH3 |
| thiophene-2-CO2CH3 | 1 | COCH3 | Cl | CH3 | OCH3 |
| thiophene-2-CO2CH3 | 0 | H | CN | CH3 | OCH3 |
| thiophene-2-CO2CH3 | 1 | H | CN | CH3 | OCH3 |
| thiophene-2-CO2CH3 | 0 | CH3 | CN | CH3 | OCH3 |
| thiophene-2-CO2CH3 | 1 | CH3 | CN | CH3 | OCH3 |
| thiophene-2-CO2CH3 | 0 | COCH3 | CN | CH3 | OCH3 |
| thiophene-2-CO2CH3 | 1 | COCH3 | CN | CH3 | OCH3 |
| thiophene-2-CO2CH3 | 0 | H | H | CF3 | CH3 |
| thiophene-2-CO2CH3 | 1 | H | H | CF3 | CH3 |
| thiophene-2-CO2CH3 | 0 | CH3 | H | CF3 | CH3 |
| thiophene-2-CO2CH3 | 1 | CH3 | H | CF3 | CH3 |
| thiophene-2-CO2CH3 | 0 | COCH3 | H | CF3 | CH3 |
| thiophene-2-CO2CH3 | 1 | COCH3 | H | CF3 | CH3 |
| thiophene-2-CO2CH3 | 0 | H | Cl | CF3 | CH3 |
| thiophene-2-CO2CH3 | 1 | H | Cl | CF3 | CH3 |
| thiophene-2-CO2CH3 | 0 | CH3 | Cl | CF3 | CH3 |

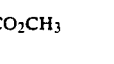
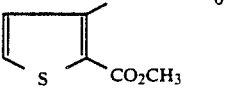
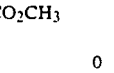
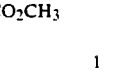
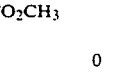
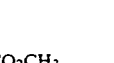
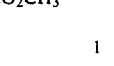
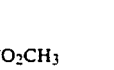
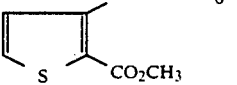
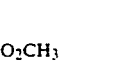

| | | | | | | | | | | |
|---|---|---|---|---|---|---|---|---|---|---|
| 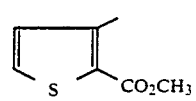 | 1 | CH₃ | Cl | CF₃ | CH₃ | 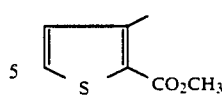 | 1 | COCH₃ | H | CF₃ | CF₃ |
| 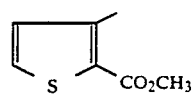 | 0 | COCH₃ | Cl | CF₃ | CH₃ | 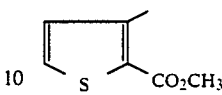 | 0 | H | Cl | CF₃ | CF₃ |
| 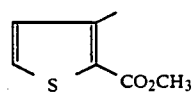 | 1 | COCH₃ | Cl | CF₃ | CH₃ | 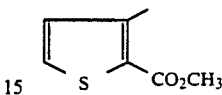 | 1 | H | Cl | CF₃ | CF₃ |
| 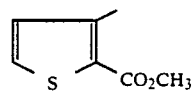 | 0 | H | CN | CF₃ | CH₃ | 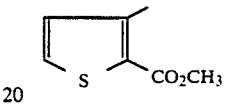 | 0 | CH₃ | Cl | CF₃ | CF₃ |
| 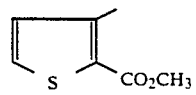 | 1 | H | CN | CF₃ | CH₃ | 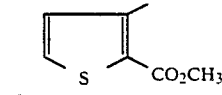 | 1 | CH₃ | Cl | CF₃ | CF₃ |
| 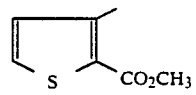 | 0 | CH₃ | CN | CF₃ | CH₃ | 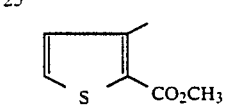 | 0 | COCH₃ | Cl | CF₃ | CF₃ |
| 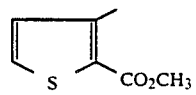 | 1 | CH₃ | CN | CF₃ | CH₃ | 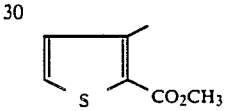 | 1 | COCH₃ | Cl | CF₃ | CF₃ |
| 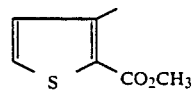 | 0 | COCH₃ | CN | CF₃ | CH₃ | 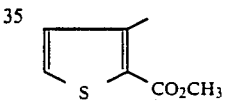 | 0 | H | CN | CF₃ | CF₃ |
| 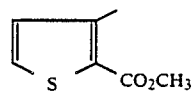 | 1 | COCH₃ | CN | CF₃ | CH₃ | 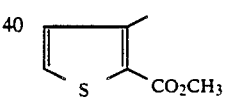 | 1 | H | CN | CF₃ | CF₃ |
| 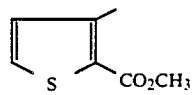 | 0 | H | H | CF₃ | CF₃ | 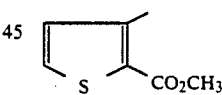 | 0 | CH₃ | CN | CF₃ | CF₃ |
| 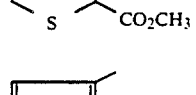 | 1 | H | H | CF₃ | CF₃ | 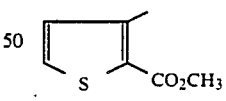 | 1 | CH₃ | CN | CF₃ | CF₃ |
| 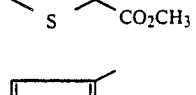 | 0 | CH₃ | H | CF₃ | CF₃ | 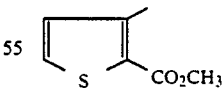 | 0 | COCH₃ | CN | CF₃ | CF₃ |
| 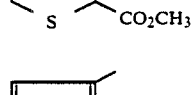 | 1 | CH₃ | H | CF₃ | CF₃ | 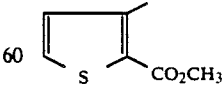 | 1 | COCH₃ | CN | CF₃ | CF₃ |
| 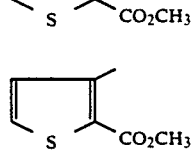 | 0 | COCH₃ | H | CF₃ | CF₃ | 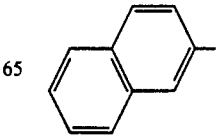 | 0 | H | H | CH₃ | CH₃ |

77
-continued
| | | | | | |
|---|---|---|---|---|---|
| 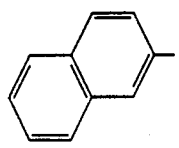 | 1 | H | H | CH₃ | CH₃ |
| 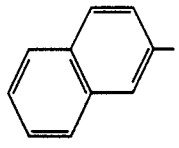 | 0 | CH₃ | H | CH₃ | CH₃ |
| 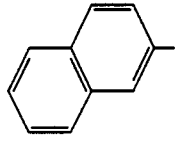 | 1 | CH₃ | H | CH₃ | CH₃ |
| 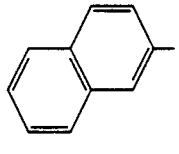 | 0 | COCH₃ | H | CH₃ | CH₃ |
| 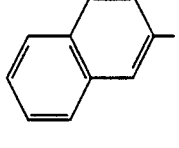 | 1 | COCH₃ | H | CH₃ | CH₃ |
| 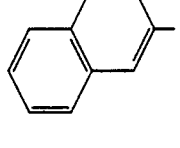 | 0 | H | Cl | CH₃ | CH₃ |
| 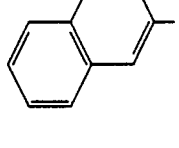 | 1 | H | Cl | CH₃ | CH₃ |
| 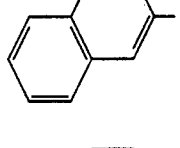 | 0 | CH₃ | Cl | CH₃ | CH₃ |
| 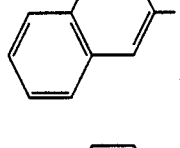 | 1 | CH₃ | Cl | CH₃ | CH₃ |
| 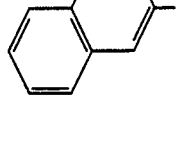 | 0 | COCH₃ | Cl | CH₃ | CH₃ |
78
-continued
| | | | | | |
|---|---|---|---|---|---|
| 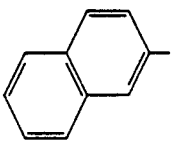 | 1 | COCH₃ | Cl | CH₃ | CH₃ |
| 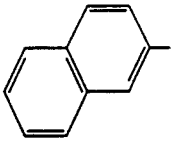 | 0 | H | CN | CH₃ | CH₃ |
| 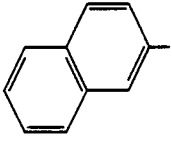 | 1 | H | CN | CH₃ | CH₃ |
| 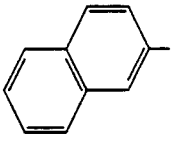 | 0 | CH₃ | CN | CH₃ | CH₃ |
| 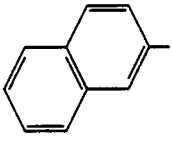 | 1 | CH₃ | CN | CH₃ | CH₃ |
| 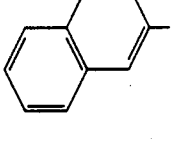 | 0 | COCH₃ | CN | CH₃ | CH₃ |
| 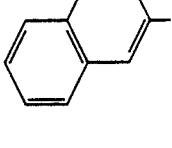 | 1 | COCH₃ | CN | CH₃ | CH₃ |
| 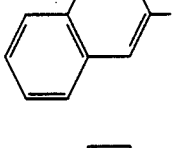 | 0 | H | H | CH₃ | Cl |
| 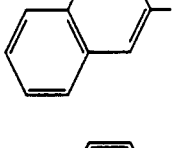 | 1 | H | H | CH₃ | Cl |
| 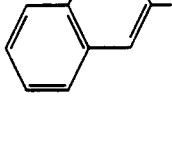 | 0 | CH₃ | H | CH₃ | Cl |

-continued
| | | | | | |
|---|---|---|---|---|---|
| 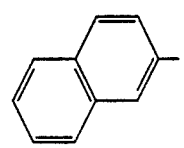 | 1 | CH₃ | H | CH₃ | Cl |
| 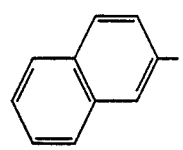 | 0 | COCH₃ | H | CH₃ | Cl |
| 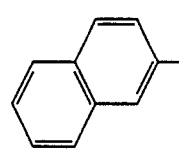 | 1 | COCH₃ | H | CH₃ | Cl |
| 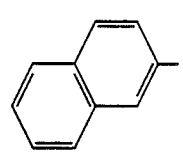 | 0 | H | Cl | CH₃ | Cl |
| 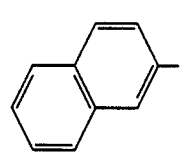 | 1 | H | Cl | CH₃ | Cl |
| 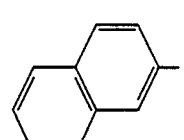 | 0 | CH₃ | Cl | CH₃ | Cl |
| 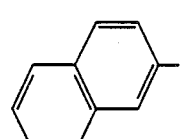 | 1 | CH₃ | Cl | CH₃ | Cl |
| 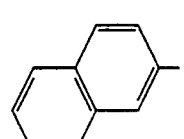 | 0 | COCH₃ | Cl | CH₃ | Cl |
| 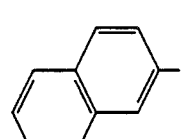 | 0 | COCH₃ | Cl | CH₃ | Cl |
| 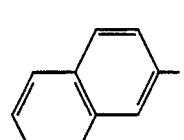 | 0 | H | CN | CH₃ | Cl |
-continued
| | | | | | |
|---|---|---|---|---|---|
| 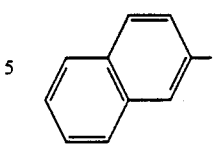 | 1 | H | CN | CH₃ | Cl |
| 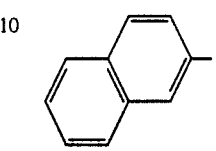 | 0 | CH₃ | CN | CH₃ | Cl |
| 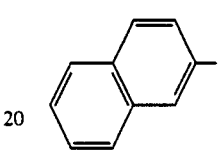 | 1 | CH₃ | CN | CH₃ | Cl |
| 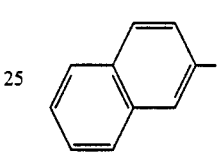 | 0 | COCH₃ | CN | CH₃ | Cl |
| 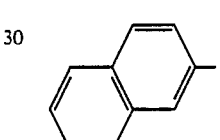 | 1 | COCH₃ | CN | CH₃ | Cl |
| 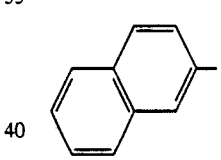 | 0 | H | H | CH₃ | CF₃ |
| 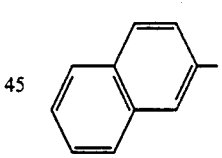 | 1 | H | H | CH₃ | CF₃ |
| 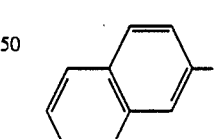 | 0 | CH₃ | H | CH₃ | CF₃ |
| 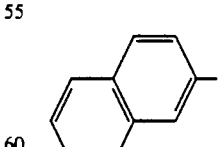 | 1 | CH₃ | H | CH₃ | CF₃ |
| 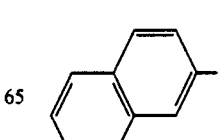 | 0 | COCH₃ | H | CH₃ | CF₃ |

| | | | | | | | | | |
|---|---|---|---|---|---|---|---|---|---|
| naphthyl | 1 | COCH$_3$ | H | CH$_3$ | CF$_3$ | naphthyl | 1 | CH$_3$ | CN | CH$_3$ | CF$_3$ |
| naphthyl | 0 | H | Cl | CH$_3$ | CF$_3$ | naphthyl | 0 | COCH$_3$ | CN | CH$_3$ | CF$_3$ |
| naphthyl | 1 | H | Cl | CH$_3$ | CF$_3$ | naphthyl | 1 | COCH$_3$ | CN | CH$_3$ | CF$_3$ |
| naphthyl | 0 | CH$_3$ | Cl | CH$_3$ | CF$_3$ | naphthyl | 0 | H | H | CH$_3$ | OCH$_3$ |
| naphthyl | 1 | CH$_3$ | Cl | CH$_3$ | CF$_3$ | naphthyl | 1 | H | H | CH$_3$ | OCH$_3$ |
| naphthyl | 0 | COCH$_3$ | Cl | CH$_3$ | CF$_3$ | naphthyl | 0 | CH$_3$ | H | CH$_3$ | OCH$_3$ |
| naphthyl | 1 | COCH$_3$ | Cl | CH$_3$ | CF$_3$ | naphthyl | 1 | CH$_3$ | H | CH$_3$ | OCH$_3$ |
| naphthyl | 0 | H | CN | CH$_3$ | CF$_3$ | naphthyl | 0 | COCH$_3$ | H | CH$_3$ | OCH$_3$ |
| naphthyl | 1 | H | CN | CH$_3$ | CF$_3$ | naphthyl | 1 | COCH$_3$ | H | CH$_3$ | OCH$_3$ |
| naphthyl | 0 | CH$_3$ | CN | CH$_3$ | CF$_3$ | naphthyl | 0 | H | Cl | CH$_3$ | OCH$_3$ |

| | | | | | |
|---|---|---|---|---|---|
| 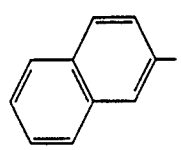 | 1 | H | Cl | CH₃ | OCH₃ |
| 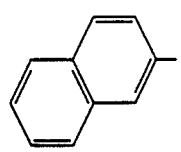 | 0 | CH₃ | Cl | CH₃ | OCH₃ |
| 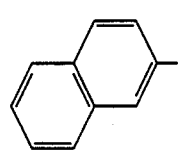 | 1 | CH₃ | Cl | CH₃ | OCH₃ |
| 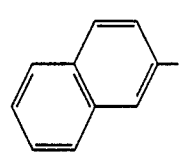 | 0 | COCH₃ | Cl | CH₃ | OCH₃ |
| 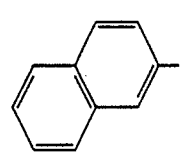 | 1 | COCH₃ | Cl | CH₃ | OCH₃ |
| 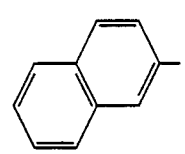 | 0 | H | CN | CH₃ | OCH₃ |
| 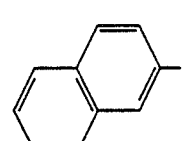 | 1 | H | CN | CH₃ | OCH₃ |
| 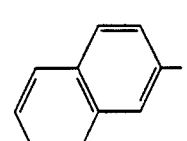 | 0 | CH₃ | CN | CH₃ | OCH₃ |
| 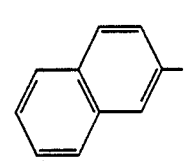 | 1 | CH₃ | CN | CH₃ | OCH₃ |
| 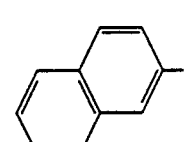 | 0 | COCH₃ | CN | CH₃ | OCH₃ |
| 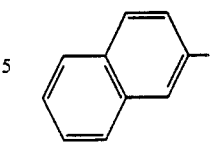 | 1 | COCH₃ | CN | CH₃ | OCH₃ |
| 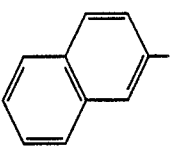 | 0 | H | H | CF₃ | CH₃ |
| 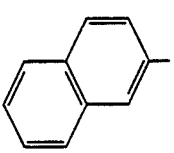 | 1 | H | H | CF₃ | CH₃ |
| 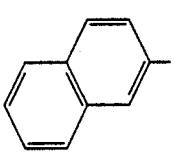 | 0 | CH₃ | H | CF₃ | CH₃ |
| 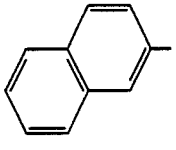 | 1 | CH₃ | H | CF₃ | CH₃ |
| 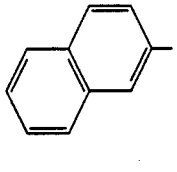 | 0 | COCH₃ | H | CF₃ | CH₃ |
| 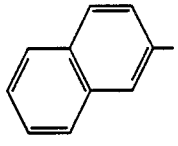 | 1 | COCH₃ | H | CF₃ | CH₃ |
| 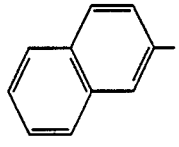 | 0 | H | Cl | CF₃ | CH₃ |
| 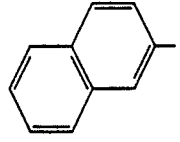 | 1 | H | Cl | CF₃ | CH₃ |
| 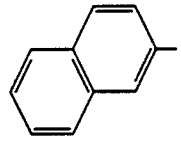 | 0 | CH₃ | Cl | CF₃ | CH₃ |

-continued
| | | | | | |
|---|---|---|---|---|---|
| 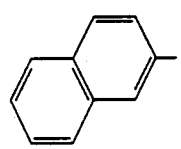 | 1 | CH₃ | Cl | CF₃ | CH₃ |
|  | 0 | COCH₃ | Cl | CF₃ | CH₃ |
| 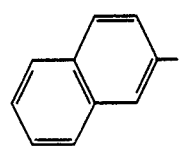 | 1 | COCH₃ | Cl | CF₃ | CH₃ |
| 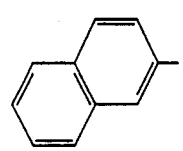 | 0 | H | CN | CF₃ | CH₃ |
| 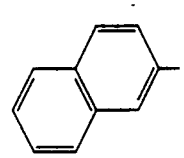 | 1 | H | CN | CF₃ | CH₃ |
| 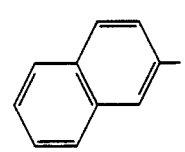 | 0 | CH₃ | CN | CF₃ | CH₃ |
| 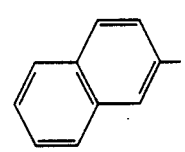 | 1 | CH₃ | CN | CF₃ | CH₃ |
| 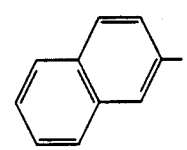 | 0 | OCH₃ | CN | CF₃ | CH₃ |
| 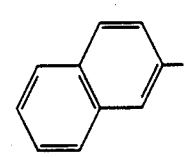 | 1 | COCH₃ | CN | CF₃ | CH₃ |
| 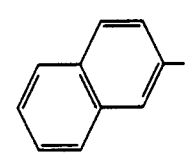 | 0 | H | H | CF₃ | CF₃ |
-continued
| | | | | | |
|---|---|---|---|---|---|
| 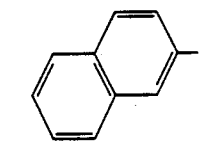 | 1 | H | H | CF₃ | CF₃ |
| 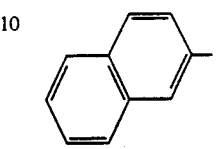 | 0 | CH₃ | H | CF₃ | CF₃ |
| 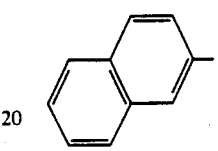 | 1 | CH₃ | H | CF₃ | CF₃ |
|  | 0 | COCH₃ | H | CF₃ | CF₃ |
| 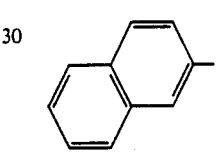 | 1 | COCH₃ | H | CF₃ | CF₃ |
| 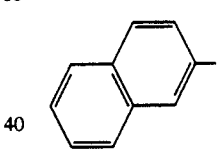 | 0 | H | Cl | CF₃ | CF₃ |
| 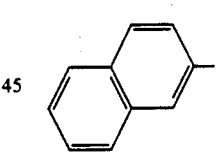 | 1 | H | Cl | CF₃ | CF₃ |
| 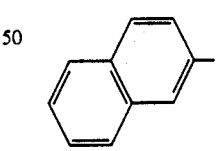 | 0 | CH₃ | Cl | CF₃ | CF₃ |
| 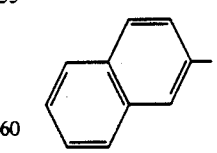 | 1 | CH₃ | Cl | CF₃ | CF₃ |
| 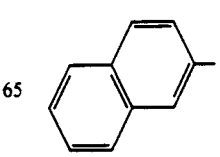 | 0 | COCH₃ | Cl | CF₃ | CF₃ |

-continued
| A | n | R¹ | R² | R⁴ | R⁴" |
|---|---|---|---|---|---|
| 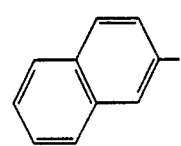 | 1 | COCH₃ | Cl | CF₃ | CF₃ |
|  | 0 | H | CN | CF₃ | CF₃ |
| 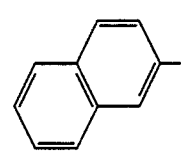 | 1 | H | CN | CF₃ | CF₃ |
| 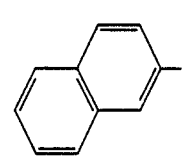 | 0 | CH₃ | CN | CF₃ | CF₃ |
| 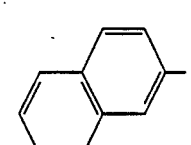 | 1 | CH₃ | CN | CF₃ | CF₃ |
| 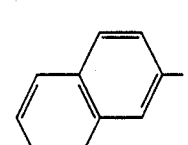 | 0 | COCH₃ | CN | CF₃ | CF₃ |
| 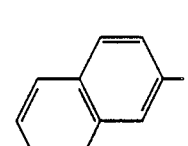 | 1 | COCH₃ | CN | CF₃ | CF₃ |
TABLE III
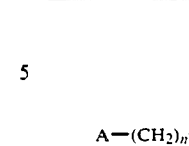
| A | n | R¹ | R² | R⁴ | R⁴" |
|---|---|---|---|---|---|
| 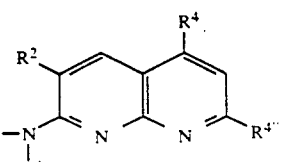 | 0 | H | H | CH₃ | OCH₃ |
| 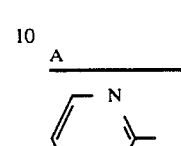 | 1 | H | H | CH₃ | OCH₃ |
TABLE III-continued
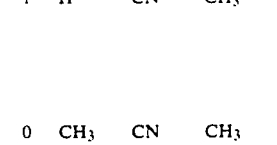
| A | n | R¹ | R² | R⁴ | R⁴" |
|---|---|---|---|---|---|
| 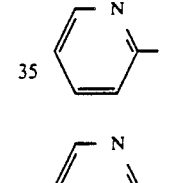 | 0 | CH₃ | H | CH₃ | OCH₃ |
| 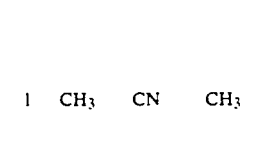 | 1 | CH₃ | H | CH₃ | OCH₃ |
| 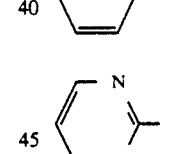 | 0 | H | CN | CH₃ | OCH₃ |
| 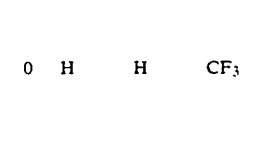 | 1 | H | CN | CH₃ | OCH₃ |
| 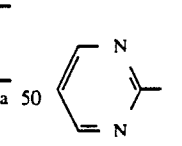 | 0 | CH₃ | CN | CH₃ | OCH₃ |
| 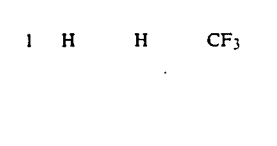 | 1 | CH₃ | CN | CH₃ | OCH₃ |
| 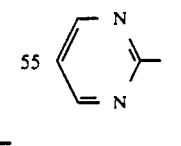 | 0 | H | H | CF₃ | OCH₃ |
| 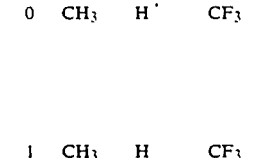 | 1 | H | H | CF₃ | OCH₃ |
| 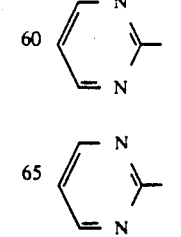 | 0 | CH₃ | H | CF₃ | OCH₃ |
| 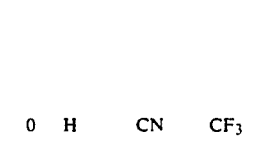 | 1 | CH₃ | H | CF₃ | OCH₃ |
|  | 0 | H | CN | CF₃ | OCH₃ |

TABLE III-continued

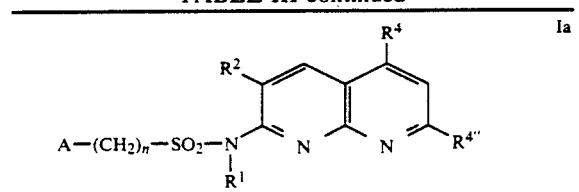

| A | n | R¹ | R² | R⁴ | R⁴" |
|---|---|----|----|----|-----|
| pyrimidinyl | 1 | H | CN | CF₃ | OCH₃ |
| pyrimidinyl | 0 | CH₃ | CN | CF₃ | OCH₃ |
| pyrimidinyl | 1 | CH₃ | CN | CF₃ | OCH₃ |
| pyrrolyl | 0 | H | H | CH₃ | CF₃ |
| pyrrolyl | 1 | H | H | CH₃ | CF₃ |
| pyrrolyl | 0 | CH₃ | H | CH₃ | CF₃ |
| pyrrolyl | 1 | CH₃ | H | CH₃ | CF₃ |
| pyrrolyl | 0 | H | CN | CH₃ | CF₃ |
| pyrrolyl | 1 | H | CN | CH₃ | CF₃ |
| pyrrolyl | 0 | CH₃ | CN | CH₃ | CF₃ |
| pyrrolyl | 1 | CH₃ | CN | CH₃ | CF₃ |
| furyl | 0 | H | H | CH₃ | OCH₃ |
| furyl | 1 | H | H | CH₃ | OCH₃ |

TABLE III-continued

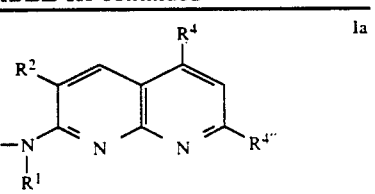

| A | n | R¹ | R² | R⁴ | R⁴" |
|---|---|----|----|----|-----|
| furyl | 0 | CH₃ | H | CH₃ | OCH₃ |
| furyl | 1 | CH₃ | H | CH₃ | OCH₃ |
| furyl | 0 | H | CN | CH₃ | OCH₃ |
| furyl | 1 | H | CN | CH₃ | OCH₃ |
| furyl | 0 | CH₃ | CN | CH₃ | OCH₃ |
| furyl | 1 | CH₃ | CN | CH₃ | OCH₃ |
| thienyl | 0 | H | H | CF₃ | OCH₃ |
| thienyl | 1 | H | H | CF₃ | OCH₃ |
| thienyl | 0 | CH₃ | H | CF₃ | OCH₃ |
| thienyl | 1 | CH₃ | H | CF₃ | OCH₃ |
| thienyl | 0 | H | CN | CF₃ | OCH₃ |
| thienyl | 1 | H | CN | CF₃ | OCH₃ |
| thienyl | 0 | CH₃ | CN | CF₃ | OCH₃ |

TABLE III-continued

Ia

Structure: A—(CH₂)ₙ—SO₂—N(R¹)— attached to 1,8-naphthyridine with R² and R⁴ on pyridine ring and R⁴'' position.

| A | n | R¹ | R² | R⁴ | R⁴'' |
|---|---|----|----|----|------|
| thiophen-2-yl | 1 | CH₃ | CN | CF₃ | OCH₃ |
| imidazol-2-yl (NH) | 0 | H | H | CH₃ | CF₃ |
| imidazol-2-yl (NH) | 1 | H | H | CH₃ | CF₃ |
| imidazol-2-yl (NH) | 0 | CH₃ | H | CH₃ | CF₃ |
| imidazol-2-yl (NH) | 1 | CH₃ | H | CH₃ | CF₃ |
| imidazol-2-yl (NH) | 0 | H | CN | CH₃ | CF₃ |
| imidazol-2-yl (NH) | 1 | H | CN | CH₃ | CF₃ |
| imidazol-2-yl (NH) | 0 | CH₃ | CN | CH₃ | CF₃ |
| imidazol-2-yl (NH) | 1 | CH₃ | CN | CH₃ | CF₃ |
| oxazol-2-yl | 0 | H | H | CH₃ | OCH₃ |
| oxazol-2-yl | 1 | H | H | CH₃ | OCH₃ |
| oxazol-2-yl | 0 | CH₃ | H | CH₃ | OCH₃ |
| oxazol-2-yl | 1 | CH₃ | H | CH₃ | OCH₃ |
| oxazol-2-yl | 0 | H | CN | CH₃ | OCH₃ |
| oxazol-2-yl | 1 | H | CN | CH₃ | OCH₃ |
| oxazol-2-yl | 0 | CH₃ | CN | CH₃ | OCH₃ |
| oxazol-2-yl | 1 | CH₃ | CN | CH₃ | OCH₃ |
| isoxazol-5-yl | 0 | H | H | CF₃ | OCH₃ |
| isoxazol-5-yl | 1 | H | H | CF₃ | OCH₃ |
| isoxazol-5-yl | 0 | CH₃ | H | CF₃ | OCH₃ |
| isoxazol-5-yl | 1 | CH₃ | H | CF₃ | OCH₃ |
| isoxazol-5-yl | 0 | H | CN | CF₃ | OCH₃ |
| isoxazol-5-yl | 1 | H | CN | CF₃ | OCH₃ |
| isoxazol-5-yl | 0 | CH₃ | CN | CF₃ | OCH₃ |
| isoxazol-5-yl | 0 | CH₃ | CN | CF₃ | OCH₃ |

TABLE III-continued $$\text{A-(CH}_2)_n\text{-SO}_2\text{-N}(R^1)\text{-[pyridopyridine with } R^2, R^4, R^{4''}\text{]}\quad\text{Ia}$$

| A | n | R¹ | R² | R⁴ | R⁴'' |
|---|---|----|----|----|------|
| indol-3-yl | 0 | H | H | CH₃ | CF₃ |
| indol-3-yl | 1 | H | H | CH₃ | CF₃ |
| indol-3-yl | 0 | CH₃ | H | CH₃ | CF₃ |
| indol-3-yl | 1 | CH₃ | H | CH₃ | CF₃ |
| indol-3-yl | 0 | H | CN | CH₃ | CF₃ |
| indol-3-yl | 1 | H | CN | CH₃ | CF₃ |
| indol-3-yl | 0 | CH₃ | CN | CH₃ | CF₃ |
| indol-3-yl | 1 | CH₃ | CN | CH₃ | CF₃ |
| quinolin-2-yl | 0 | H | H | CH₃ | OCH₃ |
| quinolin-2-yl | 1 | H | H | CH₃ | OCH₃ |
| quinolin-2-yl | 0 | CH₃ | H | CH₃ | OCH₃ |
| quinolin-2-yl | 1 | CH₃ | H | CH₃ | OCH₃ |
| quinolin-2-yl | 0 | H | CN | CH₃ | OCH₃ |
| quinolin-2-yl | 1 | H | CN | CH₃ | OCH₃ |
| quinolin-2-yl | 0 | CH₃ | CN | CH₃ | OCH₃ |
| quinolin-2-yl | 1 | CH₃ | CN | CH₃ | OCH₃ |
| isoquinolin-3-yl | 0 | H | H | CF₃ | OCH₃ |
| isoquinolin-3-yl | 1 | H | H | CF₃ | OCH₃ |
| isoquinolin-3-yl | 0 | CH₃ | H | CF₃ | OCH₃ |
| isoquinolin-3-yl | 1 | CH₃ | H | CF₃ | OCH₃ |
| isoquinolin-3-yl | 0 | H | CN | CF₃ | OCH₃ |

TABLE III-continued $$A-(CH_2)_n-SO_2-N(R^1)-\text{[pyridopyridine with } R^2, R^4, R^{4''}\text{]}\quad Ia$$

| A | n | R¹ | R² | R⁴ | R⁴'' |
|---|---|----|----|----|------|
| isoquinolin-3-yl | 1 | H | CN | CF₃ | OCH₃ |
| isoquinolin-3-yl | 0 | CH₃ | CN | CF₃ | OCH₃ |
| isoquinolin-3-yl | 0 | CH₃ | CN | CF₃ | OCH₃ |
| 2-methylbenzimidazol-2-yl | 0 | H | H | CH₃ | CF₃ |
| 2-methylbenzimidazol-2-yl | 1 | H | H | CH₃ | CF₃ |
| 2-methylbenzimidazol-2-yl | 0 | CH₃ | H | CH₃ | CF₃ |
| 2-methylbenzimidazol-2-yl | 1 | CH₃ | H | CH₃ | CF₃ |
| 2-methylbenzimidazol-2-yl | 0 | H | CN | CH₃ | CF₃ |
| 2-methylbenzimidazol-2-yl | 1 | H | CN | CH₃ | CF₃ |
| 2-methylbenzimidazol-2-yl | 0 | CH₃ | CN | CH₃ | CF₃ |
| 2-methylbenzimidazol-2-yl | 1 | CH₃ | CN | CH₃ | CF |

TABLE IV $$A-SO_2-N(R^1)-\text{[pyrido-pyrimidine with } R^2, R^4, R^{4''}, Y\text{]}$$

| A | R¹ | R² | R⁴ | R⁴'' | Y |
|---|----|----|----|------|---|
| 3-pyridyl | H | H | CH₃ | OCH₃ | N |
| 3-pyridyl | CH₃ | H | CH₃ | OCH₃ | N |
| 3-pyridyl | H | CN | CH₃ | OCH₃ | C—Cl |
| 3-pyridyl | CH₃ | CN | CH₃ | OCH₃ | C—Cl |
| 4-pyridyl | H | H | CH₃ | CF₃ | N |
| 4-pyridyl | CH₃ | H | CH₃ | CF₃ | N |
| 4-pyridyl | H | CN | CH₃ | CF₃ | C—Cl |
| 4-pyridyl | CH₃ | CN | CH₃ | CF₃ | C—Cl |

TABLE IV-continued

Structure:
$$A-SO_2-N(R^1)-\text{[pyridopyrimidine core with } R^2, R^4, Y, R^{4''}\text{]}$$

| A | R¹ | R² | R⁴ | R⁴'' | Y |
|---|----|----|----|------|---|
| pyrimidinyl | H | H | CF₃ | CH₃ | N |
| pyrimidinyl | CH₃ | H | CF₃ | CH₃ | N |
| pyrimidinyl | H | CN | CF₃ | CH₃ | C—Cl |
| pyrimidinyl | CH₃ | CN | CF₃ | CH₃ | C—Cl |
| pyrrolyl | H | H | CH₃ | Cl | N |
| pyrrolyl | CH₃ | H | CH₃ | Cl | N |
| pyrrolyl | H | CN | CH₃ | Cl | C—Cl |
| pyrrolyl | CH₃ | CN | CH₃ | Cl | C—Cl |
| thienyl | H | H | CF₃ | CF₃ | N |
| thienyl | CH₃ | H | CF₃ | CF₃ | N |
| thienyl | H | CN | CF₃ | CF₃ | C—Cl |
| thienyl | CH₃ | CN | CF₃ | CF₃ | C—Cl |
| methylfuryl | H | H | CH₃ | CH₃ | N |
| methylfuryl | CH₃ | H | CH₃ | CH₃ | N |
| methylfuryl | H | CN | CH₃ | CH₃ | C—Cl |
| methylfuryl | CH₃ | CN | CH₃ | CH₃ | C—Cl |
| methylimidazolyl | H | H | CH₃ | CH₃ | N |
| methylimidazolyl | CH₃ | H | CH₃ | OCH₃ | N |
| methylimidazolyl | H | CN | CH₃ | OCH₃ | C—Cl |
| methylimidazolyl | CH₃ | CN | CH₃ | OCH₃ | C—Cl |
| methyloxazolyl | H | H | CH₃ | CF₃ | N |
| methyloxazolyl | CH₃ | H | CH₃ | CF₃ | N |
| methyloxazolyl | H | CN | CH₃ | CF₃ | C—Cl |
| methyloxazolyl | CH₃ | CN | CH₃ | CF₃ | C—Cl |
| methylthiazolyl | H | H | CF₃ | CH₃ | N |
| methylthiazolyl | CH₃ | H | CF₃ | CH₃ | N |

TABLE IV-continued

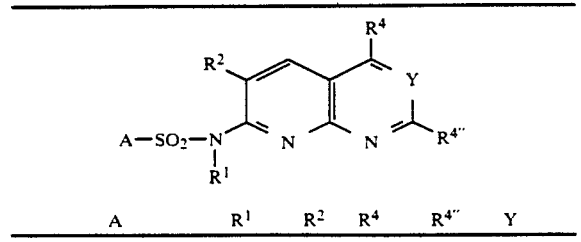

| A | R¹ | R² | R⁴ | R⁴'' | Y |
|---|----|----|----|------|---|
| (isothiazole) | H | CN | CF₃ | CH₃ | C—Cl |
| (isothiazole) | CH₃ | CN | CF₃ | CH₃ | C—Cl |
| (isoxazole) | H | H | CH₃ | Cl | N |
| (isoxazole) | CH₃ | H | CH₃ | Cl | N |
| (isoxazole) | H | CN | CH₃ | Cl | C—Cl |
| (isoxazole) | CH₃ | CN | CH₃ | Cl | C—Cl |
| (thiazole) | H | H | CF₃ | CF₃ | N |
| (thiazole) | CH₃ | H | CF₃ | CF₃ | N |
| (thiazole) | H | CN | CF₃ | CF₃ | C—Cl |
| (thiazole) | CH₃ | CN | CF₃ | CF₃ | C—Cl |
| (pyrazole) | H | H | CH₃ | CH₃ | N |
| (pyrazole) | CH₃ | H | CH₃ | CH₃ | N |
| (pyrazole) | H | CN | CH₃ | CH₃ | C—Cl |

TABLE IV-continued

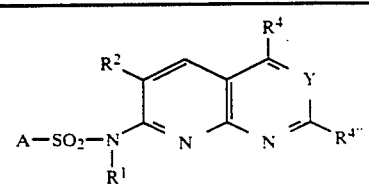

| A | R¹ | R² | R⁴ | R⁴'' | Y |
|---|----|----|----|------|---|
| (pyrazole) | CH₃ | CN | CH₃ | CH₃ | C—Cl |
| (indole) | H | H | CH₃ | OCH₃ | N |
| (indole) | CH₃ | H | CH₃ | OCH₃ | N |
| (indole) | H | CN | CH₃ | OCH₃ | C—Cl |
| (indole) | CH₃ | CN | CH₃ | OCH₃ | C—Cl |
| (quinoline) | H | H | CH₃ | CF₃ | N |
| (quinoline) | CH₃ | H | CH₃ | CF₃ | N |
| (quinoline) | H | CN | CH₃ | CF₃ | C—Cl |
| (quinoline) | CH₃ | CN | CH₃ | CF₃ | C—Cl |
| (benzothiazole) | H | H | CF₃ | CH₃ | N |
| (benzothiazole) | CH₃ | H | CF₃ | CH₃ | N |

TABLE IV-continued

| A | R¹ | R² | R⁴ | R⁴''' | Y |
|---|---|---|---|---|---|
| benzothiazol-2-yl | H | CN | CF₃ | CH₃ | C—Cl |
| benzothiazol-2-yl | CH₃ | CN | CF₃ | CH₃ | C—Cl |
| benzoxazol-2-yl | H | H | CH₃ | Cl | N |
| benzoxazol-2-yl | CH₃ | H | CH₃ | Cl | N |
| benzoxazol-2-yl | H | CN | CH₃ | Cl | C—Cl |
| benzoxazol-2-yl | CH₃ | CN | CH₃ | Cl | C—Cl |
| benzimidazol-2-yl | H | H | CF₃ | CF₃ | N |
| benzimidazol-2-yl | CH₃ | H | CF₃ | CF₃ | N |
| benzimidazol-2-yl | H | CN | CF₃ | CF₃ | C—Cl |
| benzimidazol-2-yl | CH₃ | CN | CF₃ | CF₃ | C—Cl |
| quinoxalin-2-yl | H | H | CH₃ | CH₃ | N |
| quinoxalin-2-yl | CH₃ | H | CH₃ | CH₃ | N |
| quinoxalin-2-yl | H | CN | CH₃ | CH₃ | C—Cl |
| quinoxalin-2-yl | CH₃ | CN | CH₃ | CH₃ | C—Cl |

The substituted sulfonamides I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90%, by weight of active ingredient.

Examples of formulations are given below.

I. 90 parts by weight of compound no. 1.047 is mixed with 10 parts by weight of N-methyl-alpha-pyrrolidone. A mixture is obtained which is suitable for application in the form of very fine drops.

II. 20 parts by weight of compound no. 1.011 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3.008 is dissolved in a mixture consisting of 40 parts by weight of cyclohexanone 30 parts by weight of isobutanol, 20 parts by weight of the adduct of 7 moles of ethylene oxide and 1 mole of isooctylphenol and 10 parts by weight of the adduct of 40 moles of ethylene oxide and 1 mole of castor oil. By pouring the solution into 100,000 part by weight of water and finely distributing it therein, an aqueous dispersion is obtained containing 0.02% by weight of the active ingredient.

IV. 20 parts by weight of compound no. 3.012 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein an aqueous dispersion is obtained containing 0.02% by weight of the active ingredient.

V. 20 parts by weight of compound no. 2.023 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water a spray liquor is obtained containing 0.1% by weight of the active ingredient.

VI. 3 parts by weight of compound no. 1.092 is intimately mixed with 97 parts by weight of particulate kaolin. A dust is obtained containing 3% by weight of the active ingredient.

VII. 30 parts by weight of compound no. 3.039 is intimately mixed with a mixture consisting of 92 parts by weight silica gel and 8 parts by weight of paraffin oil which has been sprayed onto the surface of this silica gel. A formulation of the active ingredient is obtained having good adherence.

VIII. 20 parts of compound no. 1.037 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The herbicidal agents may be applied pre- or post-emergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year; the plants to be combated and their growth stage, and are from 0.001 to 5.0, preferably 0.01 to 1.0, kg/ha.

In view of the wide variety of application methods, the compounds according to the invention, or the agents containing them, may be used in a large variety of crop plants for combating unwanted plant growth. The following crops are given by way of example:

| Botanical name | Common name |
|---|---|
| *Ananas comosus* | pineapples |
| *Arachis hypogaea* | peanuts (groundnuts) |
| *Asparagus officinalis* | asparagus |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cynodon dactylon* | Bermudagrass |
| *Elais guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Hevea brasiliensis* | rubber plants |

-continued

| Botanical name | Common name |
| --- | --- |
| Hordeum vulgare | barley |
| Humulus lupulus | hops |
| Ipomoea batatas | sweet potatoes |
| Juglans regia | walnut trees |
| Lactuca sativa | lettuce |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the sulfonamides of the formula I may be mixed and applied together with numerous representatives of other herbicidal or growth-regulating active ingredient groups. Examples of suitable components are diazines, 4H-3,1-benzoxazine derivatives, benzothiadiazinones, 2 6-dinitroanilines, N-phenylcarbamates, thiolcarbamates, halocarboxylic acids, triazines, amides, ureas, diphenyl ethers, triazinones, uracils, benzofuran derivatives, imidazolinones, sulfonylureas, cyclohexane-1,3-dione derivatives, quinolinecarboxylic acids, phenyloxy- and heteroaryloxy-phenoxyproponic acids and salts, esters and amides thereof, etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

The directions given in the synthesis examples below were employed, after appropriate modification of the starting materials to produce further compounds I. The compounds thus obtained are listed, with physical data, in Tables 1, 1a, 2 and 3.

EXAMPLE 1

2-Chloro-N-5,7-dimethyl-1,8-naphthyridin-2-yl)-benzenesulfonamide

At an internal temperature of 40° to 50° C., 7.5 g (35.5 mmol) of 2-chlorobenzenesulfonyl chloride was slowly dripped, while stirring, into a suspension of 4.1 g (23.6 mmol) of commercially available 2-amino-5,7-dimethyl-1,8-naphthyridine in 100 ml of anhydrous pyridine. The reaction mixture was subsequently stirred for an hour at 75° C., and then refluxed for a further 90 mins. After the mixture had cooled, it was evaporated to dryness and the residue was subjected to column chromatography over silica gel using, as mobile phase, first methylene chloride and then ethyl acetate. The crude product was further purified by recrystallization from methanol. There was obtained 0.75 g (9%) of the desired product, which was characterized by $^1$H-NMR and infrared spectroscopy and has a melting point of 200° to 202° C.

$^1$H-NMR spectrum 250 MHz, CDCl$_3$):

δ [ppm]=2.55 (s; 3H), 2.60 (s; 3H), 6.92 (d, I=9.5 HZ; 1H), 7.05 (s; 1H), 7.35–7.50 (m; 3H), 8.03 (d, I=9.5 Hz; 1H), 8.28 (d, I=7 Hz; 1H), 12.0 (br, s; 1H).

EXAMPLE 2

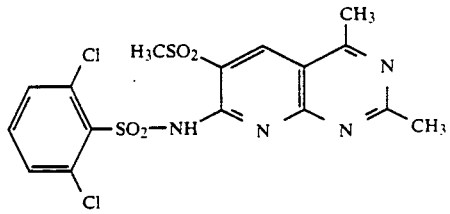

(a) At 2.5° C., 30.3 g (0.25 mol) of methylsulfonylacetonitrile and then 45.8 g (0.25 mol) of a 30% strength sodium methylate solution in methanol were added to a suspension of 38.4 g (0.25 mol) of 4-amino-2,6-dienethylpyrimidine-5-carbaldehyde in 600 ml of methanol. Upon gentle heating a clear solution at first formed, from which a high-volume precipitate settled out. After the mixture had been stirred for 2 hours at boiling temperature, it was cooled to 0° C., and the precipitate was isolated, washed and dried. There was obtained 47% of 7-amino-2,4-dimethyl-6-methylsulfonylpyrido(2,3-d)-pyrimidine.

$^1$H-NMR (250 MHZ, d$^6$ DMSO, vs, TMS):

δ [ppm]: 8.70 (s, 1H), 7.43 (br, 2H), 3.34 (s, 3H), 2.71 (s, 3H), 2.61 (s, 3H).

At room temperature 5.0 g (20 mol) of the amine obtained under (a) was added to a suspension of 1.05 g (44 mmol) of NaH in 80 ml of THF, and the mixture was refluxed until no more gas evolved. After the mixture had been cooled to about 40° C., 5.4 g (22 mmol) of 2,6-dichlorobenzenesulfonyl chloride in 20 ml of THF was added and the resulting mixture was stirred for 5 hours at the reflux temperature. The precipitate which formed was filtered off under suction and taken up in a mixture of methylene chloride and 3 N hydrochloric acid. The organic phase was isolated, washed with water, and dried under reduced pressure. There was obtained 81% of the desired sulfonamide mp. >230° C. (active ingredient 3.008).

TABLE 1

$$A-(-CH_2)_n-SO_2-N(R^1)-\text{[1,8-naphthyridine with } R^4, R^{4'}\text{]}$$

| Compound | A | n | $R^1$ | $R^4$ | $R^{4'}$ | mp [°C.] |
|---|---|---|---|---|---|---|
| 1.001 | phenyl | 0 | H | $CH_3$ | $CH_3$ | 182–184 |
| 1.002 | 2-($CO_2CH_3$)phenyl | 0 | H | $CH_3$ | $CH_3$ | 178–180 |
| 1.003 | 2-($CO_2CH_3$)phenyl | 0 | H | $CH_3$ | Cl | 174–179 |
| 1.004 | 2-($CO_2CH_3$)phenyl | 0 | H | $CH_3$ | $CF_3$ | 161–164 |
| 1.004 . N(n-$C_4H_9$)$_3$ | 2-($CO_2CH_3$)phenyl | 0 | H | $CH_3$ | $CF_3$ | 63–68 |
| 1.005 | 2-($CO_2CH_3$)phenyl | 0 | H | $CF_3$ | $CH_3$ | 153–156 |
| 1.006 | 2-($CO_2CH_3$)phenyl | 0 | H | $CH_3$ | $OCH_3$ | 179–183 |
| 1.006 . HCl | 2-($CO_2CH_3$)phenyl | 0 | H | $CH_3$ | $OCH_3$ | 169–171 |
| 1.007 | 2-($CO_2CH_3$)phenyl | 0 | K | $CF_3$ | $CF_3$ | 265–268 |
| 1.008 | 2-Cl-phenyl | 0 | H | $CH_3$ | $CH_3$ | 200–202 |

TABLE 1-continued $$A-(CH_2)_n-SO_2-N(R^1)-\text{[1,8-naphthyridine with } R^4, R^{4'}\text{]}$$

| Compound | A | n | $R^1$ | $R^4$ | $R^{4'}$ | mp [°C] |
|---|---|---|---|---|---|---|
| 1.009 | 3-CF$_3$-phenyl | 0 | H | CH$_3$ | CH$_3$ | 128–132 |
| 1.010 | 2,6-diCl-phenyl | 0 | H | CH$_3$ | CH$_3$ | 230–233 |
| 1.011 | 2,6-diCl-phenyl | 0 | H | CH$_3$ | Cl | 225–229 |
| 1.011 · N(n-C$_4$H$_9$)$_3$ | 2,6-diCl-phenyl | 0 | H | CH$_3$ | Cl | 96–98 |
| 1.012 | 2,6-diCl-phenyl | 0 | H | CH$_3$ | CF$_3$ | 181–184 |
| 1.013 | 2,6-diCl-phenyl | 0 | H | CF$_3$ | CH$_3$ | 232–235 |
| 1.014 | 2,6-diCl-phenyl | 0 | H | CH$_3$ | OCH$_3$ | 215–221 |
| 1.015 | 2,6-diCl-phenyl | 0 | H | CF$_3$ | CF$_3$ | 215–219 |
| 1.016 | 2-CO$_2$CH$_3$-phenyl | 0 | Na | CH$_3$ | OCH$_3$ | 208–214 |
| 1.017 | 2-Cl-6-CH$_3$-phenyl | 0 | H | CH$_3$ | CH$_3$ | 229–232 |

TABLE 1-continued
A—(—CH$_2$)$_n$—SO$_2$—N(R$^1$)-[naphthyridine with R$^4$, R$^{4'}$]
| Compound | A | n | R$^1$ | R$^4$ | R$^{4'}$ | mp [°C.] |
|---|---|---|---|---|---|---|
| 1.017 . HCl | 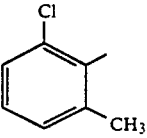 2-Cl-6-CH$_3$-phenyl | 0 | H | CH$_3$ | CH$_3$ | 241-249 |
| 1.018 | 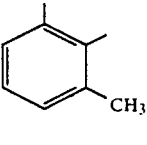 2-Cl-6-CH$_3$-phenyl | 0 | H | CH$_3$ | Cl | 200-203 |
| 1.019 | 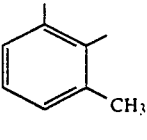 2-Cl-6-CH$_3$-phenyl | 0 | H | CF$_3$ | CH$_3$ | 186-189 |
| 1.020 | 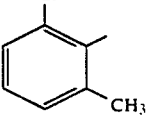 2-Cl-6-CH$_3$-phenyl | 0 | H | CH$_3$ | CF$_3$ | 187-189 |
| 1.021 | 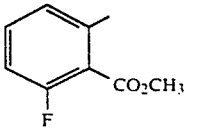 2-CO$_2$CH$_3$-6-F-phenyl | 0 | H | CH$_3$ | CH$_3$ | 210-215 |
| 1.022 | 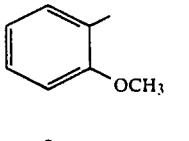 2-OCH$_3$-phenyl | 0 | H | CH$_3$ | CH$_3$ | 218-222 |
| 1.023 | 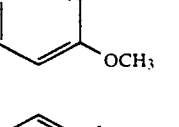 2-OCH$_3$-phenyl | 0 | Na | CH$_3$ | CH$_3$ | 236-239 |
| 1.024 | 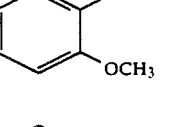 2-OCH$_3$-phenyl | 0 | H | CH$_3$ | Cl | 232-238 |
| 1.025 | 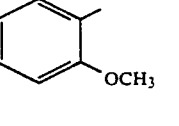 2-OCH$_3$-phenyl | 0 | H | CH$_3$ | OCH$_3$ | 192-196 |
| 1.026 | 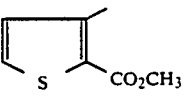 2-CO$_2$CH$_3$-thienyl | 0 | H | CH$_3$ | CH$_3$ | 207-211 |

TABLE 1-continued $$A-(CH_2)_n-SO_2-N(R^1)-\text{[naphthyridine with } R^4, R^{4'}\text{]}$$

| Compound | A | n | $R^1$ | $R^4$ | $R^{4'}$ | mp [°C.] |
|---|---|---|---|---|---|---|
| 1.026 . HCl | 3-(CO₂CH₃)-thiophen-2-yl | 0 | H | CH₃ | CH₃ | 204–209 |
| 1.027 | 3-(CO₂CH₃)-thiophen-2-yl | 0 | H | CH₃ | Cl | 218–220 |
| 1.028 | 3-(CO₂CH₃)-thiophen-2-yl | 0 | H | CF₃ | CH₃ | 192–195 |
| 1.029 | 3-(CO₂CH₃)-thiophen-2-yl | 0 | H | CH₃ | CF₃ | 198–200 |
| 1.030 | 2-(CO₂CH₃)-3-Cl-phenyl | 0 | H | CH₃ | CH₃ | 244–228 |
| 1.031 | 2-(CO₂CH₃)-3-CH₃-phenyl | 0 | H | CH₃ | CH₃ | 188–192 |
| 1.032 | 2-(CO₂CH₃)-3-CH₃-phenyl | 0 | H | CH₃ | Cl | 169–170 |
| 1.033 | 2-(CO₂CH₃)-3-CH₃-phenyl | 0 | H | CH₃ | OCH₃ | 172–176 |
| 1.034 | 2-Cl-phenyl | 1 | H | CH₃ | CH₃ | 204–207 |
| 1.035 | 2-Cl-phenyl | 1 | H | CH₃ | Cl | 215–218 |
| 1.036 | 2-NO₂-phenyl | 0 | H | CH₃ | CH₃ | 165 (decomp.) |

TABLE 1-continued $$A-(-CH_2)_n-SO_2-\underset{R^1}{N}-\text{[4,4'-disubstituted-1,8-naphthyridin-2-yl]}$$

with substituents $R^4$ and $R^{4'}$ on the naphthyridine

| Compound | A | n | $R^1$ | $R^4$ | $R^{4'}$ | mp [°C.] |
|---|---|---|---|---|---|---|
| 1.037 | 2,5-dichlorophenyl | 0 | H | $CH_3$ | $CH_3$ | 229–233 |
| 1.038 | 2,5-dichlorophenyl | 0 | H | $CH_3$ | Cl | 224–227 |
| 1.039 | 2,5-dimethoxyphenyl | 0 | H | $CH_3$ | $CH_3$ | 179–183 |
| 1.040 | 2,5-dimethoxyphenyl | 0 | Na | $CH_3$ | $CH_3$ | 193 (decomp.) |
| 1.041 | 2,5-dimethoxyphenyl | 0 | H | $CH_3$ | Cl | 200–205 |
| 1.042 | 3-(trifluoromethyl)phenyl | 0 | Na | $CH_3$ | $CH_3$ | 172–180 |
| 1.043 | 2-thienyl | 0 | H | $CH_3$ | $CH_3$ | 199–202 |
| 1.044 | 2-($CO_2C_2H_5$)phenyl | 1 | H | $CH_3$ | $CH_3$ | 175–179 |
| 1.045 | 2-chloro-6-($CO_2CH_3$)phenyl | 0 | H | $CH_3$ | $CH_3$ | 207–210 |

TABLE 1-continued
A—(CH₂)ₙ—SO₂—N(R¹)—[pyridine system with R⁴ and R⁴']
| Compound | A | n | R¹ | R⁴ | R⁴' | mp [°C.] |
|---|---|---|---|---|---|---|
| 1.046 | 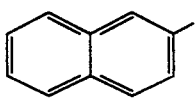 2-naphthyl | 0 | H | CH₃ | CH₃ | 187–190 |
| 1.047 | 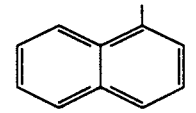 1-naphthyl | 0 | H | CH₃ | CH₃ | 224–226 |
| 1.048 | 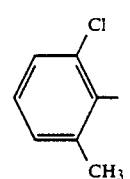 2-Cl, 6-CH₃-phenyl | 0 | H | CF₃ | CF₃ | 165–168 |
| 1.049 | 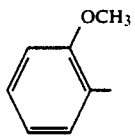 2-OCH₃-phenyl | 0 | H | CF₃ | CF₃ | 172–182 |
| 1.050 | 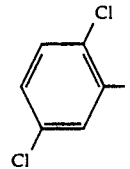 2,4-diCl-phenyl | 0 | H | CF₃ | CF₃ | 172–177 |
| 1.051 | 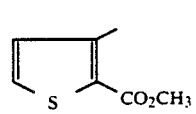 3-CH₃, 2-CO₂CH₃-thienyl | 0 | H | CF₃ | CF₃ | 151–157 |
| 1.052 | 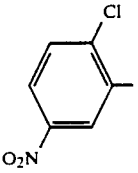 4-Cl, 3-NO₂-phenyl | 0 | H | CH₃ | CH₃ | 259–263 |
| 1.053 | 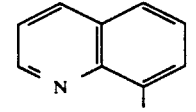 8-quinolinyl | 0 | H | CH₃ | CH₃ | 249–255 |
| 1.054 | 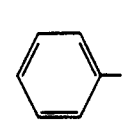 phenyl | 0 | H | CH₃ | Cl | 173–175 |

TABLE 1-continued $$A-(CH_2)_n-SO_2-\underset{R^1}{N}-\text{[1,8-naphthyridine with } R^4, R^{4'}\text{]}$$

| Compound | A | n | $R^1$ | $R^4$ | $R^{4'}$ | mp [°C.] |
|---|---|---|---|---|---|---|
| 1.055 | 2,6-dichlorophenyl | 0 | H | $CH_3$ | $N(CH_3)_2$ | 286–288 |
| 1.056 | 2-($CO_2CH_3$)phenyl | 0 | H | $CH_3$ | $N(CH_3)_2$ | 240–243 |
| 1.057 | 2-fluorophenyl | 0 | H | $CH_3$ | $CH_3$ | 209–210 |
| 1.058 | 2-cyanophenyl | 0 | H | $CH_3$ | $CH_3$ | 259–261 |
| 1.059 | 5-chloro-2-thienyl | 0 | H | $CH_3$ | $CH_3$ | 161–162 |
| 1.060 | 4-fluorophenyl | 0 | H | $CH_3$ | $CH_3$ | 200–202 |
| 1.061 | 2,4,6-trimethylphenyl | 0 | H | $CH_3$ | $CH_3$ | 184–188 |
| 1.062 | 2,6-difluorophenyl | 0 | H | $CH_3$ | $CH_3$ | 210–215 |
| 1.063 | 4-fluorophenyl | 0 | H | $CH_3$ | Cl | 160–170 |

TABLE 1-continued

A—(CH$_2$)$_n$—SO$_2$—N(R$^1$)— [naphthyridine with R$^4$ and R$^{4'}$]

| Compound | A | n | R$^1$ | R$^4$ | R$^{4'}$ | mp [°C.] |
|---|---|---|---|---|---|---|
| 1.064 | 1-naphthyl | 0 | H | CH$_3$ | Cl | 194–200 |
| 1.065 | 2-F, 6-CO$_2$CH$_3$-phenyl | 0 | H | CH$_3$ | Cl | 185–186 |
| 1.066 | 2,6-diF-phenyl | 0 | H | CH$_3$ | Cl | 200–203 |
| 1.067 | 2,6-diF-phenyl | 0 | H | CH$_3$ | OCH$_3$ | 220–225 |
| 1.068 | 2,4-diCl-phenyl | 0 | H | CH$_3$ | OCH$_3$ | 217–221 |
| 1.069 | 3-methyl-2-CO$_2$CH$_3$-thienyl | 0 | H | CH$_3$ | OCH$_3$ | 240–241 |
| 1.070 | 1-naphthyl | 0 | H | CH$_3$ | OCH$_3$ | 240 |
| 1.071 | phenyl | 0 | H | CH$_3$ | OCH$_3$ | 215–126 |
| 1.072 | 2-Cl, 3-CH$_3$-phenyl | 0 | H | CH$_3$ | OCH$_3$ | 238–240 |

TABLE 1-continued
A—(—CH$_2$)$_n$—SO$_2$—N(R$^1$)—[naphthyridine with R$^4$, R$^{4'}$]
| Compound | A | n | R$^1$ | R$^4$ | R$^{4'}$ | mp [°C.] |
|---|---|---|---|---|---|---|
| 1.073 | 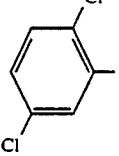 2,5-dichlorophenyl | 0 | H | CH$_3$ | N(CH$_3$)$_2$ | 252–255 |
| 1.074 | 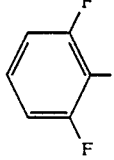 2,6-difluorophenyl | 0 | H | CH$_3$ | N(CH$_3$)$_2$ | >280 |
| 1.075 | 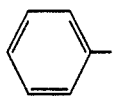 phenyl | 0 | H | CH$_3$ | SCH$_3$ | 166–168 |
| 1.076 | 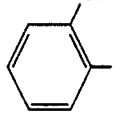 2-chlorophenyl | 0 | H | CH$_3$ | SCH$_3$ | 226–268 |
| 1.077 | 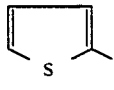 2-thienyl | 0 | H | CH$_3$ | SCH$_3$ | 261–268 |
| 1.078 | 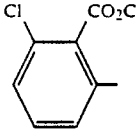 2-chloro-6-(methoxycarbonyl)phenyl | 0 | H | CH$_3$ | SCH$_3$ | 208–216 |
| 1.079 | 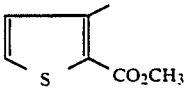 3-methyl-2-(methoxycarbonyl)thienyl | 0 | H | CH$_3$ | SCH$_3$ | 204–206 |
| 1.080 | 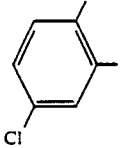 2,5-dichlorophenyl | 0 | H | CH$_3$ | SCH$_3$ | 226–230 |

TABLE 1a $$\text{A}-(\text{CH}_2)_n-\text{SO}_2-\underset{R^1}{N}-\underset{}{\text{[naphthyridine with } R^2, R^4, R^{4'}\text{]}}$$

| No. | A | n | R¹ | R² | R⁴ | R⁴' | mp [°C.] |
|---|---|---|---|---|---|---|---|
| 1.081 | 2-methoxyphenyl | 0 | H | H | CH₃ | SCH₃ | 210–215 |
| 1.082 | 2,3-difluorophenyl | 0 | H | H | CH₃ | SCH₃ | 230–233 |
| 1.083 | 2-(CO₂CH₃)phenyl | 0 | H | H | CH₃ | SCH₃ | 231–235 |
| 1.084 | 2-Cl-3-CH₃-phenyl | 0 | H | H | CH₃ | SCH₃ | 225–227 |
| 1.085 | 2,3-dichlorophenyl | 0 | H | H | CH₃ | SCH₃ | 225–228 |
| 1.086 | phenyl | 0 | H | CN | H | H | 200–208 |
| 1.087 | 2-Cl-3-CH₃-phenyl | 0 | H | CN | H | H | 182–186 |
| 1.088 | 2-thienyl | 0 | H | H | phenyl | CH₃ | >300 |
| 1.089 | 3-(F₃C)phenyl | 0 | H | H | phenyl | CH₃ | 184–188 |

TABLE 1a-continued
[Structure: A—(CH₂)ₙ—SO₂—N(R¹)— attached to naphthyridine bearing R², R⁴, R⁴']
| No. | A | n | R¹ | R² | R⁴ | R⁴' | mp [°C.] |
|---|---|---|---|---|---|---|---|
| 1.090 | 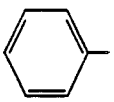 | 0 | H | H | 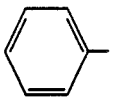 | CH₃ | 269–270 |
| 1.091 | 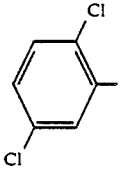 2,5-Cl₂-phenyl | 0 | H | H | 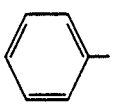 | CH₃ | 265–266 |
| 1.092 | 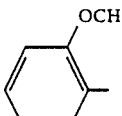 2-OCH₃-phenyl | 0 | H | H | 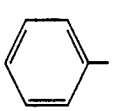 | CH₃ | 283–284 |
| 1.093 | 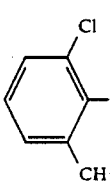 2-Cl-6-CH₃-phenyl | 0 | H | H | 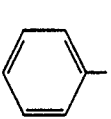 | CH₃ | 278–280 |
| 1.094 | 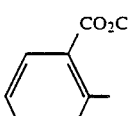 2-CO₂CH₃-phenyl | 0 | H | H | 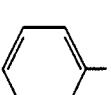 | CH₃ | 221–225 |
| 1.095 | 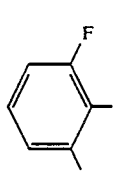 2,6-F₂-phenyl | 0 | H | H | 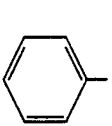 | CH₃ | 263 |
| 1.096 | 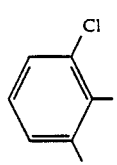 2,6-Cl₂-phenyl | 0 | H | H | 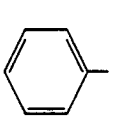 | CH₃ | 265–267 |
| 1.097 | 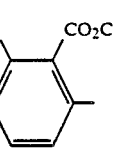 2-F-6-CO₂CH₃-phenyl | 0 | H | H | CH₃ | 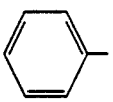 | 210–214 |
| 1.098 | 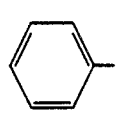 | 0 | H | H | CH₃ | 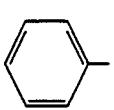 | 239–243 |

TABLE 1a-continued

A―(CH$_2$)$_n$―SO$_2$―N(R$^1$)― [pyridine with R$^2$, R$^4$, R$^{4'}$]

| No. | A | n | R$^1$ | R$^2$ | R$^4$ | R$^{4'}$ | mp [°C.] |
|---|---|---|---|---|---|---|---|
| 1.099 | 2,6-dichlorophenyl | 0 | H | H | CH$_3$ | phenyl | 248–251 |
| 1.100 | 2,4-dichlorophenyl | 0 | H | H | CH$_3$ | phenyl | 250–256 |
| 1.101 | 2-methoxyphenyl | 0 | H | H | CH$_3$ | phenyl | 273–275 |
| 1.102 | 2-chloro-6-methylphenyl | 0 | H | H | CH$_3$ | phenyl | 282–283 |
| 1.103 | 2-(CO$_2$CH$_3$)phenyl | 0 | H | H | CH$_3$ | phenyl | 220–228 |
| 1.104 | 2-chlorophenyl | 0 | H | H | CH$_3$ | phenyl | 276–277 |
| 1.105 | 2-methoxyphenyl | 0 | H | H | CH$_3$ | phenoxy | 272–273 |
| 1.106 | phenyl | 0 | H | H | CH$_3$ | phenoxy | 71–79 |
| 1.107 | 2,4-dichlorophenyl | 0 | H | H | CH$_3$ | phenoxy | 149–155 |

TABLE 1a-continued

Structure: A(-CH$_2$)$_n$-SO$_2$-N(R$^1$)- attached to a 1,8-naphthyridine with R$^2$, R$^4$, R$^{4'}$ substituents.

| No. | A | n | R$^1$ | R$^2$ | R$^4$ | R$^{4'}$ | mp [°C.] |
|---|---|---|---|---|---|---|---|
| 1.108 | 3-methyl-2-(methoxycarbonyl)thien-2-yl | 0 | H | H | CH$_3$ | phenoxy | 179–181 |
| 1.109 | 2-chloro-6-methylphenyl | 0 | H | H | CH$_3$ | phenoxy | 233–236 |
| 1.110 | 2,3-dichlorophenyl | 0 | H | H | CH$_3$ | phenoxy | 259–263 |
| 1.111 | 2,5-dichlorophenyl | 0 | H | H | H | CH$_3$ | 182–190 |
| 1.112 | 2,3-dichlorophenyl | 0 | H | H | H | CH$_3$ | 229–233 |
| 1.113 | 2,3-difluorophenyl | 0 | H | H | Cl | Cl | 193–203 |
| 1.114 | phenyl | 0 | H | H | OCH$_3$ | OCH$_3$ | 240–242 |
| 1.115 | 2-(methoxycarbonyl)phenyl | 0 | H | H | H | CH$_3$ | 194–196 |

TABLE 1a-continued

[Structure: A—(CH₂)ₙ—SO₂—N(R¹)— attached to naphthyridine with R², R⁴, R⁴']

| No. | A | n | R¹ | R² | R⁴ | R⁴' | mp [°C.] |
|---|---|---|---|---|---|---|---|
| 1.116 | 2-Cl-6-CH₃-phenyl | 0 | —SO₂-(2-Cl-6-CH₃-phenyl) | H | H | CH₃ | 218–225 |
| 1.117 | phenyl | 0 | —SO₂-phenyl | H | H | CH₃ | 199–201 |
| 1.118 | 3-Cl-2-CH₃-thien-... | 0 | H | H | CH₃ | CH₃ | 185–190 |
| 1.119 (decomp) | pentafluorophenyl | 0 | H | H | CH₃ | CH₃ | 195 |
| 1.120 (decomp) | 2-F-6-CONH₂-phenyl | 0 | H | H | CH₃ | CH₃ | 275 |
| 1.121 | 2-Cl-6-CO₂CH₃-phenyl | 0 | H | H | phenyl | CH₃ | 260–263 |
| 1.122 | 3-Cl-2-CH₃-thien- | 0 | H | H | CH₃ | Cl | 280–285 |
| 1.123 | pentafluorophenyl | 0 | H | H | CH₃ | Cl | 151–157 |
| 1.124 | 2,6-dichlorophenyl | 0 | CH₃ | H | CH₃ | Cl | 171–180 |

TABLE 1a-continued

Structure: A―(CH₂)ₙ―SO₂―N(R¹)―[naphthyridine with R², R⁴, R⁴']

| No. | A | n | R¹ | R² | R⁴ | R⁴' | mp [°C.] |
|---|---|---|---|---|---|---|---|
| 1.125 | 2,6-dichlorophenyl | 0 | H | CN | H | H | 214–218 |
| 1.126 | 2,6-difluorophenyl | 0 | H | CN | H | H | 220–224 |
| 1.127 (decomp) | 2-CONH₂-phenyl | 0 | H | H | CH₃ | phenyl | 145 |
| 1.128 (decomp) | 2-CO₂H-phenyl | 0 | H | H | CH₃ | phenyl | 138 |
| 1.129 | 2-F-6-CO₂CH₃-phenyl | 0 | K | H | CH₃ | phenyl | 260–267 |
| 1.130 | 4-F-phenyl | 0 | —SO₂—(4-F-phenyl) | H | CH₃ | CH₃ | 263–264 |
| 1.131 | 2,6-difluorophenyl | 0 | —SO₂—(2,6-difluorophenyl) | H | CH₃ | OCH₃ | 203–206 |
| 1.132 | 2-Cl-6-CO₂CH₃-phenyl | 0 | —SO₂—(2-Cl-6-CO₂CH₃-phenyl) | H | CH₃ | SCH₃ | 248–250 |
| 1.133 | phenyl | 0 | —SO₂—phenyl | H | CH₃ | SCH₃ | 243–250 |

TABLE 1a-continued
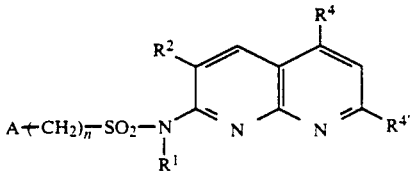
| No. | A | n | R¹ | R² | R⁴ | R⁴' | mp [°C.] |
|---|---|---|---|---|---|---|---|
| 1.134 | 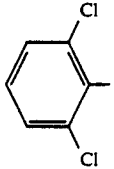 | 0 | 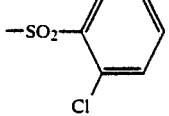 | H | OH | OH | 211-213 |
| 1.135 | 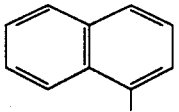 | 0 | H | H | 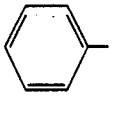 | CH₃ | >280 |
| 1.136 | 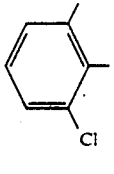 | 0 | H | H | CH₃ | H | 170-175 |
| 1.137 | 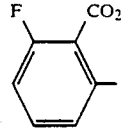 | 0 | H | H | CH₃ |  | 208-210 |
| 1.138 | 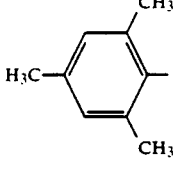 | 0 | H | H | CH₃ | Cl | 233-236 |
| 1.139 | 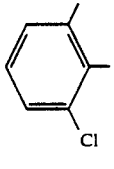 | 0 | 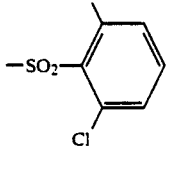 | H | H | Cl | 244-249 |
| 1.140 | 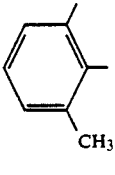 | 0 | CH₃ | H | OCH₃ | OCH₃ | 222 |
| 1.141 | 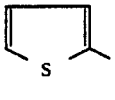 | 0 | 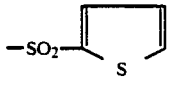 | H | CH₃ | OCH₃ | 222-230 |

TABLE 1a-continued

[Structure: A—(CH$_2$)$_n$—SO$_2$—N(R$^1$)— attached to naphthyridine with R$^2$, R$^4$, R$^{4'}$]

| No. | A | n | R$^1$ | R$^2$ | R$^4$ | R$^{4'}$ | mp [°C.] |
|---|---|---|---|---|---|---|---|
| 1.142 | 2,6-dichlorophenyl | 0 | H | H | H | OH | >280 |
| 1.143 | 2,5-dichlorophenyl | 0 | H | H | OCH$_3$ | OCH$_3$ | 265–268 |
| 1.144 | 2,6-dichlorophenyl | 0 | H | H | CH$_3$ | Br | 245–250 |
| 1.145 | 2-thienyl | 0 | —SO$_2$-(2-thienyl) | H | CH$_3$ | Cl | 215–217 |
| 1.146 | 2,6-bis(CO$_2$CH$_3$)phenyl | 0 | H | H | CH$_3$ | CH$_3$ | 182 |
| 1.147 | 2,6-dichlorophenyl | 0 | H | H | CH$_3$ | NH—NH$_2$ | >300 |

TABLE 2

[Structure: A—SO$_2$—NH— attached to pyridine ring fused with ring containing Z, R$^{4'}$, R$^{4''}$]

| No. | A | Z | R$^{4'}$ | R$^{4''}$ | mp [°C.] |
|---|---|---|---|---|---|
| 2.001 | 2,6-dichlorophenyl | \C=CH$_3$ | CH$_3$ | CH$_3$ | 210–211 |

TABLE 2-continued

A—SO$_2$—NH—[pyridine with Z and R$^{4'}$, R$^{4''}$ substituents]

| No. | A | Z | R$^{4'}$ | R$^{4''}$ | mp [°C.] |
|---|---|---|---|---|---|
| 2.002 | 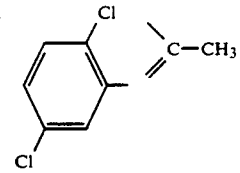 2,5-diCl-C$_6$H$_3$—C(CH$_3$)=CH$_2$ | | CH$_3$ | CH$_3$ | 202–204 |
| 2.003 | 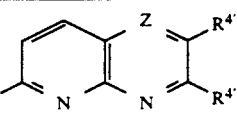 C$_6$H$_5$—C(CH$_3$)=CH$_2$ | | CH$_3$ | CH$_3$ | 188–190 |
| 2.004 | 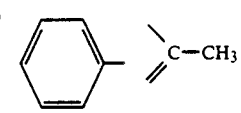 2,6-diF-C$_6$H$_3$—C(CH$_3$)=CH$_2$ | | CH$_3$ | CH$_3$ | 181–182 |
| 2.005 | 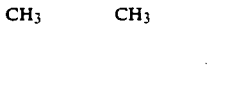 2-Cl-6-CH$_3$-C$_6$H$_3$—C(CH$_3$)=CH$_2$ | | CH$_3$ | CH$_3$ | 204–205 |
| 2.006 | 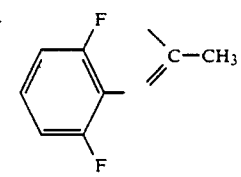 C$_6$H$_5$—C(CH$_3$)=CH$_2$ | | CH$_3$ | Cl | 198–199 |
| 2.007 | 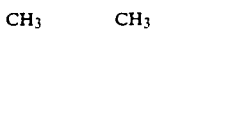 2,6-diF-C$_6$H$_3$—C(CH$_3$)=CH$_2$ | | CH$_3$ | Cl | 215–217 |
| 2.008 | 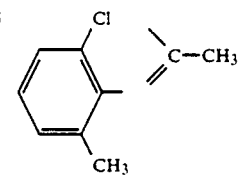 2,6-diCl-C$_6$H$_3$—C(CH$_3$)=CH$_2$ | | CH$_3$ | Cl | 199–201 |
| 2.009 | 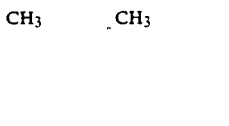 2,5-diCl-C$_6$H$_3$—C(CH$_3$)=CH$_2$ | | CH$_3$ | Cl | 222–224 |
| 2.010 | 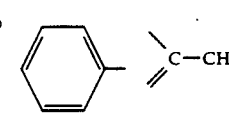 2-Cl-6-CH$_3$-C$_6$H$_3$—C(CH$_3$)=CH$_2$ | | CH$_3$ | Cl | 218–220 |

TABLE 2-continued $$A-SO_2-NH-\text{[pyridine]}-Z, R^{4'}, R^{4''}$$

| No. | A | Z | R⁴' | R⁴'' | mp [°C.] |
|---|---|---|---|---|---|
| 2.011 | 2,6-difluorophenyl-C(=)-CH₃ | | CH(CH₃)₂ | Cl | 205-208 |
| 2.012 | 2,6-dichlorophenyl-C(=)-CH₃ | | CH(CH₃)₂ | Cl | 198-201 |
| 2.013 | 2,6-dichlorophenyl-C(=)-OH | | CH₃ | OH | >250 |
| 2.014 | 2,6-dichlorophenyl-C(=)-CH₃ | | Br | CH₃ | 232-235 |
| 2.015 | 2,4-dichlorophenyl-C(=)-CH₃ | | Br | CH₃ | 221-223 |
| 2.016 | 2,6-difluorophenyl-C(=)-CH₃ | | Br | CH₃ | 188-190 |
| 2.017 | 2-chlorophenyl-C(=)-CH₃ | | Br | CH₃ | 243 |
| 2.018 | 2,6-dichlorophenyl-C(=)-CH₃ | | Cl | CH₃ | 121-122 |

TABLE 2-continued
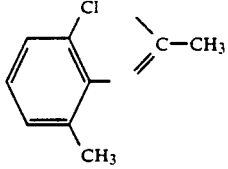
| No. | A | Z | R⁴' | R⁴" | mp [°C.] |
|---|---|---|---|---|---|
| 2.019 | 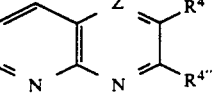 | 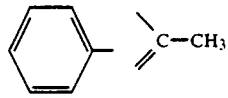 | Cl | CH₃ | 111–113 |
| 2.020 | 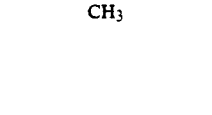 | 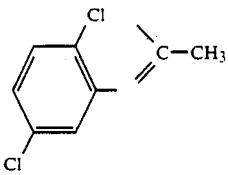 | Cl | CH₃ | 220–222 |
| 2.021 | 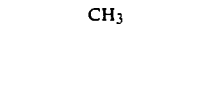 | 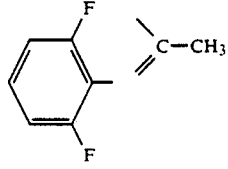 | Cl | CH₃ | 238–240 |
| 2.022 | 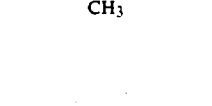 | 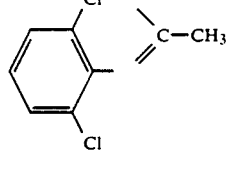 | Cl | CH₃ | 196–199 |
| 2.023 | 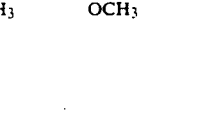 | 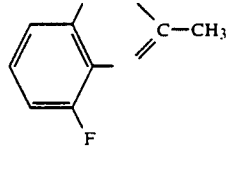 | CH₃ | OCH₃ | 235–236 |
| 2.024 |  | 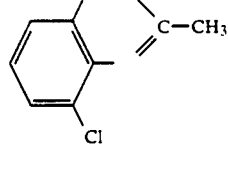 | CH₃ | OCH₃ | 224–226 |
| 2.025 | 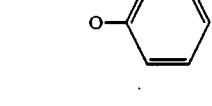 | 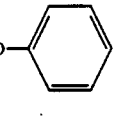 | CH₃ | 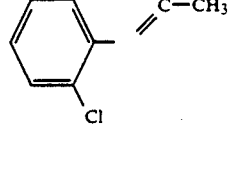 | 240 |
| 2.026 | 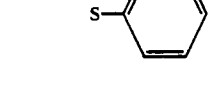 | 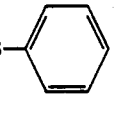 | CH₃ | (phenylthio) | 219–220 |

TABLE 2-continued
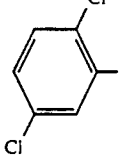
| No. | A | Z | R⁴' | R⁴'' | mp [°C.] |
|---|---|---|---|---|---|
| 2.027 | 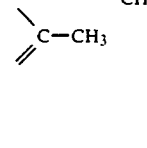 | 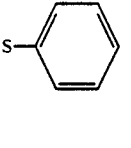 | CH₃ | 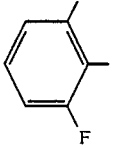 | 224–225 |
| 2.028 | 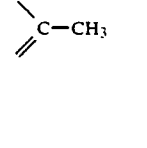 | 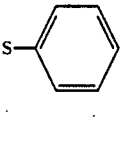 | CH₃ | 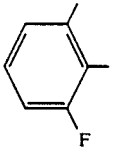 | 213–215 |
| 2.029 | 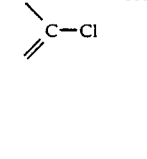 | 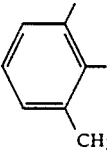 | CH₃ | Cl | 190 |
| 2.030 | 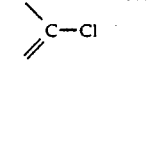 | 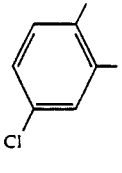 | CH₃ | Cl | 210 |
| 2.031 | 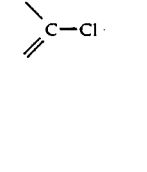 | 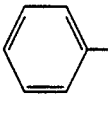 | n-C₄H₉ | Cl | 166–168 |
| 2.032 | 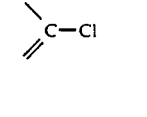 | 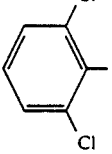 | n-C₄H₉ | Cl | 70–72 |
| 2.033 | 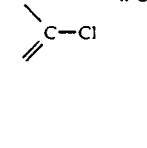 | 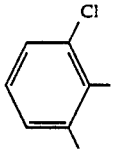 | n-C₄H₉ | Cl | 207–209 |
| 2.034 | 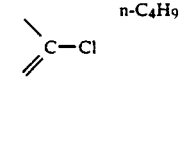 |  | n-C₄H₉ | Cl | 185–186 |

TABLE 2-continued

A—SO₂—NH—[pyridine ring with Z substituent]—N=C(R⁴')(R⁴")

| No. | A | Z | R⁴' | R⁴" | mp [°C.] |
|---|---|---|---|---|---|
| 2.035 | 2,6-difluorophenyl | \C=C—Cl / (with CH₃) | n-C₄H₉ | Cl | 132–134 |
| 2.036 | 2,6-dichlorophenyl | \C=C—Cl / (with CH₃) | CH(CH₃)₂ | Cl | 207–209 |
| 2.037 | 2,6-difluorophenyl | \C=C—Cl / (with CH₃) | CH(CH₃)₂ | Cl | >70 (decomp.) |
| 2.038 | 2,6-dichlorophenyl | \N= / | CH₃ | CH₃ | >260 |

TABLE 3

A—SO₂—NH—[pyrido-pyrimidine ring system with R², R⁴, R⁴" substituents]

| No. | A | R² | R⁴ | R⁴" | mp [°C.] |
|---|---|---|---|---|---|
| 3.001 | 2-chlorophenyl | CN | CH₃ | CH₃ | >230 |
| 3.002 | 2-fluorophenyl | CN | CH₃ | CH₃ | 210–212 |
| 3.003 | 2-(CO₂CH₃)phenyl | CN | CH₃ | CH₃ | 220–222 |

TABLE 3-continued

A—SO$_2$—NH—[pyrido-pyrimidine with R$^2$, R$^4$, R$^{4''}$ substituents]

| No. | A | R$^2$ | R$^4$ | R$^{4''}$ | mp [°C.] |
|---|---|---|---|---|---|
| 3.004 | 2,6-dichlorophenyl | CN | CH$_3$ | CH$_3$ | >230 |
| 3.005 | 2-chloro-6-methylphenyl | CN | CH$_3$ | CH$_3$ | 233–235 |
| 3.006 | 2,5-dichlorophenyl | CN | CH$_3$ | CH$_3$ | >230 |
| 3.007 | 2-chlorophenyl | SO$_2$CH$_3$ | CH$_3$ | CH$_3$ | >230 |
| 3.008 | 2,6-dichlorophenyl | SO$_2$CH$_3$ | CH$_3$ | CH$_3$ | >230 |
| 3.009 | 2,5-dichlorophenyl | SO$_2$CH$_3$ | CH$_3$ | CH$_3$ | >230 |
| 3.010 | 2-fluorophenyl | SO$_2$CH$_3$ | CH$_3$ | CH$_3$ | 107–109 |
| 3.011 | 2-(CO$_2$CH$_3$)phenyl | SO$_2$CH$_3$ | CH$_3$ | CH$_3$ | 220–222 |

TABLE 3-continued

A—SO$_2$—NH— [pyrido-pyrimidine core with R$^2$, R$^4$, R$^{4''}$ substituents]

| No. | A | R$^2$ | R$^4$ | R$^{4''}$ | mp [°C.] |
|---|---|---|---|---|---|
| 3.012 | 2-chloro-6-cyclopentylphenyl | SO$_2$CH$_3$ | CH$_3$ | CH$_3$ | >215 |
| 3.013 | 2-chloro-6-methylphenyl | H | CH$_3$ | CH$_3$ | >215 |
| 3.014 | 2-(methoxycarbonyl)-6-methylphenyl | H | CH$_3$ | CH$_3$ | 171–173 |
| 3.015 | 2,6-dichlorophenyl | H | CH$_3$ | CH$_3$ | >230 |
| 3.016 | 2-chlorophenyl | CN | OCH$_3$ | OCH$_3$ | 199–201 |
| 3.017 | 2-fluorophenyl | CN | OCH$_3$ | OCH$_3$ | 153–156 |
| 3.018 | 2-fluorophenyl | phenyl | OCH$_2$CH$_3$ | OCH$_2$CH$_3$ | 198 |
| 3.019 | 2-chlorophenyl | phenyl | OCH$_2$CH$_3$ | OCH$_2$CH$_3$ | 169–173 |

TABLE 3-continued

A—SO₂—NH structure with R², R⁴, R⁴'' substituents on pyrido-pyrimidine core

| No. | A | R² | R⁴ | R⁴'' | mp [°C.] |
|---|---|---|---|---|---|
| 3.020 | 2-Cl-phenyl | phenyl | OCH₃ | OCH₃ | 226–228 |
| 3.021 | 2-F-phenyl | phenyl | OCH₃ | OCH₃ | 198–199 |
| 3.022 | 2,3-di-Cl-phenyl | phenyl | OCH₃ | OCH₃ | >230 |
| 3.023 | 2-CO₂CH₃-phenyl | phenyl | OCH₃ | OCH₃ | 108–111 |
| 3.024 | 2,3-di-Cl-phenyl | CN | OCH₃ | OCH₃ | 218–220 |
| 3.025 | 2-CO₂CH₃-phenyl | CN | OCH₃ | OCH₃ | 211–213 |
| 3.026 | 2-Cl-phenyl | SO₂CH₃ | OCH₃ | OCH₃ | >215 |
| 3.027 | 2-CO₂CH₃-phenyl | SO₂CH₃ | OCH₃ | OCH₃ | >230 |
| 3.028 | 2-F-phenyl | SO₂CH₃ | OCH₃ | OCH₃ | 155–157 |

TABLE 3-continued

A—SO₂—NH—[pyrido-pyrimidine with R², R⁴, R⁴″]

| No. | A | R² | R⁴ | R⁴″ | mp [°C.] |
|---|---|---|---|---|---|
| 3.029 | 2,6-dichlorophenyl | SO₂CH₃ | OCH₃ | OCH₃ | 213–214 |
| 3.030 | 2,4-dichlorophenyl | SO₂CH₃ | OCH₃ | OCH₃ | 172–175 |
| 3.031 | 2-chloro-6-cyclopentylphenyl | SO₂CH₃ | OCH₃ | OCH₃ | 228–229 |
| 3.032 | 2-chloro-6-methylphenyl | SO₂CH₃ | OCH₃ | OCH₃ | 226–227 |
| 3.033 | 2,4-dimethoxyphenyl | SO₂CH₃ | OCH₃ | OCH₃ | 128 |
| 3.034 | 2-(methoxycarbonyl)phenyl | CN | CH₃ | OCH₃ | 200 |
| 3.035 | 2,6-difluorophenyl | CN | CH₃ | OCH₃ | 90–95 |
| 3.036 | 2,6-dichlorophenyl | CN | CH₃ | OCH₃ | 225–227 |

TABLE 3-continued

Structure:
A—SO₂—NH— (pyridine ring with R², R⁴, and fused pyrimidine with R⁴''')

| No. | A | R² | R⁴ | R⁴''' | mp [°C.] |
|-----|---|-----|-----|-------|----------|
| 3.037 | 2-Cl-3-CH₃-phenyl | CN | CH₃ | OCH₃ | 213–215 |
| 3.038 | 2,4-diCl-phenyl | CN | CH₃ | OCH₃ | 224–227 |
| 3.039 | 4-F-phenyl | CN | CH₃ | OCH₃ | 205–208 |
| 3.040 | 2-Cl-phenyl | CN | CH₃ | OCH₃ | 209 |

Use Examples

The herbicidal action of the sulfonamides of the formula I on the growth of plants is illustrated in greenhouse experiments.

The vessels employed were plastic flowerpots having a volume of 300 cm³ and filled with a sandy loam containing about 3.0% humus. The seeds of the test plants were sown separately, according to species.

For the postemergence treatment, either plants which had been sown in the pots and grown there were selected, or they were cultivated separately as seedlings and transplanted to the pots a few days before being treated.

Depending on growth form the plants were grown to a height of from 3 to 15 cm before being treated with the active ingredients which were suspended or emulsified in water and sprayed through finely distributing nozzles. The application rates for postemergence treatment were 2.0 and 3.0 kg of active ingredient per hectare.

The pots were set up in the greenhouse, species from warmer climates in warmer areas (20 to 35° C.) and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments were Amaranthus retroflexus, Centaurea cyanus, Chenopodium album, Cyperus iria, and Ipomoea spp.

These unwanted plants were very well combated with postemergence applications of 2.0 and 3.0 kg/ha of active ingredients 1.066 and 1.043.

We claim:

1. A sulfonamide of the formula I

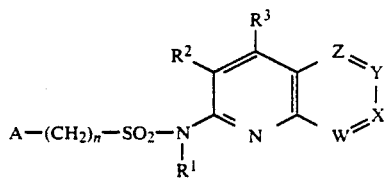

where the substituents and indices are defined as follows:

R¹ is hydrogen, cyano,

C₁-C₈-alkyl which may be substituted by one of the following radicals: C₁-C₂-alkoxy, C₁-C₂-alkylthio, aryl, aryloxy, arylthio, hetaryl, hetaryloxy and hetarylthio, C₂-C₅-alkenyl, C₂-C₄-alkynyl, COR⁴ where R⁴ is C₁-C₄-alkyl, C₁-C₄-alkoxy, C₁-C₄-alkylthio, aryl, aryloxy, arylthio, aryl-C₁-C₄-alkoxy, hetaryl, hetaryloxy, hetarylthio or hetaryl-C₁-C₄-alkoxy, CONR⁵R⁶, where R⁵ and R⁶ are identical or different and each denotes hydrogen, C₁-C₄-alkyl, C₃-C₆-cycloalkyl, C₂-C₅-alkenyl, aryl, hetaryl, aryl- $C_1$–$C_4$-alkyl, hetaryl-$C_1$–$C_4$-alkyl or $C_1$–$C_4$-alkylcarbonyl or together denote a $C_2$–$C_6$-alkylene chain, or $SO_mR^4$, where m is 1 or 2 and $R^4$ is as defined above;

$R^2$, $R^3$ are identical or different and each denotes nitro, hydroxy, carboxy, mercapto or halogen, $C_1$–$C_4$-alkyl, which may be monosubstituted by hydroxl, mercapto, amino, aryloxy or hetaryloxy and/or monosubstituted, disubstituted or trisubstituted by halogen, $C_3$–$C_6$-cycloalkyl, which may be monosubstituted, disubstituted or trisubstituted by halogen, hydroxyl, mercapto and/or $C_1$–$C_4$-alkyl, $C_3$–$C_6$-cycloalkoxy, $C_3$–$C_6$-cycloalkylthio, $C_2$–$C_5$-haloalkenyl, $C_2$–$C_4$-haloalkynyl, $C_1$–$C_4$-alkoxy, which may be monosubstituted, disubstituted or trisubstituted by halogen and/or monosubstituted by aryl or hetaryl, $C_1$–$C_4$-alkylthio, which may be monosubstituted, disubstituted or trisubstituted by halogen and/or monosubstituted by aryl or hetaryl, $C_2$–$C_5$-alkenyloxy, $C_2$–$C_4$-alkynyloxy, —$NR^5R^6$, where $R^5$ and $R^6$ are each as defined above, or one of the groups mentioned under $R^1$, W and X are each nitrogen, Y and Z each denote a group of the formula

where $R^7$ is hydrozino or one of the groups mentioned under $R^2$, n is 0 or 1 and A is aryl or hetaryl, which each may carry from one to five halogen atoms and/or from one to three of the following substituents:

—$SO_2R^8$, where $R^8$ is hydroxy, $C_1$–$C_4$-alkoxy, aryl-$C_1$–$C_4$-alkoxy, aryloxy, hetaryloxy, hetaryl-$C_1$–$C_4$-alkoxy or —$NR^5R^6$, where $R^5$ and $R^6$ are each as defined above, and/or the groups mentioned under $R^2$, wherein the term aryl defines phenyl or naphthyl and the term hetaryl defined monocyclylic or bicycylic 5- and 6- membered rings said monocyclyl or bicyclyl containing one or more heteroatoms, and the salts and N-oxides thereof.

2. A sulfonamide of the formula Ic,

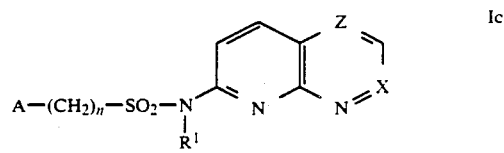

where A, X, Z, n and $R^1$ have the meaning given in claim 1 and the salts and N-oxides thereof.

3. A herbicidal agent containing a sulfonamide of the formula I as set forth in claim 1, or a salt of N-oxide thereof, and conventional formulation assistants.

4. A process for combating the growth of unwanted plants, comprising: applying a herbicidally effective amount of a sulfonamide of the formula I as set forth in claim 1, or a slat of N-oxide thereof, to plants and/or their habitat.

5. An agent for influencing plant growth, containing a sulfonamide of the formula I as set forth in claim 1, or a salt or N-oxide thereof, and conventional formulation assistants.

6. A process for influencing the growth of plants, wherein an effective amount of a sulfonamide of the formula I, as set forth in claim 1, or a salt or N-oxide thereof, is allowed to act on the plants and/or their habitat.

* * * * *